United States Patent
Sato et al.

(10) Patent No.: US 9,607,378 B2
(45) Date of Patent: Mar. 28, 2017

(54) IMAGE REGION MAPPING DEVICE, 3D MODEL GENERATING APPARATUS, IMAGE REGION MAPPING METHOD, AND IMAGE REGION MAPPING PROGRAM

(71) Applicant: Panasonic Corporation, Osaka (JP)

(72) Inventors: Taichi Sato, Kyoto (JP); Toru Nakada, Kyoto (JP); Hirohiko Kimura, Fukui (JP); Toyohiko Sakai, Fukui (JP); Hiroyuki Sashie, Fukui (JP)

(73) Assignee: PANASONIC CORPORATION, Osaka (JP)

( * ) Notice: Subject to any disclaimer, the term of this patent is extended or adjusted under 35 U.S.C. 154(b) by 23 days.

(21) Appl. No.: 14/840,626

(22) Filed: Aug. 31, 2015

(65) Prior Publication Data

US 2015/0371381 A1    Dec. 24, 2015

Related U.S. Application Data

(63) Continuation of application No. PCT/JP2014/001925, filed on Apr. 2, 2014.

(30) Foreign Application Priority Data

Apr. 5, 2013 (JP) .................. 2013-079216

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/481* (2013.01); *A61B 6/504* (2013.01); *G06T 17/00* (2013.01);
(Continued)

(58) Field of Classification Search
CPC ................ G06K 9/00; G06T 7/00; A61B 6/00
(Continued)

(56) References Cited

U.S. PATENT DOCUMENTS 6,169,917 B1 * 1/2001 Masotti .............. A61B 6/4441
600/407
2006/0250386 A1   11/2006 Movassaghi et al.
(Continued)

FOREIGN PATENT DOCUMENTS

JP        8-131429      5/1996
JP        10-5203       1/1998
(Continued)

OTHER PUBLICATIONS

International Preliminary Report on Patentability and Written Opinion issued Oct. 6, 2015 in International Application No. PCT/JP2014/001925. (English Translation).
(Continued)

*Primary Examiner* — Abolfazl Tabatabai
(74) *Attorney, Agent, or Firm* — Wenderoth, Lind & Ponack, L.L.P.

(57) ABSTRACT

An image region mapping device captures a blood vessel through which a contrast medium is passing, serially at first and second photographing angles to acquire plural image sets each including first and second projection images captured at the angles, respectively acquires brightness change information on the medium for a predetermined time period in a first image region and each of a plurality of second image regions after a bifurcation on the first projection image each of a plurality of second image regions after the bifurcation on the second projection image in each image set, the second image regions being candidates corresponding to the first image region, calculates a similarity degree between the information acquired earlier and each informa- (Continued)

tion piece acquired later, determines one of the second image regions in accordance with the calculated similarity degrees, and maps the plural vessel image regions.

15 Claims, 73 Drawing Sheets

(51) Int. Cl.
*A61B 6/00* (2006.01)
*G06T 17/00* (2006.01)
*G01N 23/04* (2006.01)
*A61B 5/05* (2006.01)

(52) U.S. Cl.
CPC ...... *G06T 2200/04* (2013.01); *G06T 2200/08* (2013.01); *G06T 2207/10116* (2013.01); *G06T 2207/30104* (2013.01)

(58) Field of Classification Search
USPC ....... 382/128, 129, 130, 131, 132, 133, 134; 378/41, 62; 600/407, 410, 411, 425
See application file for complete search history.

(56) References Cited

U.S. PATENT DOCUMENTS

| | | |
|---|---|---|
| 2008/0205722 A1 | 8/2008 | Schaefer et al. |
| 2012/0148135 A1 | 6/2012 | Van Rens et al. |

FOREIGN PATENT DOCUMENTS

| | | |
|---|---|---|
| JP | 2004-201730 | 7/2004 |
| JP | 2007-502644 | 2/2007 |
| JP | 2008-6083 | 1/2008 |
| JP | 2009-504297 | 2/2009 |
| JP | 2013-501567 | 1/2013 |
| WO | 2006/051831 | 5/2006 |

OTHER PUBLICATIONS

International Preliminary Report on Patentability and Written Opinion issued Oct. 6, 2015 in International Application No. PCT/JP2014/001926. (English Translation).

International Search Report issued in International Application No. PCT/JP2014/001925 on May 13, 2014.

G. Shechter et al., "Three-Dimensional Motion Tracking of Coronary Arteries in Biplane Cineangiograms", IEEE Transactions on Medical Imaging, Apr. 2003, vol. 22, Issue 4, pp. 493-503.

Tadahiro Yoshida, Motohide Misaki, Hiroyasu Sato, Tsuneo Saito, "Detection of Three-Dimensional Coronary Arterial Tree from Biplane Cineangiogram", The Journal of the Institute of Electronics, Information and Communication Engineers, 89/3 vol. J72-D-II No. 3, pp. 433-441, 1989 (with a partial English translation).

* cited by examiner

FIRST X-RAY IMAGE SEQUENCE

TIME

SECOND X-RAY IMAGE SEQUENCE

TIME

*Fig.23*

| TRANSLATION VECTOR T | (T_X, T_Y, T_Z) |
|---|---|
| ROTATION VECTOR R | $\begin{pmatrix} R\_0\_0, R\_0\_1, R\_0\_2 \\ R\_1\_0, R\_1\_1, R\_1\_2 \\ R\_2\_0, R\_2\_1, R\_2\_2 \end{pmatrix}$ |
| INTERNAL PARAMETERS A1 | $\begin{pmatrix} A1\_0\_0, A1\_0\_1, A1\_0\_2 \\ A1\_1\_0, A1\_1\_1, A1\_1\_2 \\ A1\_2\_0, A1\_2\_1, A1\_2\_2 \end{pmatrix}$ |
| INTERNAL PARAMETERS A2 | $\begin{pmatrix} A2\_0\_0, A2\_0\_1, A2\_0\_2 \\ A2\_1\_0, A2\_1\_1, A2\_1\_2 \\ A2\_2\_0, A2\_2\_1, A2\_2\_2 \end{pmatrix}$ |

Fig.24

|  | RADIOGRAPHING UNIT 101 | RADIOGRAPHING UNIT 102 |
|---|---|---|
| TIME 0 | IMAGE 1_0 | IMAGE 2_0 |
| TIME 1 | IMAGE 1_1 | IMAGE 2_1 |
| ⋮ | ⋮ | ⋮ |
| TIME END | IMAGE 1_END | IMAGE 2_END |

Fig.34

| | Pk | Qk_1 | Qk_2 |
|---|---|---|---|
| TIME 0 | L_Pk_0 | L_Qk_1_0 | L_Qk_2_0 |
| TIME 1 | L_Pk_1 | L_Qk_1_1 | L_Qk_2_1 |
| ... | ... | ... | ... |
| TIME T_END | L_Pk_END | L_Qk_1_END | L_Qk_2_END |

Fig. 40

| | COORDINATES OF CONTRAST POINT Pk | COORDINATES OF CORRESPONDING POINT Qk | EVALUATION VALUE FOR CORRESPONDING POINT Qk |
|---|---|---|---|
| 1ST POINT | (P1_X, P1_Y) | (Q1_X, Q1_Y) | H1 |
| 2ND POINT | (P2_X, P2_Y) | (Q2_X, Q2_Y) | H2 |
| ... | ... | ... | ... |
| KTH POINT | (PK_X, PK_Y) | (QK_X, QK_Y) | HK |

|  | COORDINATES OF 3D POINT Jk |
|---|---|
| 1ST POINT | (J1_X, J1_Y, J1_Z) |
| 2ND POINT | (J2_X, J2_Y, J2_Z) |
| ⋮ | ⋮ |
| KTH POINT | (JK_X, JK_Y, JK_Z) |

Fig.51

| PREDETERMINED RATIO | CONTRAST POINT P1 | CANDIDATE CORRESPONDING POINT Q1 | CANDIDATE CORRESPONDING POINT Q2 |
|---|---|---|---|
| 0.5 | 7.7 | 8.6 | 10.2 |
| 0.8 | 9.5 | 10.0 | 11.4 |

Fig.56

| | Pk | ... | Qk_2 |
|---|---|---|---|
| TIME 0 | 0 | ... | 0 |
| TIME 1 | L_Pk_1-L_Pk_0 | ... | L_Qk_2_1-L_Qk_2_0 |
| ... | ... | ... | ... |
| TIME END | L_Pk_END-L_Pk_(END-1) | ... | L_Qk_2_END-L_Qk_2_(END-1) |

Fig.71

| No \ ID | F1 | F2 | F3 | S1 | S2 |
|---|---|---|---|---|---|
| 1 | 0 | 0 | 0 | 0 | 1 |
| 2 | 0 | 0 | 0 | 1 | 0 |
| 3 | 0 | 0 | 0 | 1 | 1 |
| 4 | 0 | 0 | 1 | 0 | 0 |
| ... | ... | ... | ... | ... | ... |
| 10 | 0 | 1 | 0 | 1 | 0 |
| 11 | 0 | 1 | 0 | 1 | 1 |
| 12 | 0 | 1 | 1 | 0 | 0 |
| 13 | 0 | 1 | 1 | 0 | 1 |
| 14 | 0 | 1 | 1 | 1 | 0 |
| 15 | 0 | 1 | 1 | 1 | 1 |

Fig.72

| No \ c | GROUP 0 | GROUP 1 |
|---|---|---|
| 1 | [ {F1, F2, F3}, {S1} ] | [ {}, {S2} ] |
| 2 | [ {F1, F2, F3}, {S2} ] | [ {}, {S1} ] |
| 3 | [ {F1, F2, F3}, {} ] | [ {}, {S1, S2} ] |
| 4 | [ {F1, F2}, {S1, S2} ] | [ {F3}, {} ] |
| 5 | [ {F1, F2}, {S2} ] | [ {F3}, {S1} ] |
| 6 | [ {F1, F2}, {S1} ] | [ {F3}, {S2} ] |
| 7 | [ {F1, F2}, {} ] | [ {F3}, {S1, S2} ] |
| 8 | [ {F1, F3}, {S1, S2} ] | [ {F3}, {} ] |
| 9 | [ {F1, F3}, {S1} ] | [ {F3}, {S2} ] |
| 10 | [ {F1, F3}, {S2} ] | [ {F2}, {S1} ] |
| 11 | [ {F1, F3}, {} ] | [ {F2}, {S1, S2} ] |
| 12 | [ {F1}, {S1, S2} ] | [ {F2, F3}, {} ] |
| 13 | [ {F1}, {S1} ] | [ {F2, F3}, {S2} ] |
| 14 | [ {F1}, {S2} ] | [ {F2, F3}, {S1} ] |
| 15 | [ {F1}, {} ] | [ {F2, F3}, {S1, S2} ] |

Fig.74

| No | GROUPING |
|---|---|
| 1 | [ {1, 2}, {2} ] |
| 2 | [ {1, 2}, {1} ] |
| 3 | [ {1, 3}, {1} ] |
| 4 | [ {1, 3}, {2} ] |
| 5 | [ {1}, {1} ] |
| 6 | [ {1}, {2} ] |

*Fig.77*

|  | COORDINATES OF CONTRAST POINT Pk | COORDINATES OF CORRESPONDING POINT Qk | EVALUATION VALUE |
|---|---|---|---|
| 1ST POINT | (Pk_1_X, Pk_1_Y) | (Qk_1_X, Qk_1_Y) | Hα |
| 2ND POINT | (Pk_2_X, Pk_2_Y) | (Qk_1_X, Qk_1_Y) | Hα |

*Fig.78*

|  | COORDINATES OF CONTRAST POINT Pk | COORDINATES OF CORRESPONDING POINT Qk | EVALUATION VALUE |
|---|---|---|---|
| 1ST POINT | (Pk_1_X, Pk_1_Y) | (Qk_1_X, Qk_1_Y) | Hα |
| 2ND POINT | (Pk_1_X, Pk_1_Y) | (Qk_2_X, Qk_2_Y) | Hα |

*Fig.79*

| 1 | [ {1, 2} 、 {1} ] | Fig.61 |
|---|---|---|
| 2 | [ {1, 2} 、 {2} ] | Fig.64 |
| 3 | [ {1, 3} 、 {1} ] | Fig.66 |
| 4 | [ {1, 3} 、 {2} ] | Fig.67 |
| 5 | [ {1} 、 {1} ] | Fig.63 |
| 6 | [ {1} 、 {2} ] | Fig.65 |

This is a continuation application of International Application No. PCT/JP2014/001925, with an international filing date of Apr. 2, 2014, which claims priority of Japanese Patent Application No. 2013-079216 filed on Apr. 5, 2013, the content of which is incorporated herein by reference.

IMAGE REGION MAPPING DEVICE, 3D MODEL GENERATING APPARATUS, IMAGE REGION MAPPING METHOD, AND IMAGE REGION MAPPING PROGRAM

CROSS-REFERENCE TO RELATED APPLICATIONS

TECHNICAL FIELD

The technical field relates to an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

BACKGROUND ART

A catheter angiography examination exemplifies an examination of a disease caused by angiostenosis or vascular occlusion. The catheter angiography examination requires use of a contrast medium made of a radiopaque material. Injection of the contrast medium into a blood vessel to radiograph the blood vessel can clearly distinguish the blood vessel from other portions.

It is difficult for a person to grasp the shape of a blood vessel like a coronary artery having a large number of bifurcations with an image radiographed in one direction.

Research and development have been made on a technique of generating a 3D model of a blood vessel from two X-ray images captured in two directions (see Patent Literature 1 and Non-Patent Literature 1, for example). This technique enables a person to easily grasp the shape of a blood vessel.

CITATION LIST

Patent Literature

Patent Literature 1:JP 08-131429 A

Non-Patent Literature

Non-Patent Literature 1: Tadahiro YOSHIDA, Motohide MISAKI, Hiroyasu SATO, Tsuneo SAITO "Detection of Three Dimensional Coronary Arterial Tree from Biplane Cineangiogram", The Journal of the Institute of Electronics, Information and Communication Engineers, 89/3 Vol. J72-D-II No. 3, pp. 433-441

SUMMARY OF THE INVENTION

The conventional technique was, however, insufficient for generation of a 3D model of a blood vessel.

In view of the above, a non-limitative exemplary embodiment of the present disclosure provides an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

In one general aspect, the techniques disclosed here feature: An image region mapping device configured to map a plurality of image regions of a blood vessel having a bifurcation, the device comprising:

a projection image acquiring unit configured to capture the blood vessel through which a contrast medium is passing, serially at first and second photographing angles different from each other to acquire a plurality of image sets each including a first projection image captured at the first photographing angle and a second projection image captured at the second photographing angle;

a first brightness change acquiring unit configured to acquire brightness change information on the contrast medium for a predetermined time period in a first image region at a predetermined potion after the bifurcation on the first projection image in each of the image sets acquired by the projection image acquiring unit;

a second brightness change acquiring unit configured to acquire brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

a similarity degree calculator configured to calculate a similarity degree between the brightness change information acquired by the first brightness change acquiring unit and each of the brightness change information pieces acquired by the second brightness change acquiring unit; and a corresponding region determiner configured to determine one of the second image regions corresponding to the first image region in accordance with the similarity degrees calculated by the similarity degree calculator.

These general and specific aspects may be implemented using a system, a method, and a computer program, and any combination of systems, methods, and computer programs.

According to the non-limitative exemplary embodiment of the present disclosure, there is provided an image region mapping device configured to map a plurality of image regions in X-ray images of a blood vessel captured in two directions, a 3D model generating apparatus configured to generate a 3D model of the blood vessel using the image region mapping device, an image region mapping method, and an image region mapping program.

BRIEF DESCRIPTION OF THE DRAWINGS

These and other aspects and features of the present disclosure will become clear from the following description taken in conjunction with the embodiments thereof with reference to the accompanying drawings, in which:

FIG. 23 is an exemplary view of a data structure of a photographing unit information holder according to the third embodiment;

FIG. 24 is an exemplary view of a data structure of an X-ray image holder according to the third embodiment;

FIG. 34 is an exemplary view of a data structure of a brightness sequence holder according to the third embodiment;

FIG. 40 is an exemplary view of a data structure of a candidate corresponding region holder according to the third embodiment;

FIG. 51 is an exemplary view of a data structure of a predetermined ratio time acquiring unit according to the fourth embodiment;

FIG. 56 is an exemplary view of a data structure of a brightness sequence holder according to the fifth embodiment;

FIG. 71 is a view of the configuration of the grouping acquiring unit according to the sixth embodiment;

FIG. 72 is an exemplary view of grouping executed by a two-grouping unit according to the sixth embodiment;

FIG. 74 is a view indicating a grouping result of the two-grouping unit according to the sixth embodiment;

FIG. 77 is a view of the configuration of a grouping evaluator according to the sixth embodiment;

FIG. 78 is an exemplary view of corresponding information added to a corresponding information holder according to the sixth embodiment;

FIG. 79 is an exemplary view of corresponding information added to a corresponding information holder according to the sixth embodiment;

DETAILED DESCRIPTION

Figure 1:
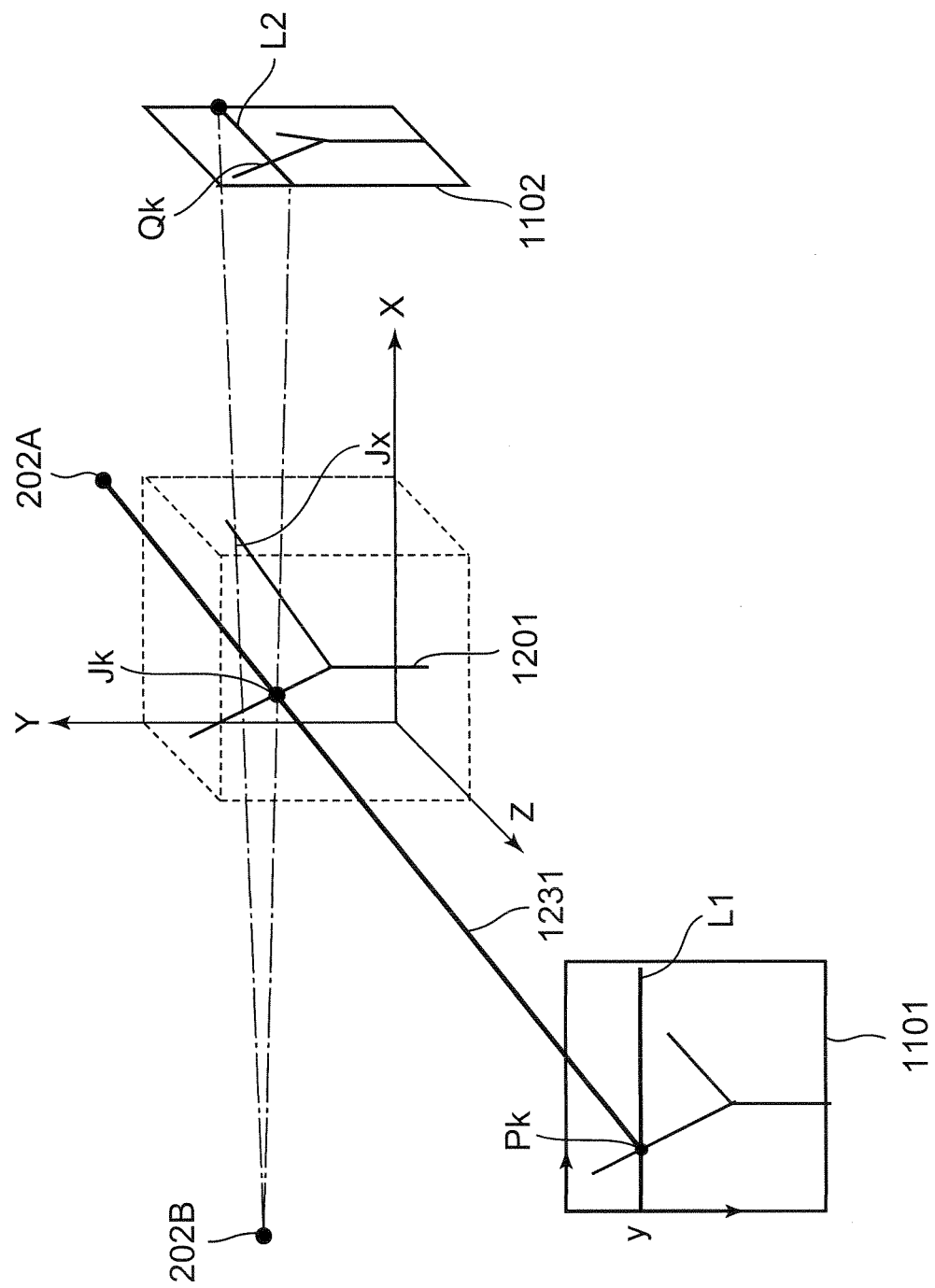
FIG. 1 is an explanatory view of generation of a 3D model of a blood vessel.

Before the description of the present disclosure proceeds, the same components are denoted by the same reference numerals in the attached drawings.

Before describing the embodiments according to the present disclosure with reference to the drawings, findings which are a basis for the present disclosure will be described.

(Finding as the Basis of the Disclosure)

FIG. 1 is an explanatory view of generation of a 3D model of a blood vessel.

X-ray generators (generating units) 202A and 202B irradiate a blood vessel 1201 with X-rays in two different directions to obtain first and second X-ray images 1101 and 1102, respectively.

The blood vessel 1201 includes a point Jk corresponding to a point Pk on the first X-ray image 1101.

When the point Jk can be specified in position on the second X-ray image 1102, the point Jk can be specified in 3D position in accordance with the triangulation principle. Similarly, a 3D model of the blood vessel 1201 can be generated by specifying in 3D position a plurality of points on the blood vessel 1201.

Described below is a method of obtaining a point on the second X-ray image 1102 corresponding to the point Jk.

Initially obtained is an epipolar line L2 in the second X-ray image 1102 for the point Pk on the first X-ray image 1101. The epipolar line L2 indicates a linear range in which a corresponding point of the point Pk possibly appears on the second X-ray image 1102. The epipolar line L2 is determined by the point Pk and a geometrical positional relation between the first and second X-ray images 1101 and 1102. There is only a point Qk as a candidate corresponding point of the point Pk in FIG. 1, so that the point Qk is determined as the corresponding point of the point Pk.

Figure 2:
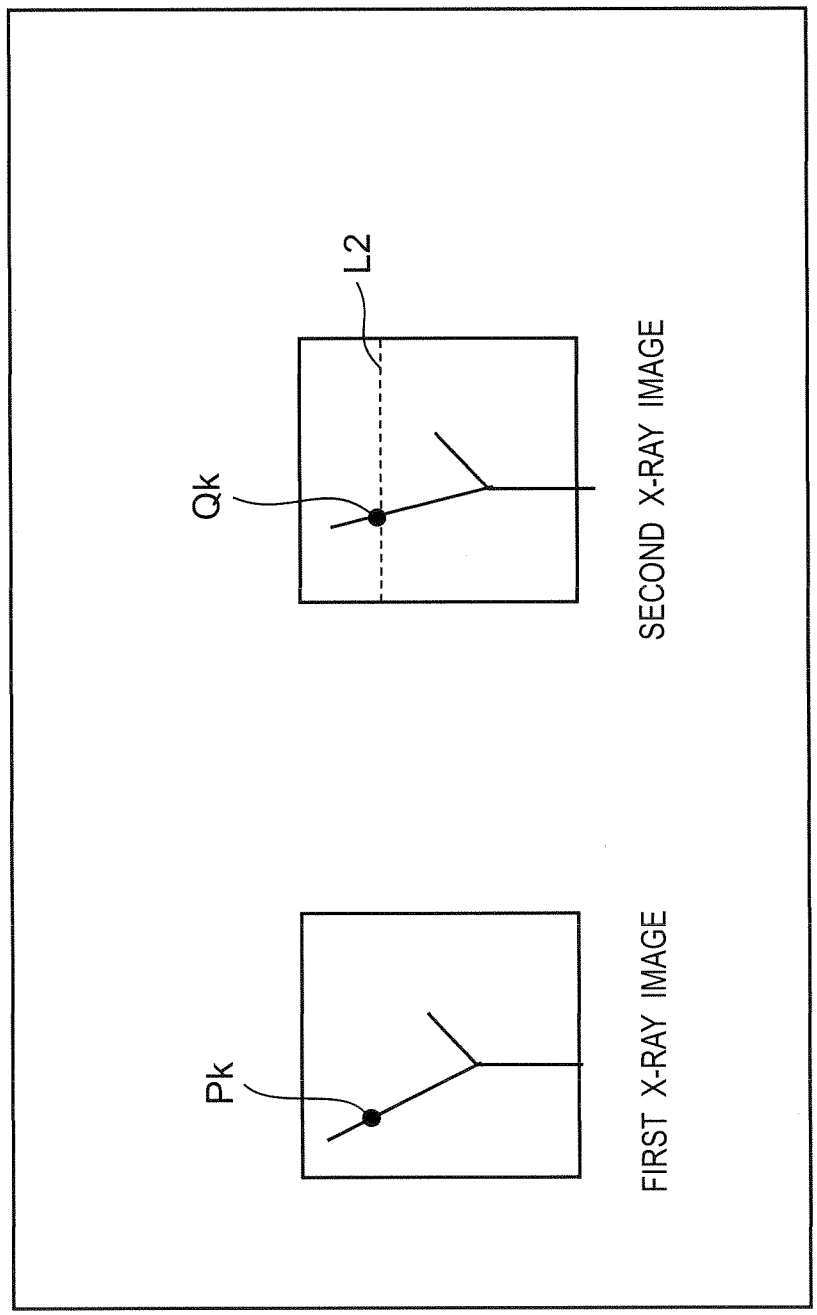
FIG. 2 is a view showing a case where there is one candidate corresponding point.

FIG. 2 is a view showing a case where there is one candidate corresponding point.

As shown in FIG. 2, in a case where the second X-ray image 1102 includes one intersection point between an end point of the blood vessel 1201 and the epipolar line L2, the point Qk is determined as the corresponding point of the point Pk.

Figure 3:
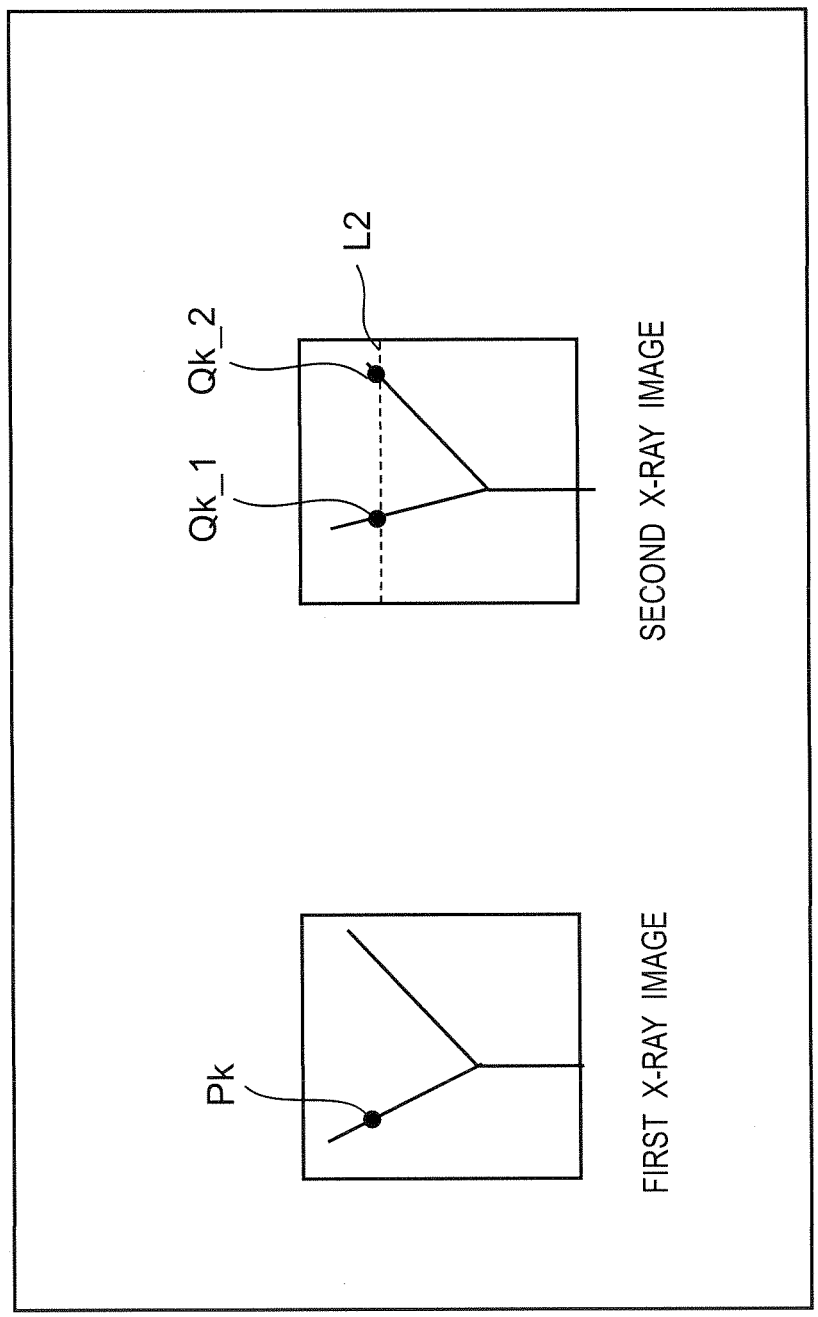
FIG. 3 is a view showing a case where there are two candidate corresponding points.

As shown in FIG. 3, in a different case where the second X-ray image 1102 includes two intersection points between the end point of the blood vessel 1201 and the epipolar line L2, the corresponding point of the point Pk cannot be determined between points Qk_1 and Qk_2.

First, the basic concept of the present disclosure is explained.

Examples of the disclosed technique are as follows.

1st aspect: An image region mapping device configured to map a plurality of image regions of a blood vessel having a bifurcation, the device comprising:

a projection image acquiring unit configured to capture the blood vessel through which a contrast medium is passing, serially at first and second photographing angles different from each other to acquire a plurality of image sets each including a first projection image captured at the first photographing angle and a second projection image captured at the second photographing angle;

a first brightness change acquiring unit configured to acquire brightness change information on the contrast medium for a predetermined time period in a first image region at a predetermined potion after the bifurcation on the first projection image in each of the image sets acquired by the projection image acquiring unit;

a second brightness change acquiring unit configured to acquire brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

a similarity degree calculator configured to calculate a similarity degree between the brightness change information acquired by the first brightness change acquiring unit and each of the brightness change information pieces acquired by the second brightness change acquiring unit; and a corresponding region determiner configured to determine one of the second image regions corresponding to the first image region in accordance with the similarity degrees calculated by the similarity degree calculator.

The 1st aspect enables appropriate mapping of the plurality of image regions in the X-ray images of the blood vessel captured in the two directions.

2nd aspect: The image region mapping device according to the 1st aspect, wherein the first brightness change acquiring unit acquires brightness of the contrast medium at each of a plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a brightness normalizer configured to normalize brightness, the brightness normalizer, normalizes by calculating a difference value between reference brightness in a case of not capturing the blood vessel and the brightness acquired by the first brightness change acquiring unit to acquire normalized brightness change information, and normalizes by calculating a difference value between the reference brightness in the case of not capturing the blood vessel and the brightness acquired by the second brightness change acquiring unit to acquire normalized brightness change information, and the similarity degree calculator calculates a similarity degree between the brightness change information acquired by the first brightness change acquiring unit and normalized by the brightness normalizer and each of the brightness change information pieces acquired by the second brightness change acquiring unit and normalized by the brightness normalizer.

The 2nd aspect enables determination of an appropriate corresponding point out of a plurality of candidate corresponding points even when brightness of the blood vessel captured at the first photographing angle is different from brightness of the blood vessel captured at the second photographing angle.

3rd aspect: The image region mapping device according to the 2nd aspect, wherein the first brightness change acquiring unit acquires brightness of the contrast medium at each of the plurality of times in the first image region as brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the brightness normalizer normalizes the brightness change information at each of the times acquired by each of the first brightness change acquiring unit and the second brightness change acquiring unit to acquire normalized brightness change information, the similarity degree calculator calculates a difference between the brightness at each of the times acquired by the first brightness change acquiring unit and normalized by the brightness normalizer and each of the brightness change information pieces at each of the times acquired by the second brightness change acquiring unit and normalized by the brightness normalizer to calculate, as a similarity degree, a sum of absolute values of the differences for the predetermined time period, and the corresponding region determiner determines that the second image region having a minimum sum of the absolute values of the differences calculated by the similarity degree calculator as the similarity degree corresponds to the first image region.

The 3rd aspect enables determination of an appropriate corresponding point out of a plurality of candidate corresponding points even when brightness of the blood vessel captured at the first photographing angle is different from brightness of the blood vessel captured at the second photographing angle and brightness in each photographing time period includes noise.

4th aspect: The image region mapping device according to the 2nd aspect, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the first brightness change acquiring unit acquires a graph by chronologically plotting the brightness of the contrast medium in the first image region as the brightness change information, the second brightness change acquiring unit acquires a graph by chronologically plotting the brightness of the contrast medium in each of the plurality of second image regions as the brightness change information, the brightness normalizer normalizes the graphs acquired by the first brightness change acquiring unit and the second brightness change acquiring unit to acquire normalized graphs, the similarity degree calculator calculates a similarity degree in shape between the graph acquired by the first brightness change acquiring unit and normalized by the brightness normalizer and each of the plurality of graphs acquired by the second brightness change acquiring unit and normalized by the brightness normalizer, and the corresponding region determiner determines that the second image region having a highest similarity degree in shape calculated by the similarity degree calculator corresponds the first image region.

The 4th aspect enables determination of an appropriate corresponding point out of a plurality of candidate corresponding points even when brightness of the blood vessel captured at the first photographing angle is different from brightness of the blood vessel captured at the second photographing angle.

5th aspect: The image region mapping device according to the 4th aspect, wherein the similarity degree calculator calculates as a similarity degree, a difference between an area of the graph acquired by the first brightness change acquiring unit and normalized by the brightness normalizer and an area of each of the plurality of graphs acquired by the second brightness change acquiring unit and normalized by the brightness normalizer, and the corresponding region determiner determines that the second image region of the graph having a minimum difference calculated by the similarity degree calculator as the similarity degree corresponds to the first image region.

The 5th aspect enables determination of an appropriate corresponding point out of a plurality of candidate corresponding points even when brightness of the blood vessel captured at the first photographing angle is different from brightness of the blood vessel captured at the second photographing angle and brightness in each photographing time period includes noise.

6th aspect: The image region mapping device according to the 2nd aspect, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a predetermined ratio time acquiring unit configured to acquire a predetermined ratio time when brightness of a point in each of the first image region and the second image regions reaches a predetermined ratio to maximum brightness of the point, the predetermined ratio time acquiring unit acquires the predetermined ratio time when a brightness sequence as the brightness change information normalized by the brightness normalizer in each of the first image region and the second image regions has a value reaching the predetermined ratio, and the similarity degree calculator determines that, in the plurality of second image regions, the second image region having the predetermined ratio time having a higher similarity degree to the predetermined ratio time of the first image region corresponds to the first image region.

The 6th aspect enables determination of an appropriate corresponding point out of a plurality of candidate corresponding points even when brightness of the blood vessel captured at the first photographing angle is different from brightness of the blood vessel captured at the second photographing angle.

7th aspect: The image region mapping device according to the 2nd aspect, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a peak time acquiring unit configured to acquire a peak time of a differential brightness sequence obtained by differentiating a brightness sequence serving as the brightness change information normalized by the brightness normalizer in each of the first image region and the second image regions, the peak time acquiring unit acquires the peak time of the differential brightness sequence obtained by differentiating the brightness sequence in each of the first image region and the second image regions, and the similarity degree calculator determines that, in the plurality of second image regions, the second image region having the peak time having a higher similarity degree to the peak time of the first image region corresponds to the first image region.

The 7th aspect enables determination of an appropriate corresponding point out of a plurality of candidate corresponding points even when brightness of the blood vessel captured at the first photographing angle is different from brightness of the blood vessel captured at the second photographing angle.

8th aspect: The image region mapping device according to any one of the 1st to 7th aspects, further comprising:

a photographing unit information acquiring unit configured to acquire relative positional information between positional information on a first radiographing device configured to capture the blood vessel at the first photographing angle and positional information on a second radiographing device configured to capture the blood vessel at the second photographing angle;

a blood vessel region acquiring unit configured to acquire positional information on the first image region on the first projection image; and a candidate corresponding region acquiring unit configured to calculate an epipolar plane defined by the first radiographing device, the second radiographing device, and the first image region from the positional information acquired by the photographing unit information acquiring unit, calculate an epipolar line as an intersection line between the calculated epipolar plane and the second projection image on the second projection image, and acquire positional information positioned on the calculated epipolar line for each of the plurality of second image regions, and the second brightness change acquiring unit acquires a brightness change at a position of the positional information in each of the plurality of second image regions acquired by the candidate corresponding region acquiring unit.

The 8th aspect enables determination of the plurality of second image regions corresponding to the first image region by calculating the epipolar line.

9th aspect: A 3D model generating apparatus configured to generate a 3D model of the blood vessel having the bifurcation, the apparatus comprising:

the image region mapping device according to any one of the 1st to 8th aspects; and a 3D model generator configured to generate the 3D model of the blood vessel in accordance with the information determined by the image region mapping device.

10th aspect: An image region mapping method of mapping a plurality of image regions of a blood vessel having a bifurcation, the method comprising:

with a projection image acquiring unit, capturing the blood vessel through which a contrast medium is passing, serially at first and second photographing angles different from each other to acquire a plurality of image sets each including a first projection image captured at the first photographing angle and a second projection image captured at the second photographing angle;

with a first brightness change acquiring unit, acquiring brightness change information on the contrast medium for a predetermined time period in a first image region at a predetermined potion after the bifurcation on the first projection image in each of the image sets acquired by the projection image acquiring unit;

with a second brightness change acquiring unit, acquiring brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

with a similarity degree calculator, calculating a similarity degree between the brightness change information acquired by the first brightness change acquiring unit and each of the brightness change information pieces acquired by the second brightness change acquiring unit; and with a corresponding region determiner, determining one of the second image regions corresponding to the first image region in accordance with the similarity degrees calculated by the similarity degree calculator.

11th aspect: An image region mapping program configured to map a plurality of image regions of a blood vessel having a bifurcation, the program causing a computer to function as:

a projection image acquiring unit configured to capture the blood vessel through which a contrast medium is passing, serially at first and second photographing angles different from each other to acquire a plurality of image sets each including a first projection image captured at the first photographing angle and a second projection image captured at the second photographing angle;

a first brightness change acquiring unit configured to acquire brightness change information on the contrast medium for a predetermined time period in a first image region at a predetermined potion after the bifurcation on the first projection image in each of the image sets acquired by the projection image acquiring unit;

a second brightness change acquiring unit configured to acquire brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

a similarity degree calculator configured to calculate a similarity degree between the brightness change information acquired by the first brightness change acquiring unit and each of the brightness change information pieces acquired by the second brightness change acquiring unit; and a corresponding region determiner configured to determine one of the second image regions corresponding to the first image region in accordance with the similarity degrees calculated by the similarity degree calculator.

(First Embodiment)

<Configuration of Apparatus>

Figure 4:
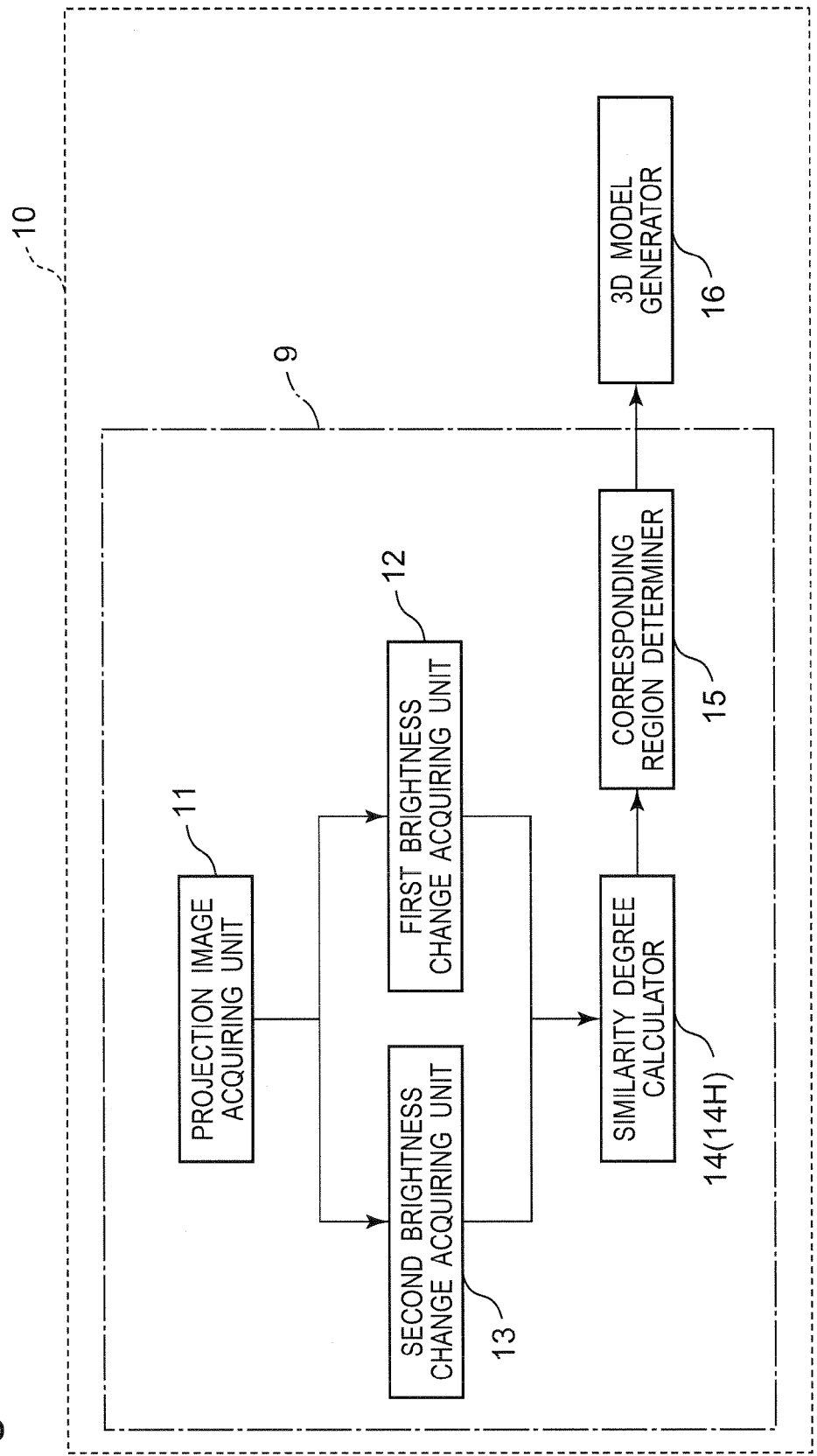
FIG. 4 is a block diagram of the functional configuration of a 3D model generating apparatus according to a first embodiment.

FIG. 4 is a functional block diagram of a 3D model generating apparatus 10 including an image region mapping device 9 according to the first embodiment of the present disclosure.

The 3D model generating apparatus 10 includes the image region mapping device 9 and a 3D model generator (generating unit) 16.

The image region mapping device 9 includes a projection image acquiring unit 11, a first brightness change acquiring unit 12, a second brightness change acquiring unit 13, a similarity degree calculator (calculating unit) 14, and a corresponding region determiner (determining unit) 15.

<Projection Image Acquiring Unit 11>

The projection image acquiring unit 11 captures the blood vessel 1201 through which a contrast medium is passing, serially at first and second photographing angles to acquire a plurality of image sets, each including the first X-ray image (first projection image) 1101 captured at the first photographing angle and the second X-ray image (second projection image) 1102 captured at the second photographing angle, until timing commanded by an input IF 114 (from photographing start timing to photographing end timing) (at predetermined time intervals, for example).

<First Brightness Change Acquiring Unit 12>

The first brightness change acquiring unit 12 acquires brightness change information on the contrast medium for the predetermined time period for a first image region (point, or a contrast point) Pk at a predetermined portion after a bifurcation of the blood vessel 1201 on the first X-ray image 1101 acquired by the projection image acquiring unit 11.

Figure 5:
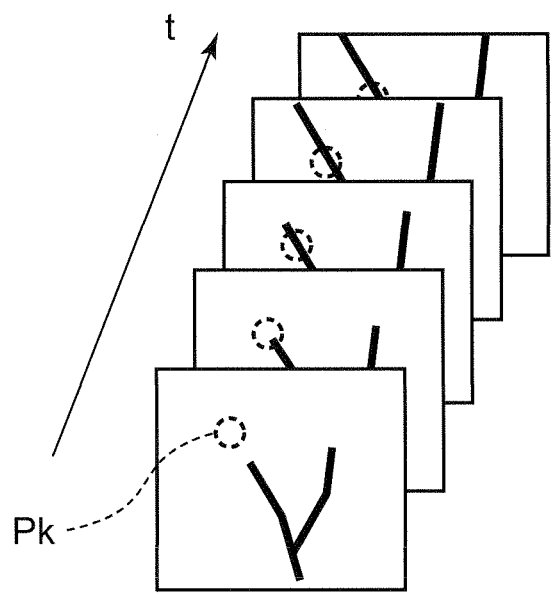
FIG. 5 is an exemplary view of information acquired by a first brightness change acquiring unit.

FIG. 5 exemplarily shows information acquired by the first brightness change acquiring unit 12.

The first brightness change acquiring unit 12 acquires a first X-ray image sequence as a sequence of the first X-ray images 1101 aligned chronologically, from the projection image acquiring unit 11. The first image region Pk is a region that is fixed on the first X-ray image 1101 and does not shift in the first X-ray image sequence. In FIG. 5, the first image region Pk has high brightness if the contrast medium has not yet reached the first image region Pk. In contrast, the first image region Pk has lower brightness if the contrast medium has reached the first image region Pk.

The first brightness change acquiring unit 12 acquires brightness information on the first image region Pk from the first X-ray image sequence. The first brightness change acquiring unit 12 chronologically acquires brightness of the first image region Pk, for example.

The first image region Pk is a portion after the bifurcation of the blood vessel 1201, and does not include other blood vessels 1201.

The first image region Pk can be a region that includes the blood vessel 1201 after the bifurcation (e.g. the first image region Pk is larger in width than the blood vessel 1201), but is preferably a region that includes in the blood vessel 1201 after the bifurcation (e.g. the first image region Pk is smaller in width than the blood vessel 1201). Such a first image region Pk enables extraction of brightness of only the contrast medium without brightness of any portion other than the blood vessel 1201.

The first image region Pk can be an arbitrary point in a region that possibly includes a blood vessel on the first X-ray image 1101.

Figure 6:
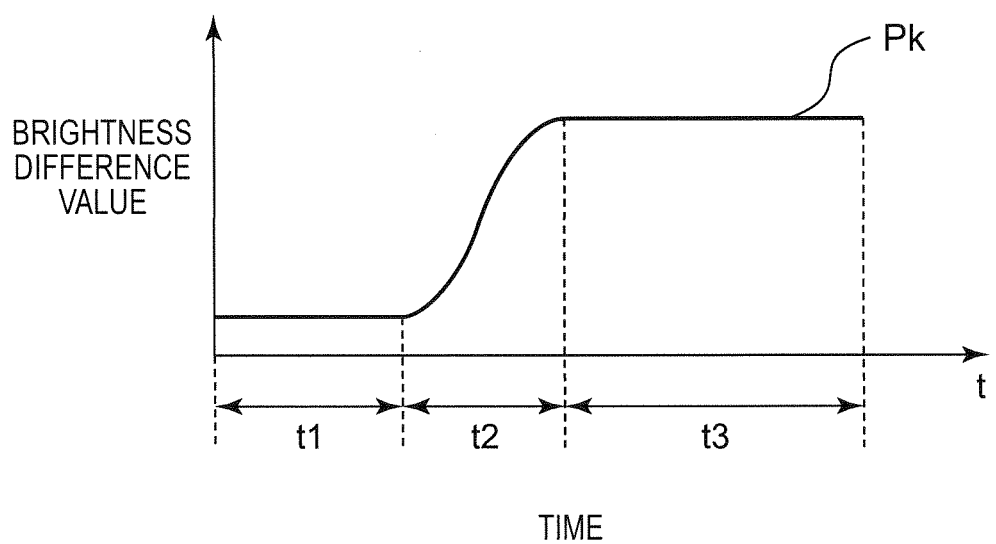
FIG. 6 is a graph indicating how brightness in a first image region changes.

FIG. 6 shows how the brightness in the first image region Pk changes.

Assume that the ordinate axis indicates a difference value from reference brightness and the transverse axis indicates time. Brightness change information on the first image region Pk is exemplarily indicated in the graph of FIG. 6. The contrast medium has not reached the first image region Pk in a time period t1 and the brightness thus has a small difference value. In a time period t2, the contrast medium has reached the first image region Pk and gradually expands in the first image region Pk. The brightness thus has a gradually increasing difference value. The contrast medium has sufficiently reached the first image region Pk in a time period t3 and the brightness thus has a constant difference value.

The ordinate axis is assumed to indicate the difference value from the reference brightness in this example. The ordinate axis can alternatively indicate a difference value between the maximum brightness and the brightness.

<Second Brightness Change Acquiring Unit 13>

The second brightness change acquiring unit 13 acquires brightness change information on the contrast medium for the predetermined time period for each of second image regions Qk_n (n=1, 2, . . . , N) that is a region at the predetermined portion after the bifurcation on the second X-ray image 1102 acquired by the projection image acquiring unit 11 as candidate image regions corresponding to the first image region Pk.

Described below is how the second brightness change acquiring unit 13 calculates and acquires the plurality of second image regions Qk_n as the candidate image regions corresponding to the first image region Pk.

Figure 7:
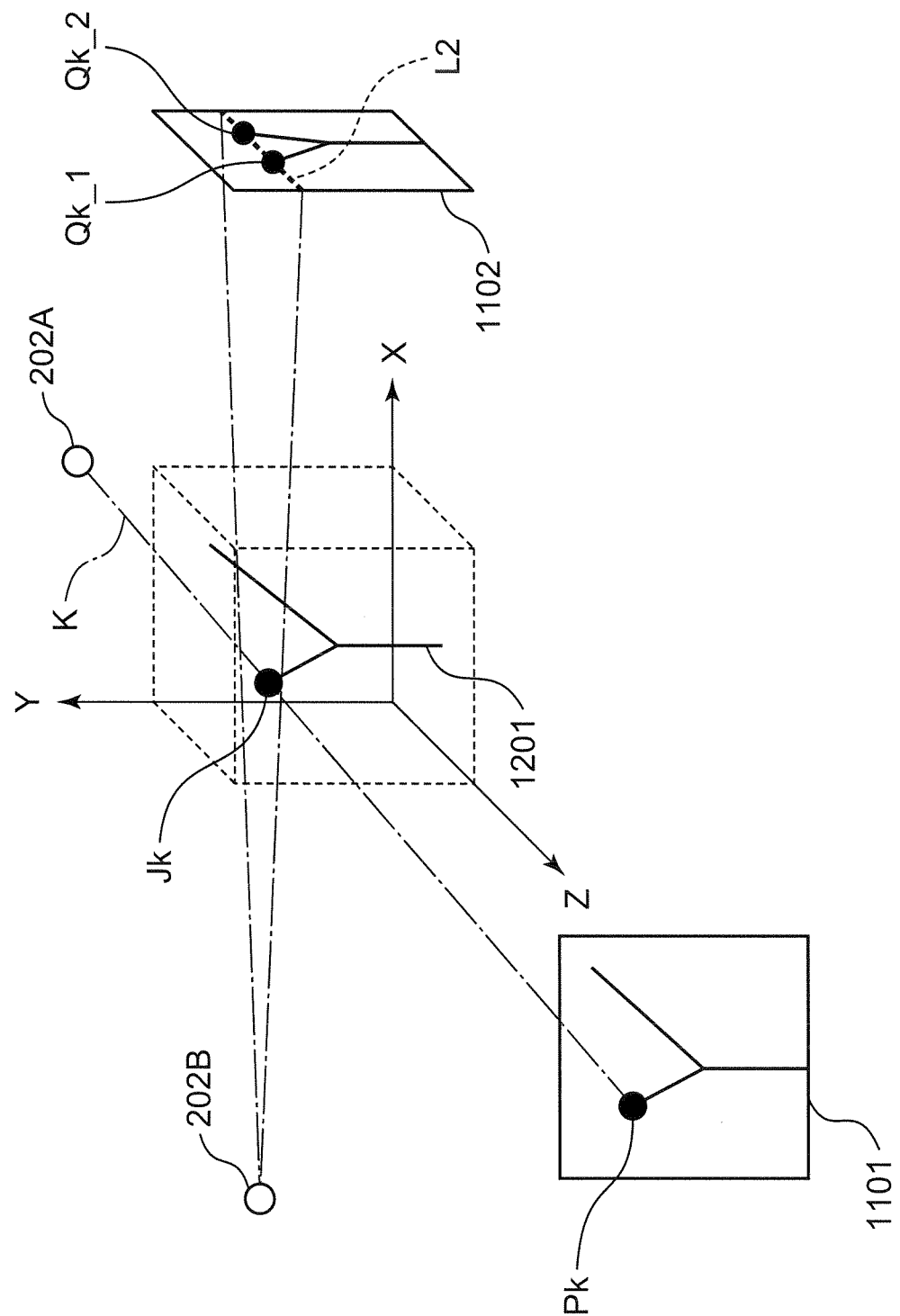
FIG. 7 is an explanatory view showing a method of calculating second image regions.

FIG. 7 is an explanatory view of the method of calculating the second image regions Qk_n.

The point Jk on the blood vessel 1201 is located on a straight line K that connects the X-ray generator 202A and the point Pk on the first X-ray image 1101. The straight line K matches the epipolar line L2 on the second X-ray image 1102. The second brightness change acquiring unit 13 can calculate the straight line K or the epipolar line L2 from positional information on the X-ray generators 202A and 202B and capture information on photographing devices configured to capture the first and second X-ray images 1101 and 1102. More specifically, the second brightness change acquiring unit 13 can calculate a parameter l2 of the epipolar line L2 in accordance with Equations 1 and 2. Assume that the positional information on the X-ray generators 202A and 202B is expressed by a translation vector T and a rotation vector R and capture information on the photographing devices is expressed by internal parameters A1 and A2.

$$F = A1^{-T}[T]_x R A2^{-1} \quad \text{(Equation 1)}$$

$$l2 = Fm \quad \text{(Equation 2)}$$

In Equation 1, F denotes a fundamental matrix, $A1^{-T}$ denotes a transpose of a transposed matrix of the internal parameter A1, and $[T]_x$ denotes a skew-symmetric matrix of the translation vector T. Assume that the calculated parameter l2 of the epipolar line L2 is expressed by (a, b, c) T, the epipolar line L2 satisfies the relational expression of Equation 3.

$$ax + by + c = 0 \quad \text{(Equation 3)}$$

The second brightness change acquiring unit 13 calculates an intersection point between the epipolar line L2 calculated by the second brightness change acquiring unit 13 and an end point of the contrast medium on the second X-ray image 1102. More specifically in FIG. 7, the second brightness change acquiring unit 13 calculates the second image regions Qk_1 and Qk_2.

Figure 8:
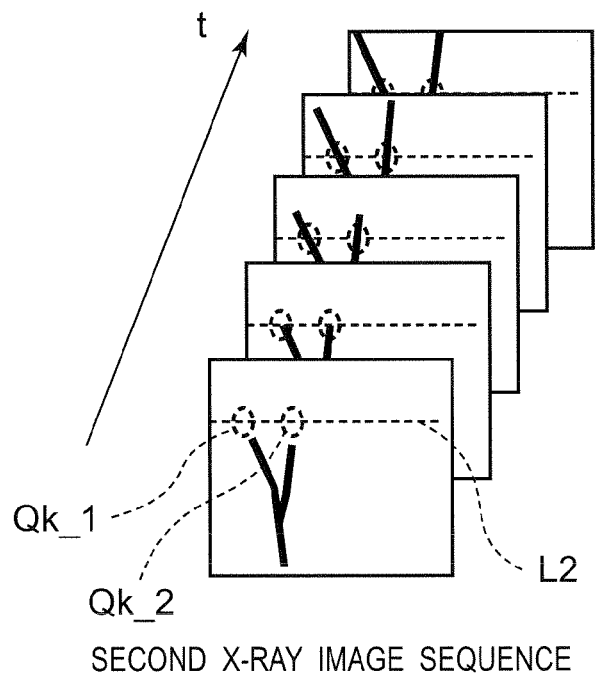
FIG. 8 is an exemplary view of information acquired by a second brightness change acquiring unit.

FIG. 8 exemplarily shows information acquired by the second brightness change acquiring unit 13.

The second brightness change acquiring unit 13 acquires a second X-ray image sequence as a sequence of the second X-ray images 1102 aligned chronologically, from the projection image acquiring unit 11. The second image regions Qk_1 and Qk_2 are regions that are fixed on the second X-ray image 1102 and do not shift in the second X-ray image sequence. If the contrast medium has not yet reached the second image regions Qk_1 and Qk_2, the second image regions Qk_1 and Qk_2 each have high brightness. If the contrast medium has reached the second image regions Qk_1 and Qk_2, the second image regions Qk_1 and Qk_2 each have lower brightness.

The second brightness change acquiring unit 13 acquires brightness information on the second image regions Qk_1 and Qk_2 from the second X-ray image sequence. The second brightness change acquiring unit 13 chronologically acquires brightness of each of the second image regions Qk_1 and Qk_2, for example.

The second image regions Qk_1 and Qk_2 are portions different from each other after the bifurcation of the blood vessel 1201 and do not include other blood vessels 1201.

The second image regions Qk_1 and Qk_2 can be regions each of which includes the blood vessel 1201 after the bifurcation, but each of which preferably includes in the blood vessel 1201 after the bifurcation. Such a second image region Qk enables extraction of brightness of only the contrast medium without brightness of any portion other than the blood vessel 1201.

Each of the second image regions Qk_1 and Qk_2 can be an arbitrary point on the second X-ray image 1102.

Figure 9:
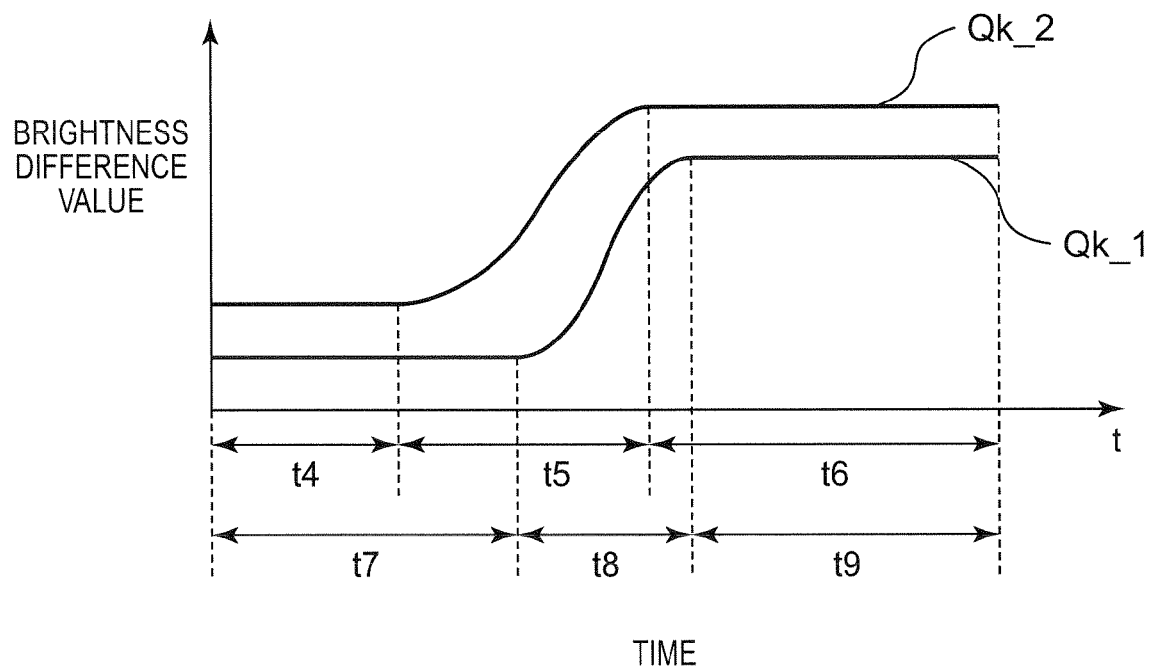
FIG. 9 is a graph indicating how brightness in each of the second image regions changes.

FIG. 9 exemplarily shows brightness change information on the second image regions Qk_1 and Qk_2.

Assume that the ordinate axis indicates a difference value from the reference brightness and the transverse axis indicates time. Each of the brightness change information on the second image regions Qk_1 and Qk_2 is indicated in the graph of FIG. 9. The first brightness change acquiring unit 12 can acquire, as brightness change information, a graph of chronologically plotted brightness of the contrast medium in the first image region. The second brightness change acquiring unit 13 can acquire, as brightness change information, a graph of chronologically plotted brightness of the contrast medium in each of the second image regions. In the graph of FIG. 9, the contrast medium has not yet reached the second image region Qk_2 in a time period t4 and the brightness thus has a small difference value. In a time period t5, the contrast medium has reached the second image region Qk_2 and gradually expands in the second image region Qk_2. The brightness thus has a gradually increasing difference value. The contrast medium has sufficiently reached the second image region Qk_2 in a time period t6 and the brightness thus has a constant difference value. The contrast medium has not yet reached the second image region Qk_1 in a time period t7 and the brightness thus has a small difference value. In a time period t8, the contrast medium has reached the second image region Qk_1 and gradually expands in the second image region Qk_1. The brightness thus has a gradually increasing difference value. The contrast medium has sufficiently reached the second image region Qk_1 in a time period t9 and the brightness thus has a constant difference value.

The indications of the second image regions Qk_1 and Qk_2 are different from each other in graph shape for the following reason.

In a case where the blood vessel 1201 extends vertically upward after the bifurcation, the contrast medium flows against the gravity at a low flow rate. In a different case where the blood vessel 1201 extends vertically downward after the bifurcation, the contrast medium flows at a high flow rate. That is, the flow rate of the contrast medium varies depending on whether the blood vessel 1201 extends vertically upward or downward. The contrast medium has different flow volumes at each time in the second image regions Qk_1 and Qk_2. The indications are accordingly different from each other in graph shape.

The contrast medium has a different flow rate also in a case where the blood vessel 1201 after the bifurcation has a different diameter. The indications of the second image regions Qk_1 and Qk_2 are thus different from each other in graph shape.

<Similarity Degree Calculator 14>

The similarity degree calculator 14 calculates a similarity degree between the brightness change information acquired by the first brightness change acquiring unit 12 and each brightness change information pieces acquired by the second brightness change acquiring unit 13.

Figure 10:
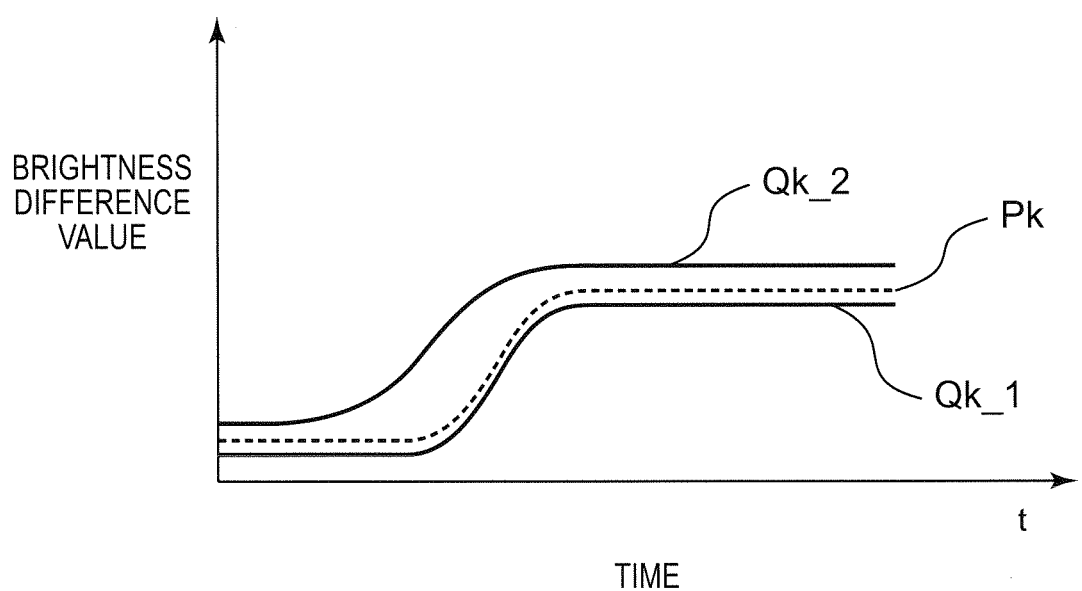
FIG. 10 is an explanatory graph of a similarity degree calculated by a similarity degree calculator.

FIG. 10 is an explanatory graph exemplifying the similarity degrees calculated by the similarity degree calculator 14.

FIG. 10 is a graph of the brightness change information on each of the first image region Pk and the second image regions Qk_1 and Qk_2. The brightness change information on the first image region Pk is indicated by a dotted line. The brightness change information on each of the second image regions Qk_1 and Qk_2 is indicated by a solid line.

The similarity degree calculator 14 calculates a similarity degree of the indication of each of the second image regions Qk_1 and Qk_2 to the indication of the first image region Pk. For example, the similarity degree calculator 14 calculates the absolute value of the difference between the brightness of each of the second image regions Qk_1 and Qk_2 and the brightness of the first image region Pk at each time, and calculates the sum of the absolute values of the differences for the predetermined time period. The similarity degree is higher as the sum of the absolute values of the differences calculated by the similarity degree calculator 14 is smaller. For example, brightness at each time is captured at the time intervals of $1/30$ seconds.

The similarity degree is high if the second image region Qk_1 and the first image region Pk are similar to each other in shape. The similarity degree calculator 14 can be replaced with a shape similarity degree calculator 14H (see FIG. 4) configured to calculate a similarity degree in shape between the indication of each of the second image regions Qk_1 and Qk_2 and the indication of the first image region Pk through pattern matching or the like. The shape similarity degree calculator 14H can alternatively calculate a similarity degree in shape between indications of normalized brightness change information pieces to be described later. At this time, the similarity degree is also high if the second image region Qk_1 and the first image region Pk are similar to each other in shape.

According to a different example, the similarity degree calculator 14 calculates an area value for the predetermined time period for each of the indications of the second image regions Qk_1 and Qk_2 to the indication of the first image region Pk. The similarity degree calculator 14 then calculates a difference between the area value of each of the second image regions Qk_1 and Qk_2 and the area value of the first image region Pk. The similarity degree is higher as the difference in area value calculated by the similarity degree calculator 14 is smaller.

Calculation of a similarity degree by the similarity degree calculator 14 is not limited to the method mentioned above. The similarity degree calculator 14 can alternatively calculate a similarity degree from a tendency of increase or decrease of a difference value between brightness and the reference brightness at each time for each of the indications of the image regions.

<Corresponding Region Determiner 15>

The corresponding region determiner 15 determines, as a region corresponding to the first image region Pk, the second image region having the highest similarity degree out of a plurality of similarity degrees calculated by the similarity degree calculator 14.

More specifically, the corresponding region determiner 15 determines which one of the second image regions Qk_1 and Qk_2 corresponds to the first image region Pk from a result of calculation by the similarity degree calculator 14 of the similarity degree between the brightness change information on each of the second image regions Qk_1 and Qk_2 and the brightness change information on the first image region Pk. The corresponding region determiner 15 determines, as the region corresponding to the first image region Pk, the second image region having the higher similarity degree. The second image region Qk_1 corresponds to the first image region Pk in FIG. 10.

If there are second image regions Qk_n each having a similarity degree higher than a predetermined threshold, the corresponding region determiner 15 determines that the second image region Qk_n initially decided as having a similarity degree higher than the predetermined threshold corresponds to the first image region Pk, for example. This determination enables mapping between the second image region Qk_n and the first image region Pk.

<3D Model Generator 16>

The 3D model generator 16 generates a 3D model of a blood vessel in accordance with information determined by the corresponding region determiner 15.

If the corresponding region determiner 15 determines a second region corresponding to the first region, the 3D model generator 16 can specify a 3D position of the point Jk on the blood vessel 1201 in accordance with the triangulation principle. Similarly, the 3D model generator 16 can generate a 3D model of the blood vessel 1201 by specifying in 3D position a plurality of points on the blood vessel 1201. More specifically, the corresponding region determiner 15 determines the second image region Qk_2 corresponding to the first image region Pk, so that the 3D model generator 16 can specify the 3D position of the point Jk on the blood vessel 1201 in FIG. 1.

<Operation of Apparatus>

Figure 11:
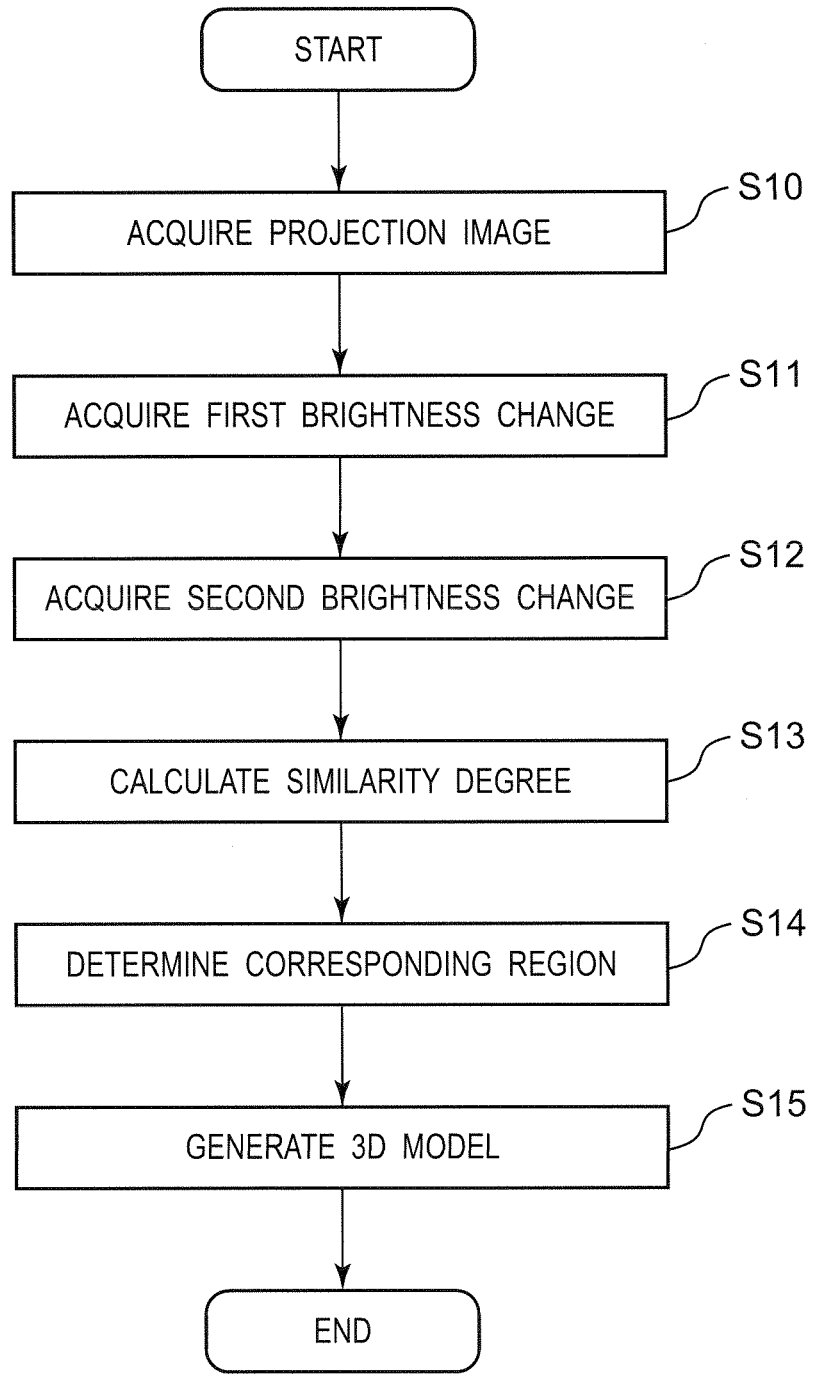
FIG. 11 is an exemplary flowchart of the processes of the 3D model generating apparatus according to the first embodiment.

FIG. 11 shows a flow of the processes of the image region mapping device 9 and the 3D model generating apparatus 10 according to the first embodiment.

Initially, the projection image acquiring unit 11 captures the blood vessel 1201 through which the contrast medium is passing, serially at the first and second photographing angles to acquire a plurality of image sets each including the first X-ray image 1101 captured at the first photographing angle and the second X-ray image 1102 captured at the second photographing angle (step S10).

The first brightness change acquiring unit 12 subsequently acquires brightness change information on the contrast medium for the predetermined time period in the first image region Pk at the predetermined portion after the bifurcation of the blood vessel 1201 on the first X-ray image 1101 acquired by the projection image acquiring unit 11 (step S11).

The second brightness change acquiring unit 13 then acquires brightness change information on the contrast medium for the predetermined time period for each of the second image regions Qk_n (n=1, 2, . . . , N) that are the regions at the predetermined portion after the bifurcation of the blood vessel 1201 on the second X-ray image 1102 acquired by the projection image acquiring unit 11, as candidate image regions corresponding to the first image region Pk (step S12). Steps S11 and S12 can be executed simultaneously.

The similarity degree calculator 14 then calculates a similarity degree between the brightness change information acquired by the first brightness change acquiring unit 12 and each of the brightness change information pieces acquired by the second brightness change acquiring unit 13 (step S13). The corresponding region determiner 15 thereafter determines, as a region corresponding to the first image region Pk, the second image region Qk_n having the highest similarity degree out of the plurality of similarity degrees calculated by the similarity degree calculator 14 (step S14). This is the end of the processes executed by the image region mapping device 9.

The 3D model generator 16 subsequently generates a 3D model of the blood vessel 1201 in accordance with the information determined by the corresponding region determiner 15 (step S15).

<Effects of the First Embodiment>

In the image region mapping device 9 according to the first embodiment, even when there is a plurality of second X-ray images 1102 for the first region on the first X-ray image 1101, the corresponding region determiner 15 can determine a correspondence relation between the first region on the first X-ray image 1101 and the second region on the most appropriate one of the second X-ray images 1102. The 3D model generating apparatus 10 can thus generate a 3D model of the blood vessel 1201 from the result of image region mapping by the image region mapping device 9.

(Second Embodiment)

In a 3D model generating apparatus 20 including an image region mapping device 92 according to the second embodiment of the present disclosure, the similarity degree calculator 14 is configured to calculate a similarity degree even when the maximum value of brightness acquired by the first brightness change acquiring unit 12 does not match the maximum value of brightness acquired by the second brightness change acquiring unit 13. The configurations similar to those of the other embodiments are denoted by the same reference numerals and will not be described repeatedly where appropriate.

Figure 12:
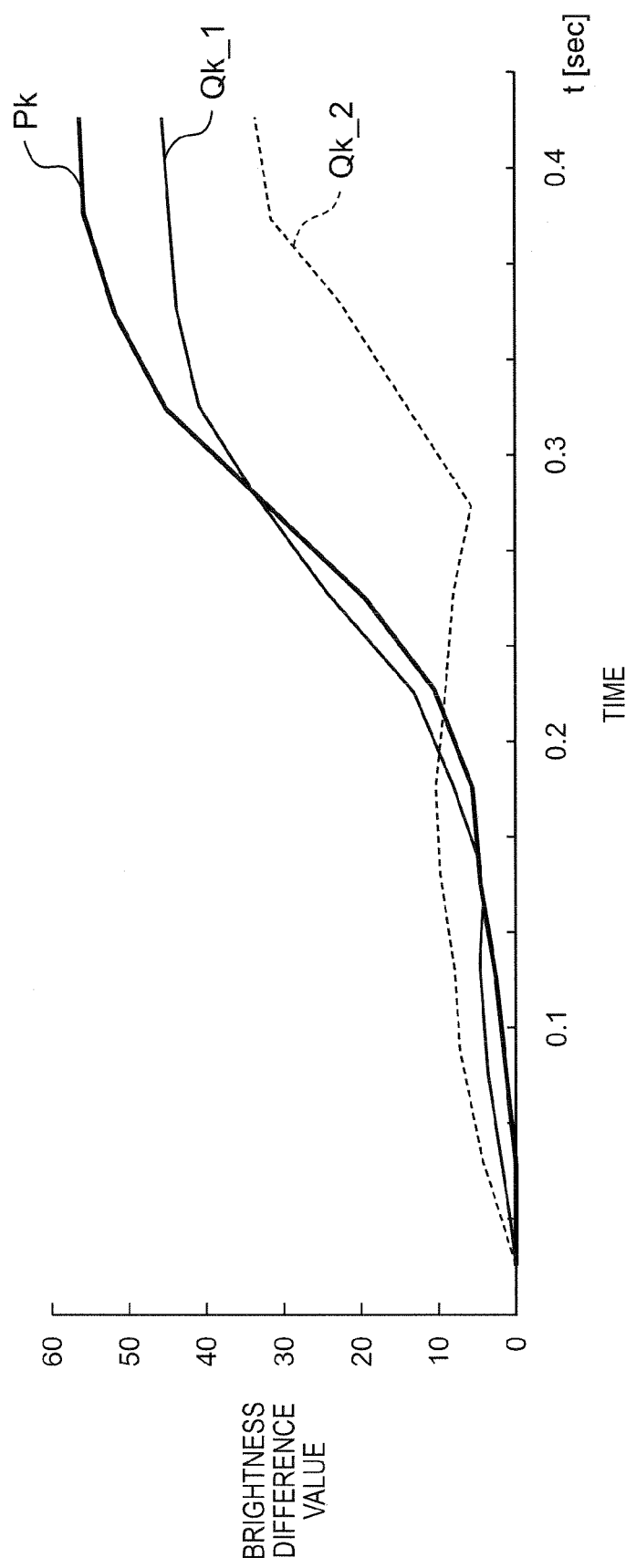
FIG. 12 is a graph of brightness changes acquired by the first and second brightness change acquiring units.

FIG. 12 is a graph of brightness change information acquired by each of the first and second brightness change acquiring units 12 and 13.

The brightness of the first image region Pk acquired by the first brightness change acquiring unit 12 is indicated by a thick line in FIG. 12. The brightness of the second image region Qk_1 acquired by the second brightness change acquiring unit 13 is indicated by a thin line. The brightness of the second image region Qk_2 acquired by the second brightness change acquiring unit 13 is indicated by a dotted line. The maximum values of the brightness differences do not match in these three indications in FIG. 12. This means that the brightness maximum value of the second image region Qk_1 or Qk_2 corresponding to the first image region Pk is different from the brightness maximum value of the first image region Pk. The reason for the differences is described below with reference to FIG. 13.

Figure 13:
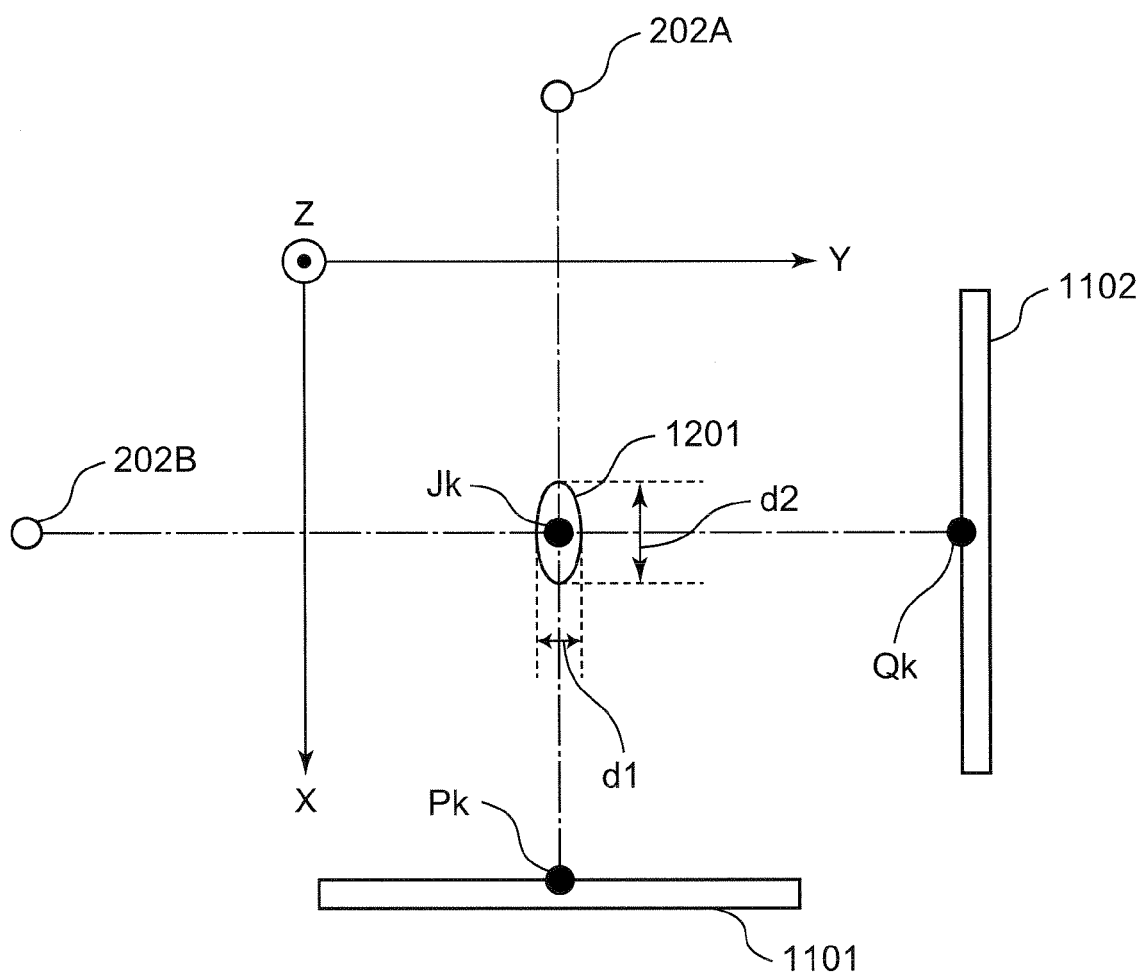
FIG. 13 is an explanatory view of a reason why brightness maximum values are different in corresponding regions.

FIG. 13 is an explanatory view of the reason why the brightness maximum values are different in the corresponding regions.

The view in FIG. 13 corresponds to the view in FIG. 1 when viewed in a Z axial direction in a case where the blood vessel 1201 has an elliptical section. When the blood vessel 1201 has an elliptical section, a thickness d1 of the blood vessel 1201 viewed in the direction of the first X-ray image 1101 is different in length from a thickness d2 of the blood vessel 1201 viewed in the direction of the second X-ray image 1102. Assume that d1 is shorter than d2.

X rays emitted from the X-ray generators 202A and 202B decrease in transmission amount as the blood vessel 1201 increases in thickness. When X-rays emitted from the X-ray generators 202A and 202B are equal in intensity in FIG. 13, the first X-ray image 1101 is lower in brightness than the second X-ray image 1102.

The brightness maximum value of the first image region Pk does not match the brightness maximum value of the second image region Qk corresponding to the first image region Pk.

In view of the above circumstances, an object of the second embodiment is to enable a similarity degree calculator 22 to accurately calculate a similarity degree even when the blood vessel 1201 has an elliptical section.

<Configuration of Apparatus>

Figure 14:
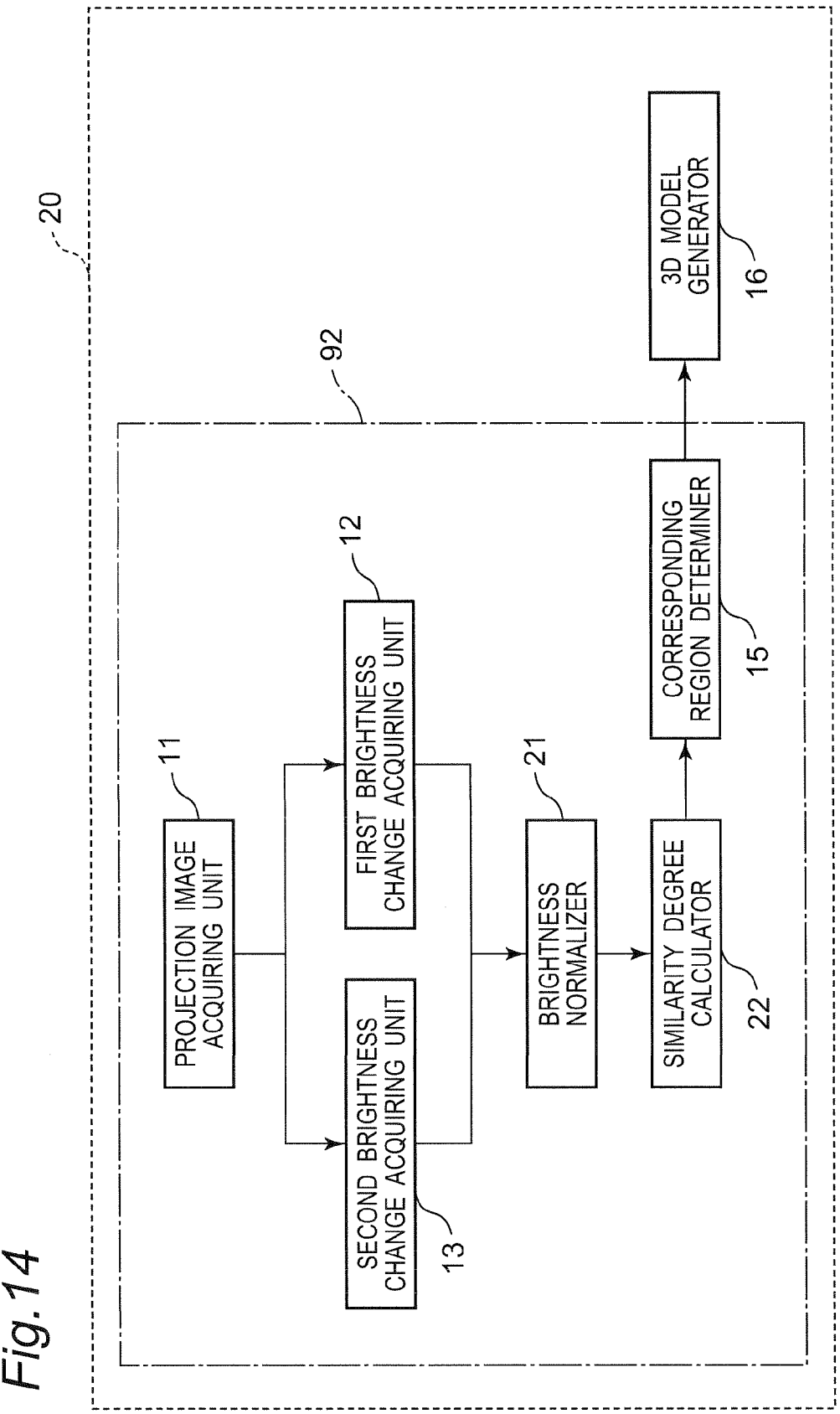
FIG. 14 is a block diagram of the functional configuration of a 3D model generating apparatus according to a second embodiment.

FIG. 14 is a functional block diagram of the 3D model generating apparatus 20 including the image region mapping device 92 according to the second embodiment of the present disclosure.

The 3D model generating apparatus 20 includes the image region mapping device 92 and the 3D model generator 16.

The image region mapping device 92 includes the projection image acquiring unit 11, the first brightness change acquiring unit 12, the second brightness change acquiring unit 13, a brightness normalizer (normalizing unit) 21, the similarity degree calculator 22, and the corresponding region determiner 15. The configurations similar to those of the first embodiment are denoted by the same reference numerals and will not be described repeatedly where appropriate.

<Brightness Normalizer 21>

The brightness normalizer 21 normalizes with calculation of a difference value by subtracting brightness acquired by the first brightness change acquiring unit 12 from the reference brightness (e.g. 255) for the case where the blood vessel is not captured. Similarly, the brightness normalizer 21 normalizes with calculation of a difference value by subtracting each brightness acquired by the second brightness change acquiring unit 13 from the reference brightness (e.g. 255) for the case where the blood vessel is not captured.

More specifically, the brightness normalizer 21 initially determines the maximum brightness, such as the reference brightness for the case where the blood vessel 1201 is not captured, from the brightness for the predetermined time period of the first image region Pk acquired by the first brightness change acquiring unit 12. The brightness normalizer 21 subsequently normalizes with calculation of a difference value by subtracting brightness of the first image region Pk at each time from the reference brightness. Similarly, the brightness normalizer 21 determines the maximum brightness, such as the reference brightness for the case where the blood vessel 1201 is not captured, for each of the second image regions Qk_1 and Qk_2 acquired by the second brightness change acquiring unit 13, and then normalizes in accordance with the reference brightness thus determined.

Figure 15:
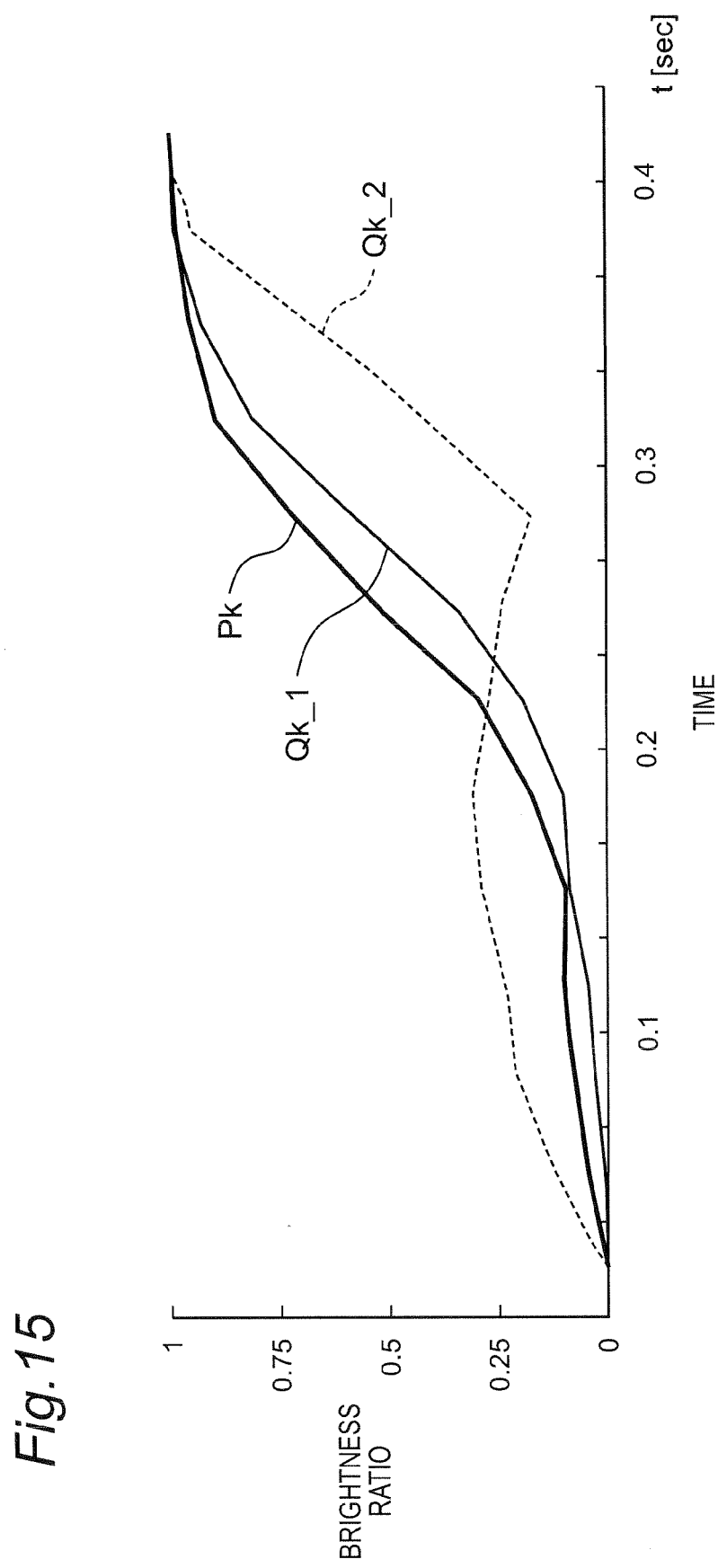
FIG. 15 is a graph of normalized brightness changes.

FIG. 15 is an exemplary graph of normalized brightness change information.

The normalized indications in FIG. 15 are obtained when the brightness normalizer 21 normalizes the indications in FIG. 12. The ordinate axis indicates a brightness ratio and the transverse axis indicates time. As indicated in FIG. 15, normalization matches the maximum values on the ordinate axis (the brightness ratio of 1 in this case) of the three indications of the brightness for the predetermined time period of the first image region Pk, the brightness for the predetermined time period of the second image region Qk_1, and the brightness for the predetermined time period of the second image region Qk_2. The brightness normalizer 21 can thus compare to find which one of the brightness change information pieces on the second image regions Qk_1 and Qk_2 is similar to the brightness change information on the first image region Pk.

<Similarity Degree Calculator 22>

The similarity degree calculator 22 calculates a similarity degree between the brightness change information acquired by the first brightness change acquiring unit 12 and normalized by the brightness normalizer 21 and each of the brightness change information pieces acquired by the second brightness change acquiring unit 13 and normalized by the brightness normalizer 21.

Figure 16:
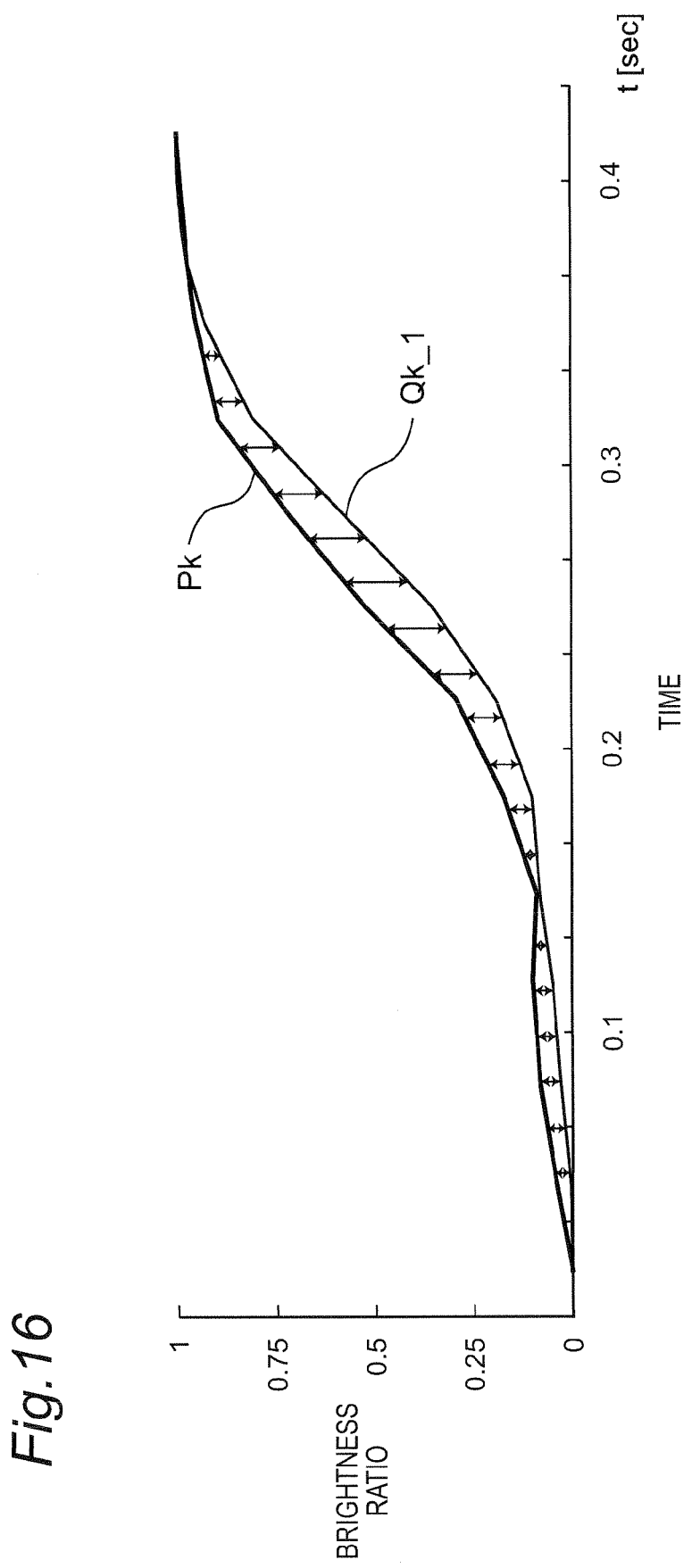
FIG. 16 is an exemplary graph of normalized brightness changes for a predetermined time period in the first image region and a first one of the second image regions.
Figure 17:
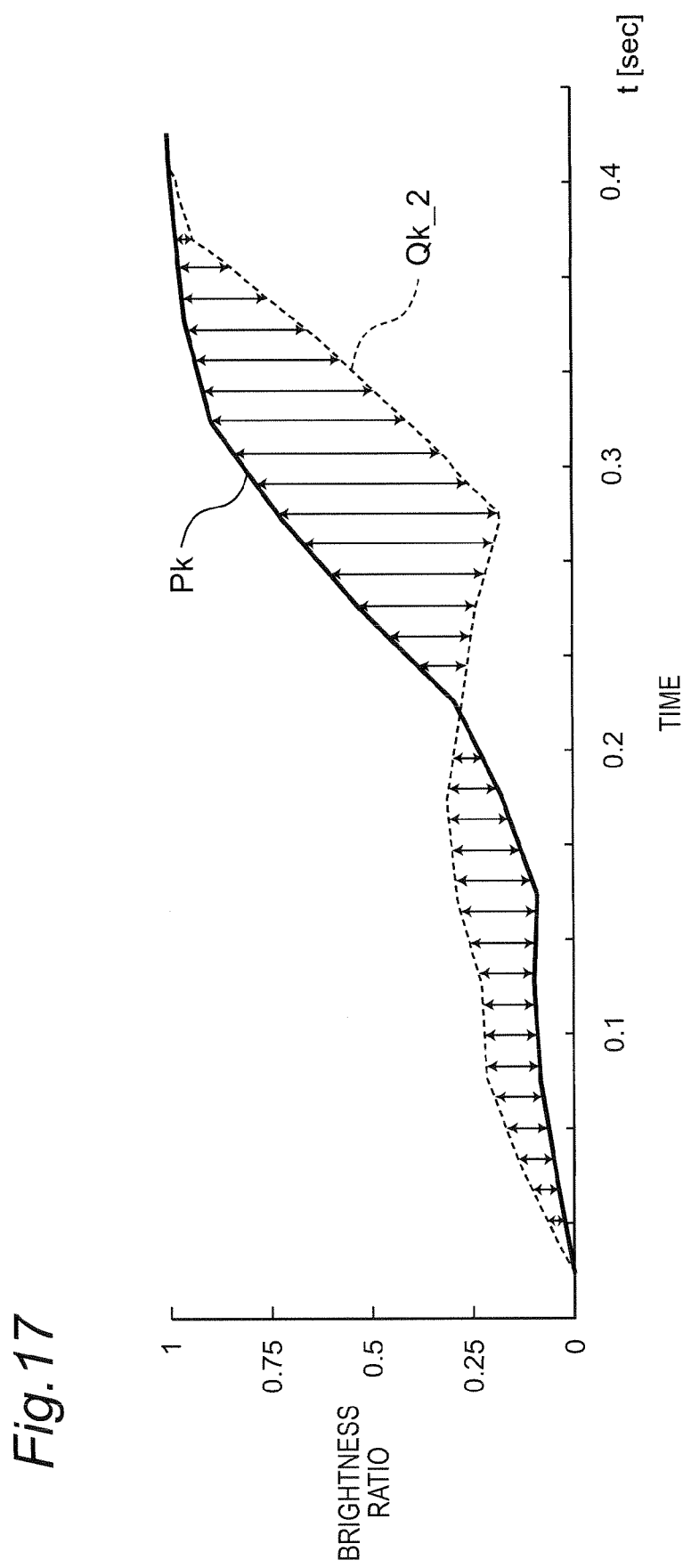
FIG. 17 is an exemplary graph of normalized brightness changes for the predetermined time period in the first image region and a second one of the second image regions.

Described below with reference to FIGS. 16 and 17 is an exemplary method of calculating a similarity degree by the similarity degree calculator 22.

FIG. 16 is a graph of normalized brightness changes for the predetermined time period of the first image region Pk and the second image region Qk_1. In FIG. 16, the brightness change of the first image region Pk is indicated by a thick line whereas the brightness change of the second image region Qk_1 is indicated by a thin line.

As indicated in FIG. 16, the similarity degree calculator 22 calculates a brightness difference at each time for the first image region Pk and the second image region Qk_1 and calculates the sum of the differences for the predetermined time period. More specifically, the similarity degree calculator 22 calculates, as a similarity degree, the sum of the absolute values of the differences in accordance with Equation 4.

$$H\_n = \sum_{t=0}^{END} |L\_Pk\_t - L\_Qk\_1\_t| \quad \text{(Equation 4)}$$

In Equation 4, H_n denotes the sum of the absolute values of the differences for the predetermined time period, L_Pk_t denotes a difference value for normalized brightness of the first image region Pk at each time, and L_Qk_1_t denotes a difference value for normalized brightness of the second image region Qk_1 at each time.

FIG. 17 is a graph of normalized brightness change information for the predetermined time period on the first image region Pk and the second image region Qk_2. In FIG. 17, the brightness change information on the first image region Pk is indicated by a thick line whereas the brightness change information on the second image region Qk_2 is indicated by a dotted line.

As indicated in FIG. 17, the similarity degree calculator 22 calculates a brightness difference at each time for the first image region Pk and the second image region Qk_2 and calculates the sum of the differences for the predetermined time period. More specifically, the similarity degree calculator 22 calculates the sum of the differences in accordance with Equation 5.

$$H\_n = \sum_{t=0}^{END} |L\_Pk\_t - L\_Qk\_2\_t| \quad \text{(Equation 5)}$$

In Equation 5, H_n denotes the sum of the absolute values of the differences for the predetermined time period, L_Pk_t denotes a difference value for normalized brightness of the first image region Pk at each time, and L_Qk_2_t denotes a difference value for normalized brightness of the second image region Qk_2 at each time.

In this manner, the similarity degree calculator 22 calculates the similarity degree from the brightness difference at each time in accordance with Equations 4 and 5.

Figure 18:
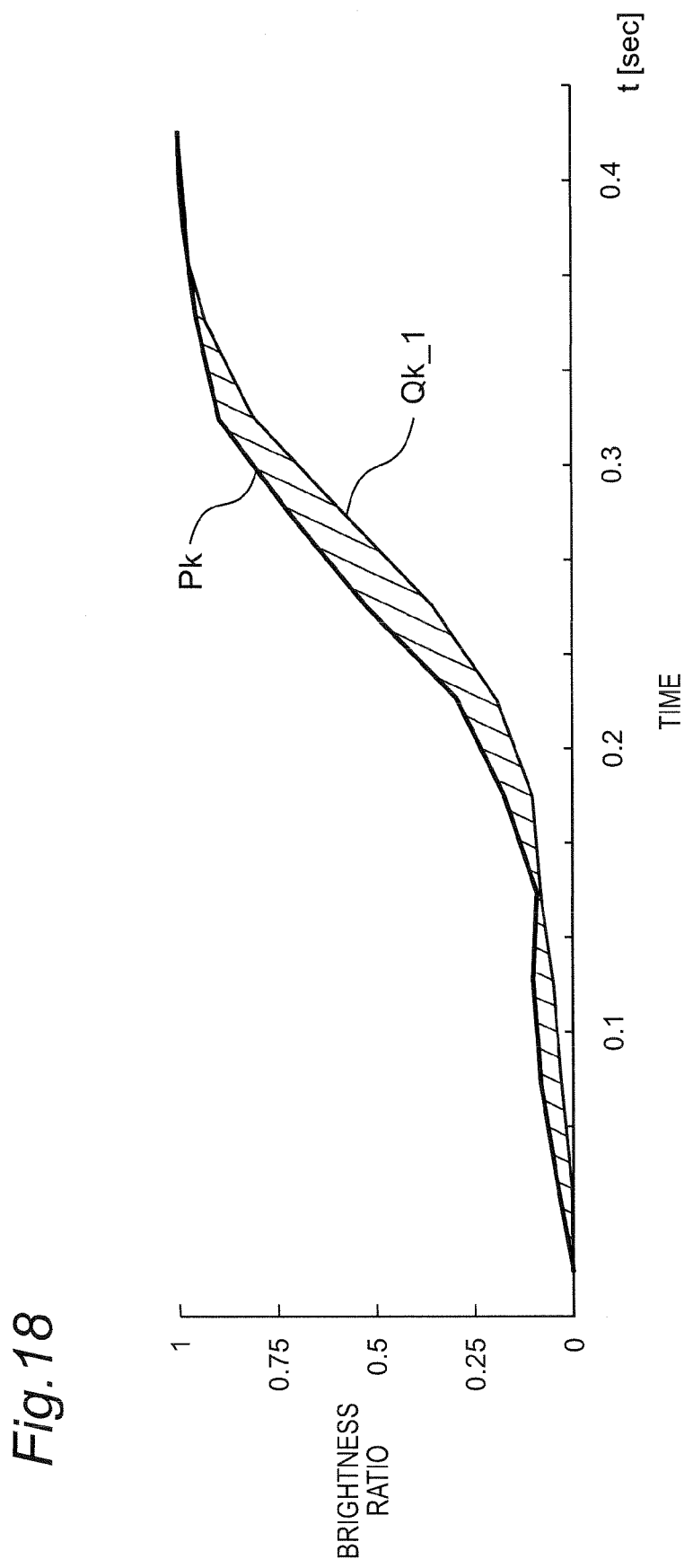
FIG. 18 is an exemplary graph of normalized brightness changes for the predetermined time period in the first image region and the first one of the second image regions.
Figure 19:
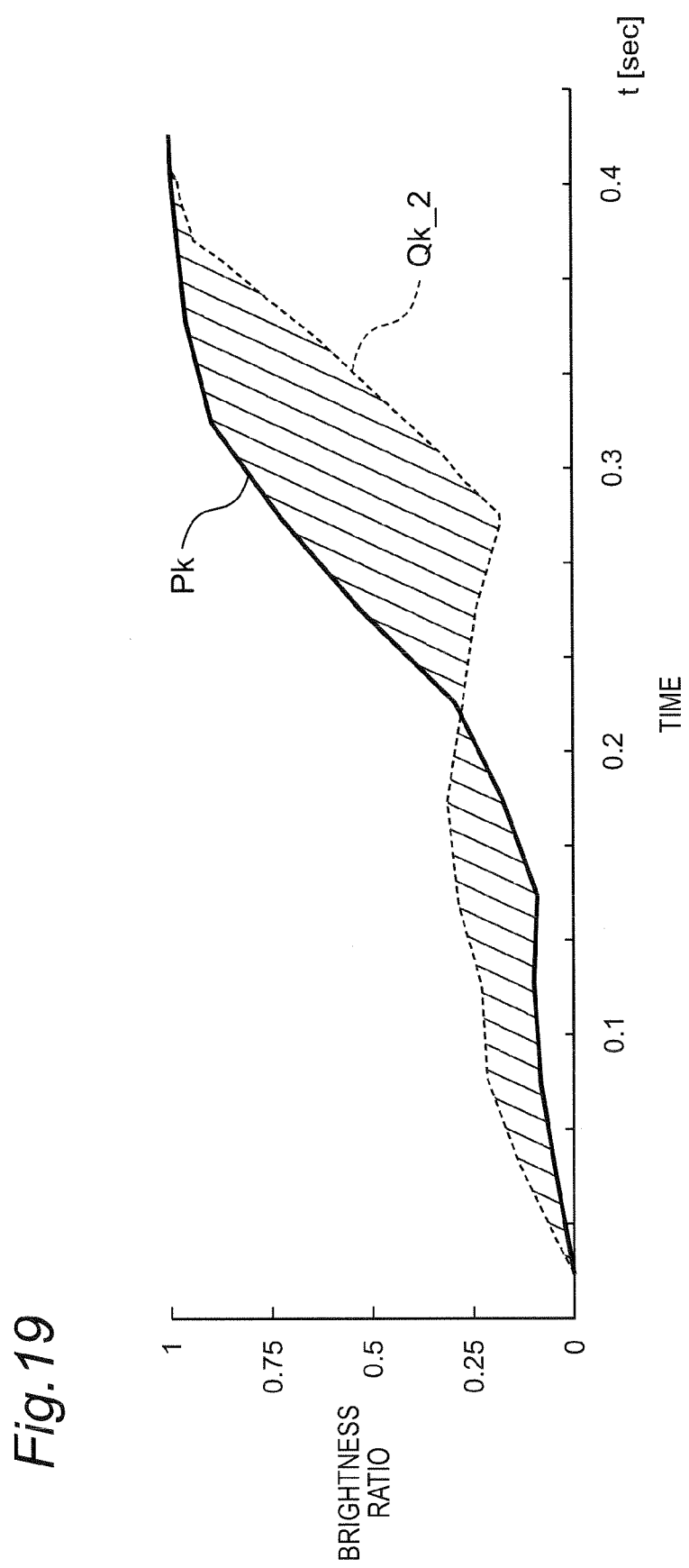
FIG. 19 is an exemplary graph of normalized brightness changes for the predetermined time period in the first image region and the second one of the second image regions.

Described below with reference to FIGS. 18 and 19 is a different exemplary method of calculating a similarity degree by the similarity degree calculator 22.

FIG. 18 is a graph of normalized brightness change information for the predetermined time period on the first image region Pk and the second image region Qk_1. In FIG. 18, the brightness change information on the first image region Pk is indicated by a thick line whereas the brightness change information on the second image region Qk_1 is indicated by a thin line.

As indicated in FIG. 18, the similarity degree calculator 22 calculates a difference in area value between the indication of the first image region Pk and the indication of the second image region Qk_1. More specifically, the similarity degree calculator 22 calculates the difference in area value in accordance with Equation 6.

$$H\_n = \int_0^{END} |S(Pk) - S(Qk\_1)| dt \quad \text{(Equation 6)}$$

In Equation 6, H_n denotes the absolute value of the difference in area value for the predetermined time period, S(Pk) denotes the area value of the first image region Pk for the predetermined time period, and S(Qk_1) denotes the area value of the second image region Qk_1 for the predetermined time period.

FIG. 19 is a graph of normalized brightness change information for the predetermined time period on the first image region Pk and the second image region Qk_2. In FIG. 19, the brightness change information on the first image region Pk is indicated by a thick line whereas the brightness change information on the second image region Qk_2 is indicated by a dotted line.

As indicated in FIG. 19, the similarity degree calculator 22 calculates a difference in area value between an area of the normalized indication of the first image region Pk and an area of the normalized indication of the second image region Qk_1. More specifically, the similarity degree calculator 22 calculates the difference in area value as a similarity degree in accordance with Equation 7.

$$H\_n = \int_0^{END} |S(Pk) - S(Qk\_2)| dt \quad \text{(Equation 7)}$$

In Equation 7, H_n denotes the absolute value of the difference in area value for the predetermined time period, S(Pk) denotes the area value of the first image region Pk for the predetermined time period, and S(Qk_2) denotes the area value of the second image region Qk_2 for the predetermined time period.

In this manner, the similarity degree calculator 22 calculates the similarity degree from the difference in area value in accordance with Equations 6 and 7.

<Operation of Apparatus>

Figure 20:
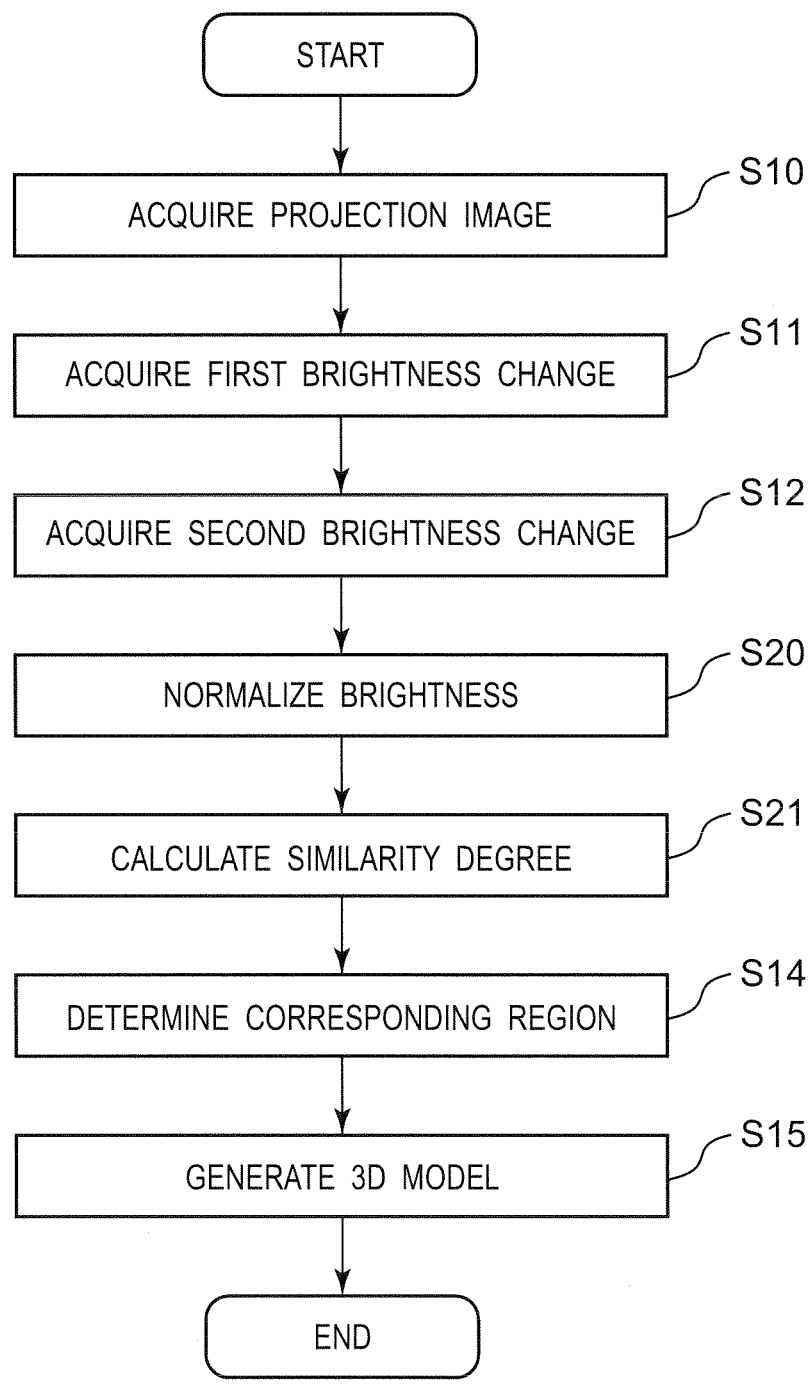
FIG. 20 is an exemplary flowchart of the processes of the 3D model generating apparatus according to the second embodiment.

FIG. 20 shows a flow of the processes of the image region mapping device 92 and the 3D model generating apparatus 20 according to the second embodiment. The steps in FIG. 20 similar to those in FIG. 11 are denoted by the same reference numerals and will not be described repeatedly where appropriate.

Steps S10 to S12 executed initially are similar to those in FIG. 11.

Subsequently, the brightness normalizer 21 normalizes brightness acquired by the first brightness change acquiring unit 12 by division by the maximum brightness (e.g. the reference brightness for the case where the blood vessel 1201 is not captured) acquired by the first brightness change acquiring unit 12. The brightness normalizer 21 normalizes each brightness acquired by the second brightness change acquiring unit 13 by division by the corresponding maximum brightness (e.g. the reference brightness for the case where the blood vessel 1201 is not captured) acquired by the second brightness change acquiring unit 13 (step S20).

The similarity degree calculator 22 then calculates a similarity degree between the brightness change information acquired by the first brightness change acquiring unit 12 and normalized by the brightness normalizer 21 and each of the brightness change information pieces acquired by the second brightness change acquiring unit 13 and normalized by the brightness normalizer 21 (step S21).

Steps S14 and S15 executed subsequently are similar to those in FIG. 11. The image region mapping device 92 ends the processes in Step S14.

<Effects of the Second Embodiment>

In the image region mapping device 92 according to the second embodiment, the similarity degree calculator 22 can accurately calculate a similarity degree even when the blood vessel 1201 has an elliptical section.

(Third Embodiment)

Different aspects of the 3D model generating apparatuses 10 and 20 according to the first and second embodiments are described in the third embodiment of the present disclosure. The configurations similar to those of the other embodiments are denoted by the same reference numerals and will not be described repeatedly where appropriate.

Figure 21:
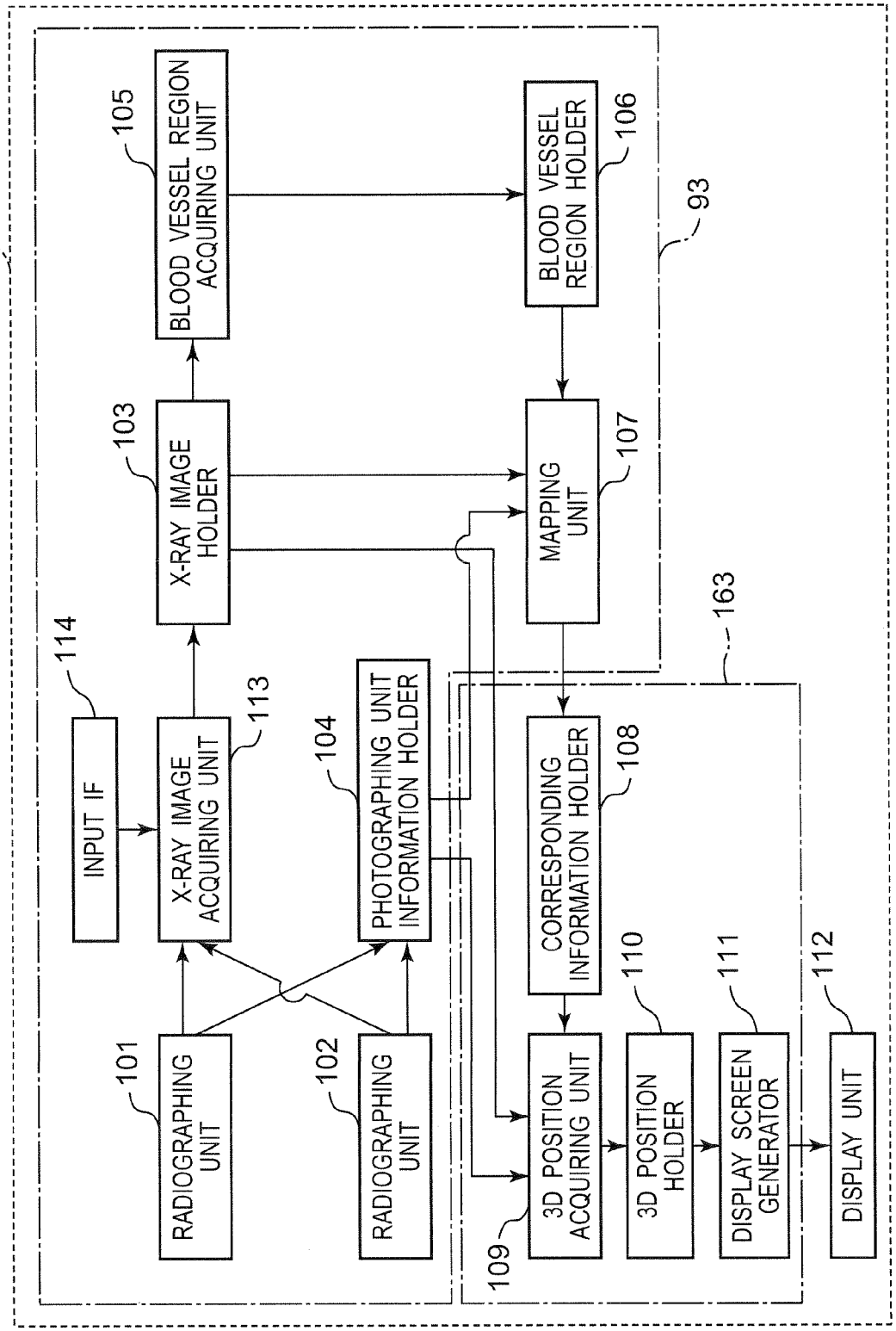
FIG. 21 is a block diagram of the functional configuration of a 3D model generating apparatus according to a third embodiment.

FIG. 21 is a view of the configuration of the 3D model generating apparatus 1 (hereinafter, also referred to as a shape restoring apparatus 1) including an image region mapping device 93 according to the third embodiment of the present disclosure. The shape restoring apparatus 1 includes the image region mapping device 93, a 3D model generator (generating unit) 163, and a display unit 112, for example.

The image region mapping device 93 includes radiographing units 101 and 102, a photographing unit information holder (holding unit) 104, an X-ray image acquiring unit 113, the input interface (IF) 114, an X-ray image holder (holding unit) 103, a blood vessel region acquiring unit 105, a blood vessel region holder (holding unit) 106, and a mapping unit 107, for example. The X-ray image acquiring unit 113 corresponds to the projection image acquiring unit 11 according to the first embodiment. The mapping unit 107 exemplarily corresponds to the first brightness change acquiring unit 12 and the second brightness change acquiring unit 13 according to the first embodiment and the similarity degree calculator 14 and the corresponding region determiner 15 according to the first embodiment.

The 3D model generator 163 includes a corresponding information holder (holding unit) 108, a 3D position acquiring unit 109, a 3D position holder (holding unit) 110, and a display screen generator (generating unit) 111.

The radiographing units 101 and 102 are each configured to capture a radioscopy image while irradiating a capture target site of a test subject with a radiation at a different angle or capture a blood vessel contrast image while injecting a contrast medium, and are called blood vessel contrast radiographing devices or angiography devices. The radiographing units 101 and 102 according to the third embodiment each capture a blood vessel as a capture target. The radiographing units 101 and 102 are configured identically, so that the configuration of the radiographing unit 101 is described below representatively.

Figure 22:
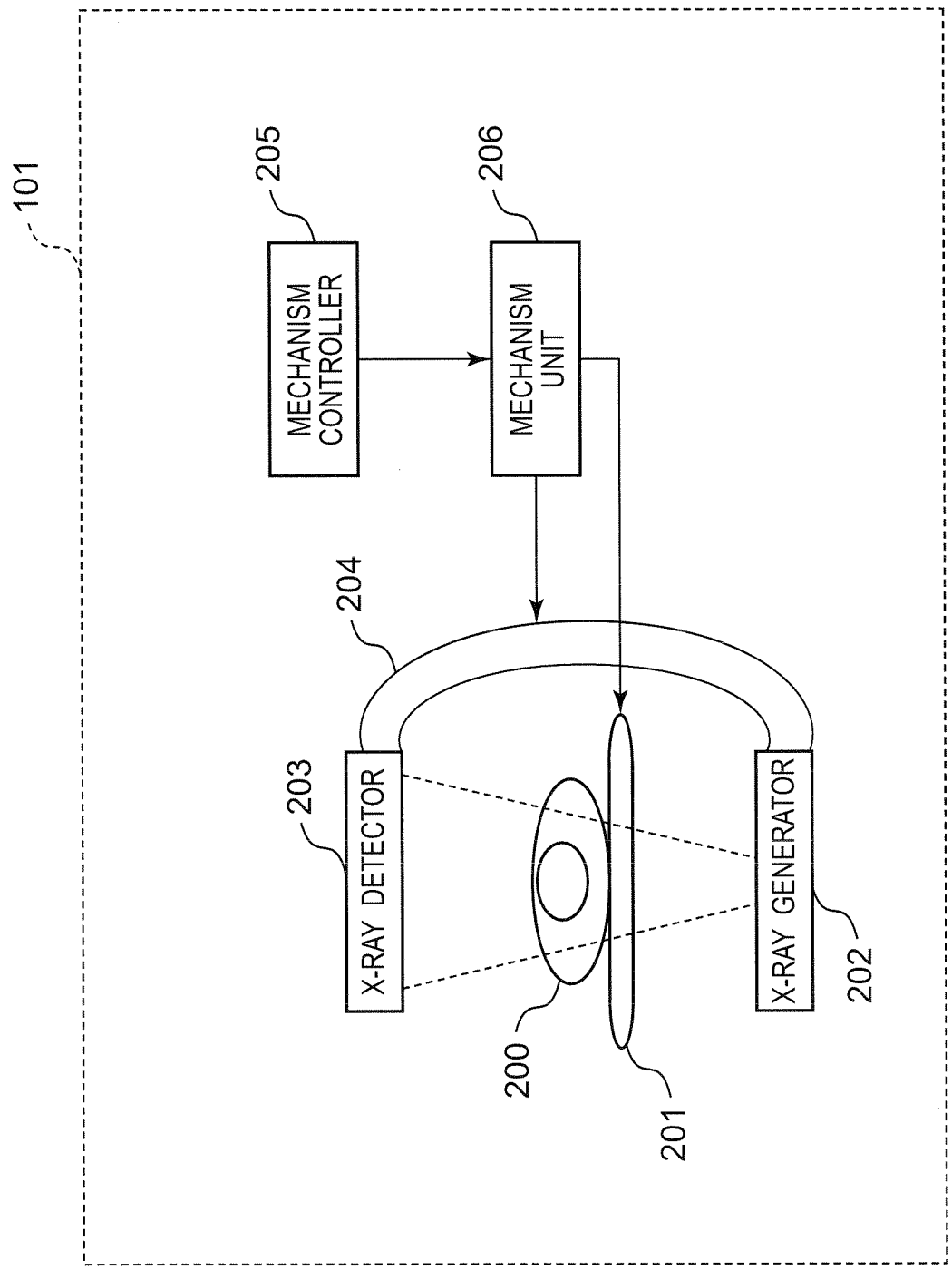
FIG. 22 is a block diagram of the configuration of a radiographing system.

FIG. 22 shows the configuration of the radiographing unit 101. The radiographing unit 101 includes the X-ray generator (generating unit) 202, an X-ray detector (detecting unit) 203, a mechanism unit 206, and a mechanism controller (controlling unit) 205.

The X-ray generator 202 has an X-ray tube configured to generate an X-ray with high voltage, and an X-ray limiter configured to partially block an X-ray to control an irradiated field, and irradiates a patient 200 on a bed 201 with an X-ray.

The X-ray detector 203 is a camera configured to record image information acquired by receiving an X-ray having transmitted through the patient 200 and output the image information thus recorded. The X-ray detector 203 is a flat panel detector (FPD) having an X-ray sensitive layer and configured to convert an X-ray to digital data and output the digital data, for example. When the X-ray generator 202 irradiates the patient 200 with an X-ray, the X-ray detector 203 transmits, to the X-ray image acquiring unit 113, image information on an irradiated X-ray image.

The mechanism unit 206 shifts an arm 204 and the bed 201 in accordance with a command of the mechanism controller 205 that has received an operation command of an operator.

The mechanism controller 205 transmits a position of the X-ray generator 202 or the X-ray detector 203 to the photographing unit information holder 104.

The radiographing unit 102 also has units similar to those of the radiographing unit 101. When distinguishing the X-ray generator 202 in the radiographing unit 101 and the X-ray generator 202 in the radiographing unit 102 in the present embodiment, the former will be called the X-ray generator 202A and the latter will be called the X-ray generator 202B.

The X-ray image acquiring unit 113 acquires an X-ray image (radiological image) from each of the radiographing units 101 and 102 and stores the acquired images in the X-ray image holder 103. The X-ray image acquiring unit 113 starts and ends image acquisition at timing commanded by the input IF 114 to be described later.

More specifically, the X-ray image acquiring unit 113 starts image acquisition in accordance with a command from the input IF 114, and stores an image acquired from the radiographing unit 101 in the X-ray image holder 103, for example. The X-ray image acquiring unit 113 then repeats acquiring an image from the radiographing unit 101 at timing commanded by the input IF 114 (e.g. at predetermined time intervals) and stores the acquired image in the X-ray image holder 103 until receiving an end command from the input IF 114. The X-ray image acquiring unit 113 similarly acquires an image from the radiographing unit 102 at timing commanded by the input IF 114 (e.g. at predetermined time intervals) and stores the acquired image in the X-ray image holder 103.

The photographing unit information holder 104 holds information on the radiographing units 101 and 102. The photographing unit information holder 104 is specifically embodied by a memory device such as a resister, a cash, a RAM, or ROM of a CPU. Hereinafter, assume that any unit named to include "holder" is embodied similarly.

The photographing unit information holder 104 specifically holds relative positional information on the radiographing units 101 and 102 and the internal parameter A of the camera in each of the radiographing units 101 and 102. FIG. 23 is an exemplary view of a data structure of the photographing unit information holder 104. The photographing unit information holder 104 holds the translation vector T, the rotation vector R, and the internal parameters A1 and A2.

The translation vector T indicates a position of the radiographing unit 102 relatively to a position of the radiographing unit 101, and exemplifies relative positional information between positional information pieces on the radiographing units 101 and 102 (positional information on a first radiographing device and positional information on a second radiographing device). The rotation vector R indicates a capture direction of the radiographing unit 102 relatively to a capture direction of the radiographing unit 101. The internal parameter A1 indicates a positional relation between an imaging lens included in the camera of the radiographing unit 101 and an imaging plane of an image sensor. The internal parameter A1 indicates a positional relation between the X-ray generator 202 and the X-ray detector 203 in the radiographing unit 101. For simplified description in the present embodiment, assume that the X-ray detector 203 is fixed in position relatively to the X-ray generator 202 and the internal parameters A1 and A2 preliminarily have values and are stored in the photographing unit information holder 104.

Also assume that the radiographing unit 102 is constantly fixed relatively to the radiographing unit 101 and the photographing unit information holder 104 preliminarily holds the translation vector T and the rotation vector R. The photographing unit information holder 104 can be alternatively configured to acquire positions of the radiographing units 101 and 102 and calculate a translation vector T and a rotation vector R from the acquired positions.

The input IF 114 is a device that allows an operating person (operator) to input a command to the shape restoring apparatus 1. The input IF 114 is embodied by a button, a switch, a computer keyboard, a computer mouse, or the like. The input IF 114 is used to command the X-ray image acquiring unit 113 to start and end image acquisition in the present embodiment.

The X-ray image holder 103 holds an image acquired by the X-ray image acquiring unit 113. FIG. 24 is an exemplary view of a data structure of the X-ray image holder 103. Assume that the X-ray image acquiring unit starts image acquisition at a time 0 and ends image acquisition at a time END. The X-ray image holder 103 holds images captured by the radiographing units 101 and 102 at respective times from the start to the end of image acquisition. Assume in the following description that an image captured by the radiographing unit 101 at a time n is to be called as an image 1_n and an image captured by the radiographing unit 102 at the time n is to be called as an image 2_n. Images 1_0 and 2_0 captured at the time 0 are to be called background images.

Figure 25:
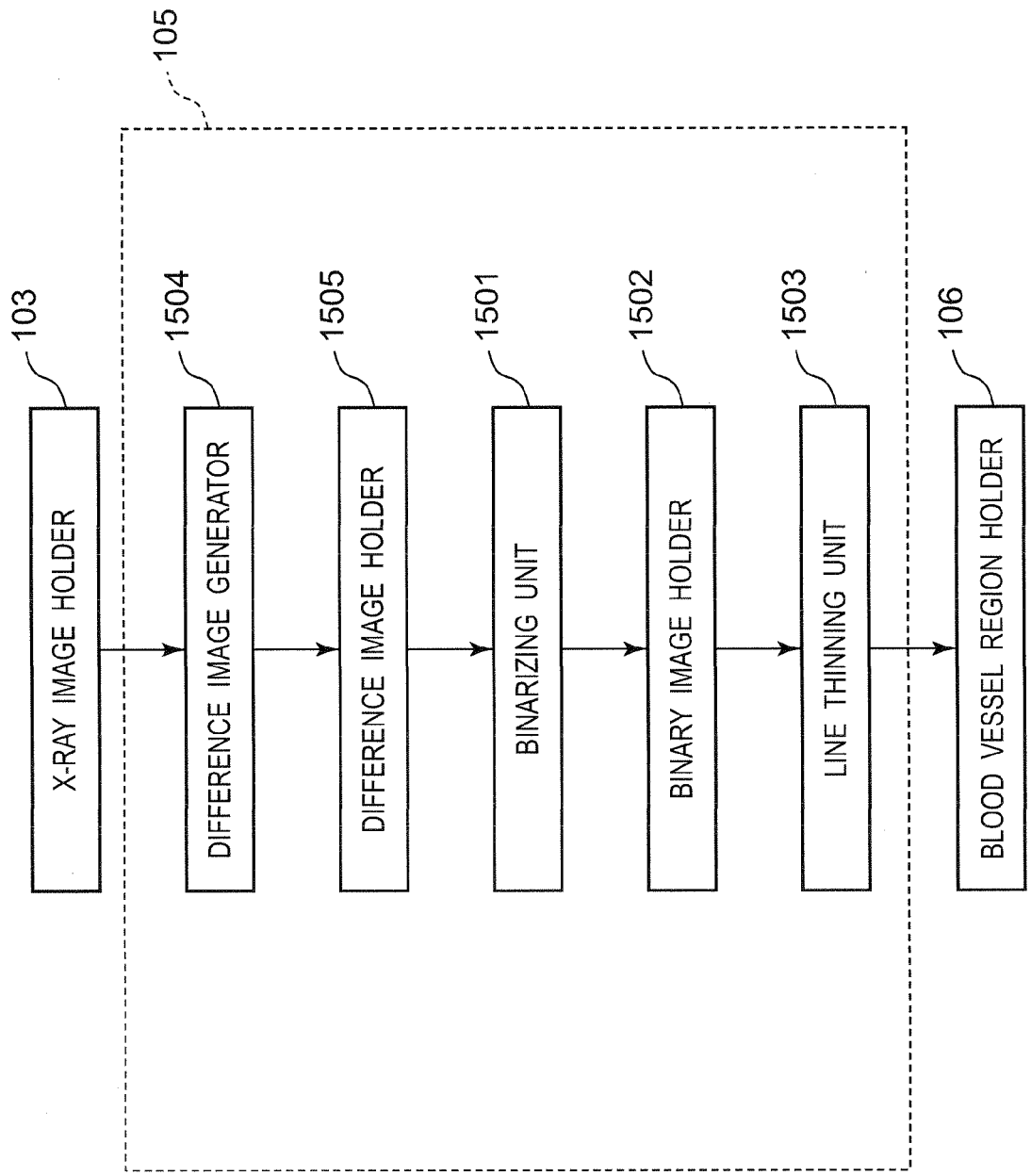
FIG. 25 is a view of the configuration of a blood vessel region acquiring unit according to the third embodiment.

The blood vessel region acquiring unit 105 acquires a region of the blood vessel 1201 into which the contrast medium is injected, from images 1_END and 2_END. A position of a point in a region acquired by the blood vessel region acquiring unit 105 corresponds to a position in the region of the blood vessel 1201. The blood vessel region acquiring unit 105 is accordingly regarded as acquiring the position of the blood vessel region. FIG. 25 is a view of the configuration of the blood vessel region acquiring unit 105. The blood vessel region acquiring unit 105 includes a difference image generator (generating unit) 1504, a difference image holder (holding unit) 1505, a binarizing unit 1501, a binary image holder (holding unit) 1502, and a line thinning unit 1503.

The difference image generator 1504 acquires an image n_END and an image n_0 (background image) from the X-ray image holder 103, generates a difference image, and stores the generated difference image in the difference image holder 1505 (n=1 and 2).

The difference image holder 1505 holds the difference image generated by the difference image generator 1504.

The binarizing unit 1501 acquires the difference image from the difference image holder 1505, binarizes the acquired difference image, and stores the binary image in the binary image holder 1502. Assume that the blood vessel region has the pixel value of "1" and the remaining region has the pixel value of "0" in the present embodiment.

Figure 26:
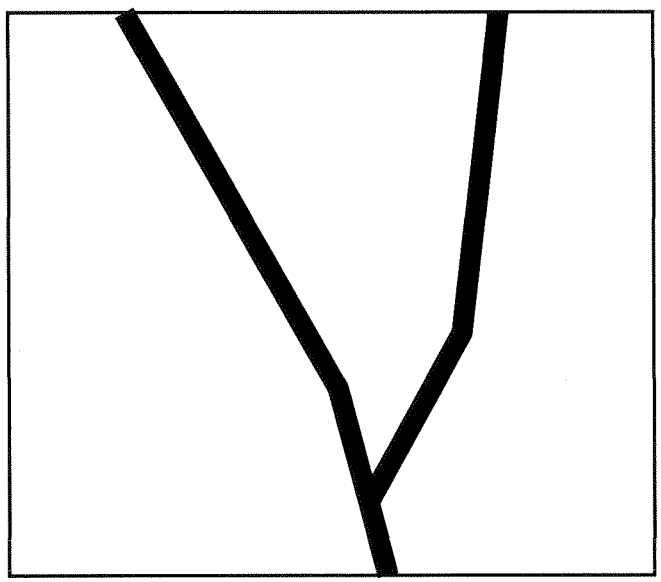
FIG. 26 is an exemplary view of a binary image according to the third embodiment.

The binary image holder 1502 holds the binary image generated by the binarizing unit 1501. FIG. 26 shows an exemplary binary image.

Figure 27:
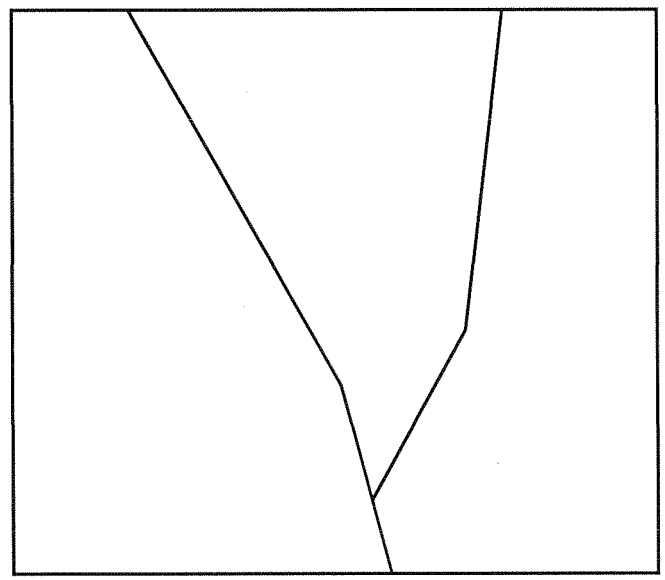
FIG. 27 is an exemplary view of a thin line image (first blood vessel region image) according to the third embodiment.

The line thinning unit 1503 thins lines in the binary image held by the binary image holder 1502 and stores the thin line image in the blood vessel region holder 106. FIG. 27 shows a thin line image obtained by thinning lines in the binary image in FIG. 26.

<Flow of Processes Executed by Blood Vessel Region Acquiring Unit 105>

Figure 28:
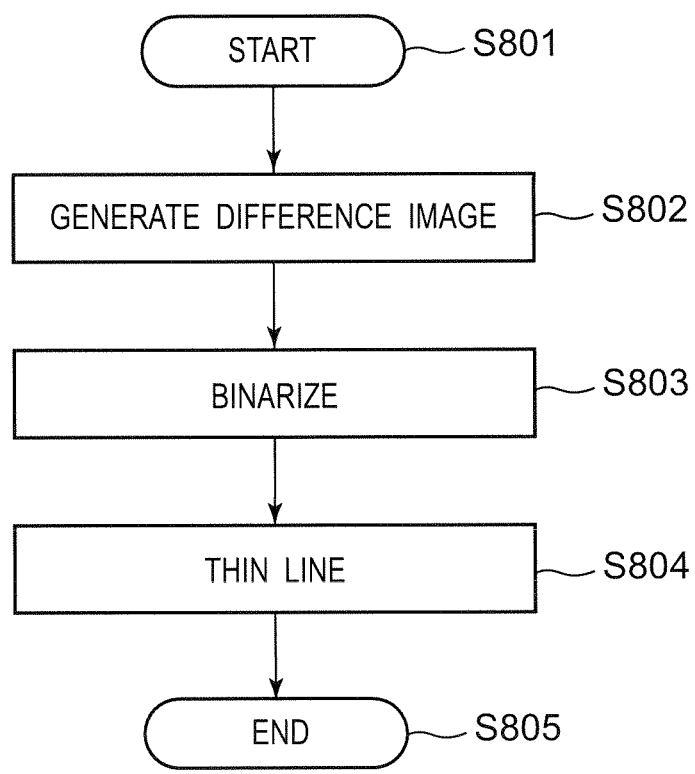
FIG. 28 is a flowchart of the blood vessel region acquiring unit according to the third embodiment.

FIG. 28 is a flowchart of the processes of the blood vessel region acquiring unit 105 that acquires a blood vessel region in the image 1_END.

The blood vessel region acquiring unit 105 starts the processes in step S801.

Subsequently in step S802, the difference image generator 1504 executes the above-described process of the difference image generator 1504. More specifically, the difference image generator 1504 acquires the images 1_0 and 1_END from the X-ray image holder 103, calculates a difference for each pixel of the acquired image to generate a difference image, and stores the generated difference image in the difference image holder 1505. A position of a point in the difference image acquired by the difference image generator 1504 corresponds to a position in the region of the blood vessel 1201. The blood vessel region acquiring unit 105 is accordingly regarded as having acquired the position of the blood vessel region.

Subsequently in step S803, the binarizing unit 1501 executes the above-described process of the binarizing unit 1501. More specifically, the binarizing unit 1501 acquires the difference image from the difference image holder 1505, binarizes the acquired difference image, and stores the binary image in the binary image holder 1502.

Subsequently in step S804, the line thinning unit 1503 executes the above-described process of the line thinning unit 1503. More specifically, the line thinning unit 1503 thins lines in the binary image held by the binary image holder 1502 and stores the thin line image in the blood vessel region holder 106. A position of a point in the thin line image acquired by the line thinning unit 1503 corresponds to a position in the region of the blood vessel 1201. The line thinning unit 1503 is accordingly regarded as having acquired the position of the blood vessel region.

The blood vessel region acquiring unit 105 then ends the processes in step S805.

The blood vessel region acquiring unit 105 similarly processes the image 2_END that is captured by the radiographing unit 102.

Figure 29:
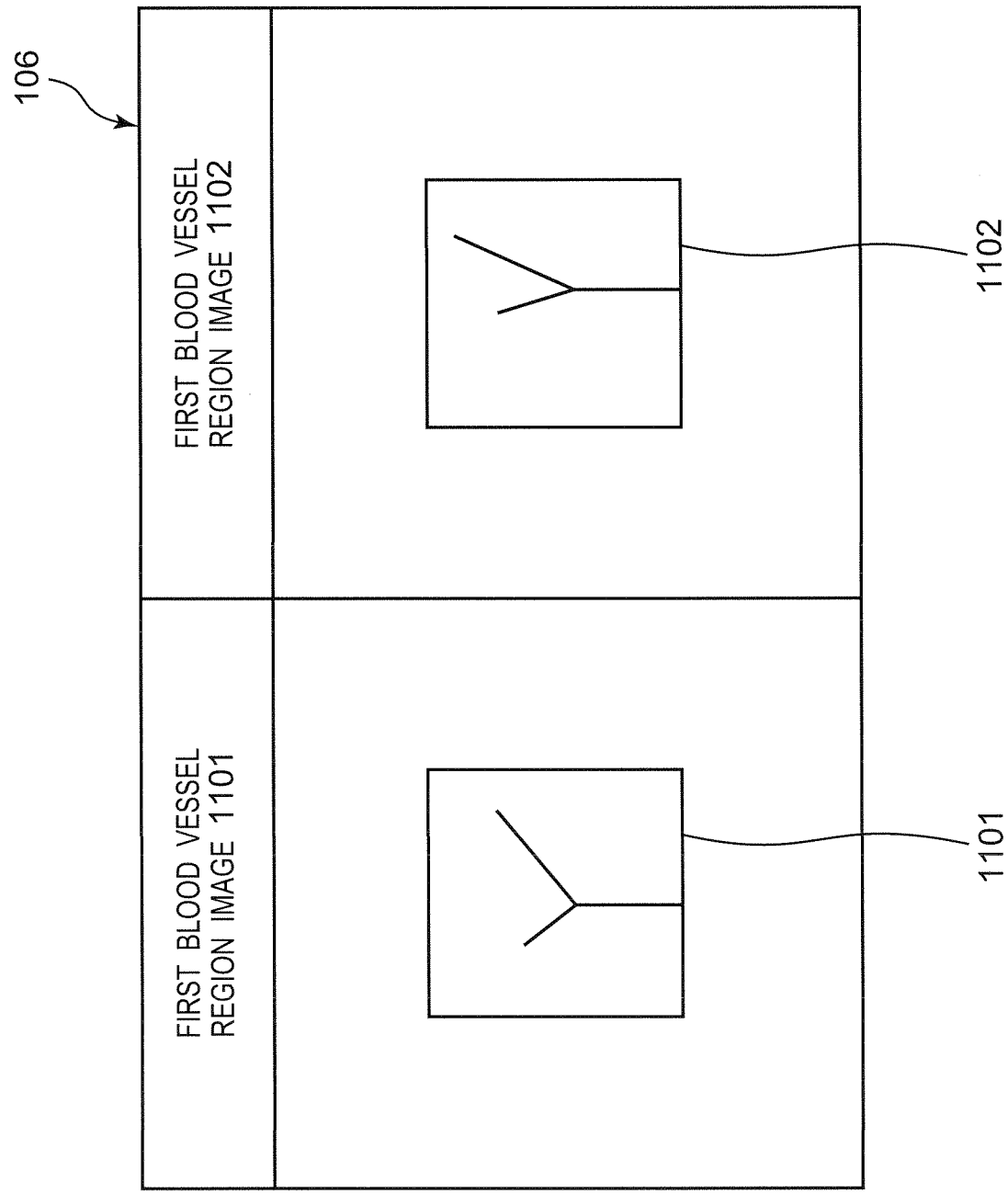
FIG. 29 is an exemplary view of a data structure of the blood vessel region holder according to the third embodiment.

The blood vessel region holder 106 holds a blood vessel region acquired by the blood vessel region acquiring unit 105. FIG. 29 is an exemplary view of a data structure of the blood vessel region holder 106. The blood vessel region holder 106 holds a first blood vessel region image 1101 generated from the image 1_END and a second blood vessel region image 1102 generated from the image 2_END.

The mapping unit 107 acquires a position of a corresponding point on the second blood vessel region image 1102 for each of contrast points Pk (k=1, 2, ..., K; where K is the number of contrast points on the first blood vessel region image 1101) on the first blood vessel region image 1101 held by the blood vessel region holder 106.

Figure 30:
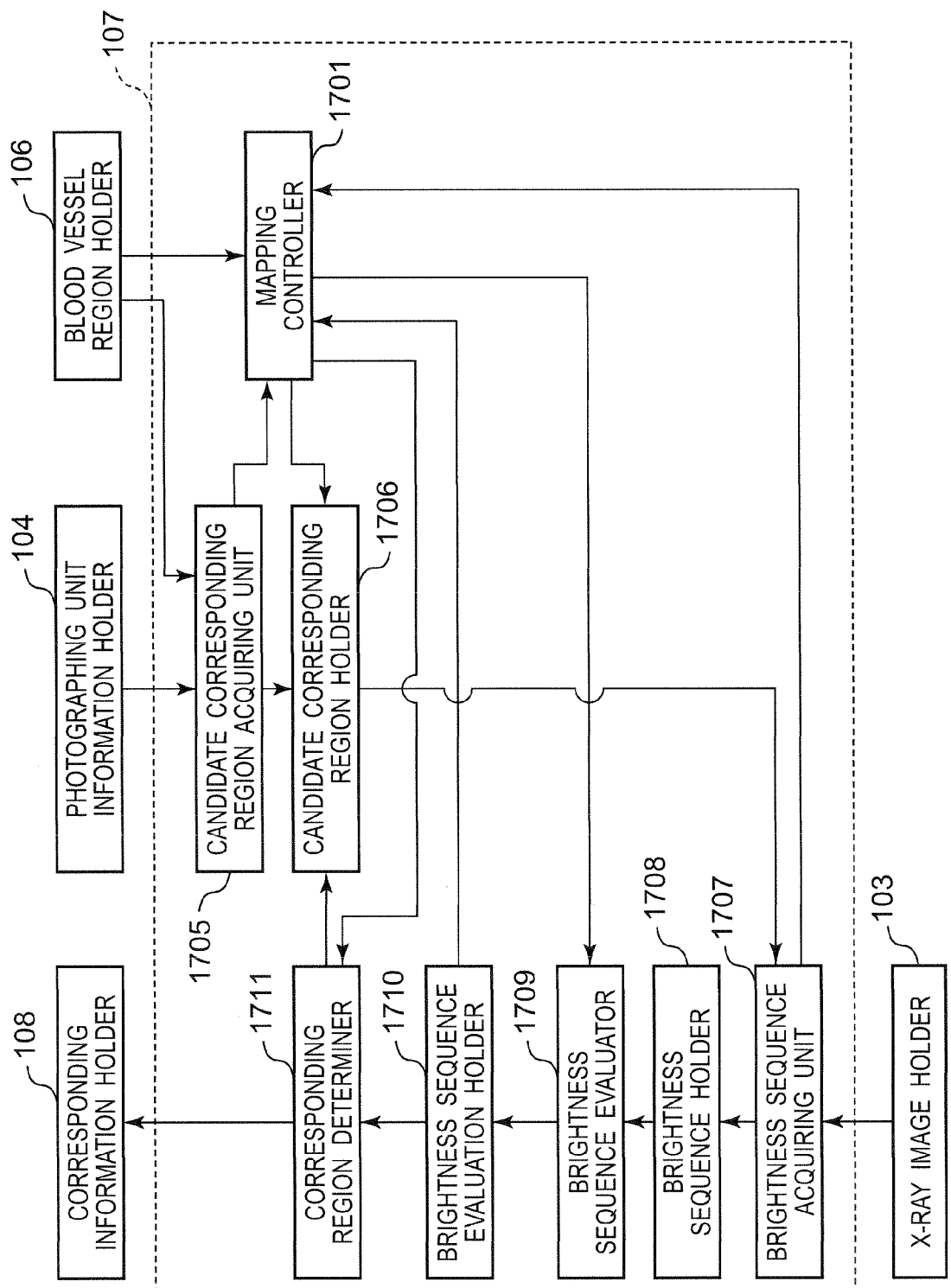
FIG. 30 is a view of the configuration of a mapping unit according to the third embodiment.

FIG. 30 is a view of the configuration of the mapping unit 107. The mapping unit 107 includes a candidate corresponding region acquiring unit 1705, a candidate corresponding region holder (holding unit) 1706, a brightness sequence acquiring unit 1707 exemplifying as the brightness change acquiring unit, a brightness sequence holder (holding unit) 1708, a brightness sequence evaluator (evaluating unit) 1709 exemplifying as the similarity degree calculator, a brightness sequence evaluation holder (holding unit) 1710, a corresponding region determiner (determining unit) 1711, and a mapping controller (controlling unit) 1701.

The candidate corresponding region acquiring unit 1705 acquires a position of each of candidate corresponding points Qk_n (n=1, 2, . . . , N; where N is the number of candidate corresponding points), as a candidate of the corresponding point, for the contrast point Pk designated by the mapping controller 1701 to be described later. In other words, the candidate corresponding region acquiring unit 1705 calculates an epipolar plane as a plane defined by the position of the contrast point Pk and positions of the radiographing unit 101 and the radiographing unit 102, from the position of the contrast point Pk and positional information on the radiographing units 101 and 102 (positional information acquired from each of the photographing unit information acquiring unit and the positional information acquiring unit), calculates an epipolar line on the second projection image, as an intersection line between the calculated epipolar plane and the second projection image, and acquires positional information on each of the plural second image regions located on the calculated epipolar line.

Figure 31:
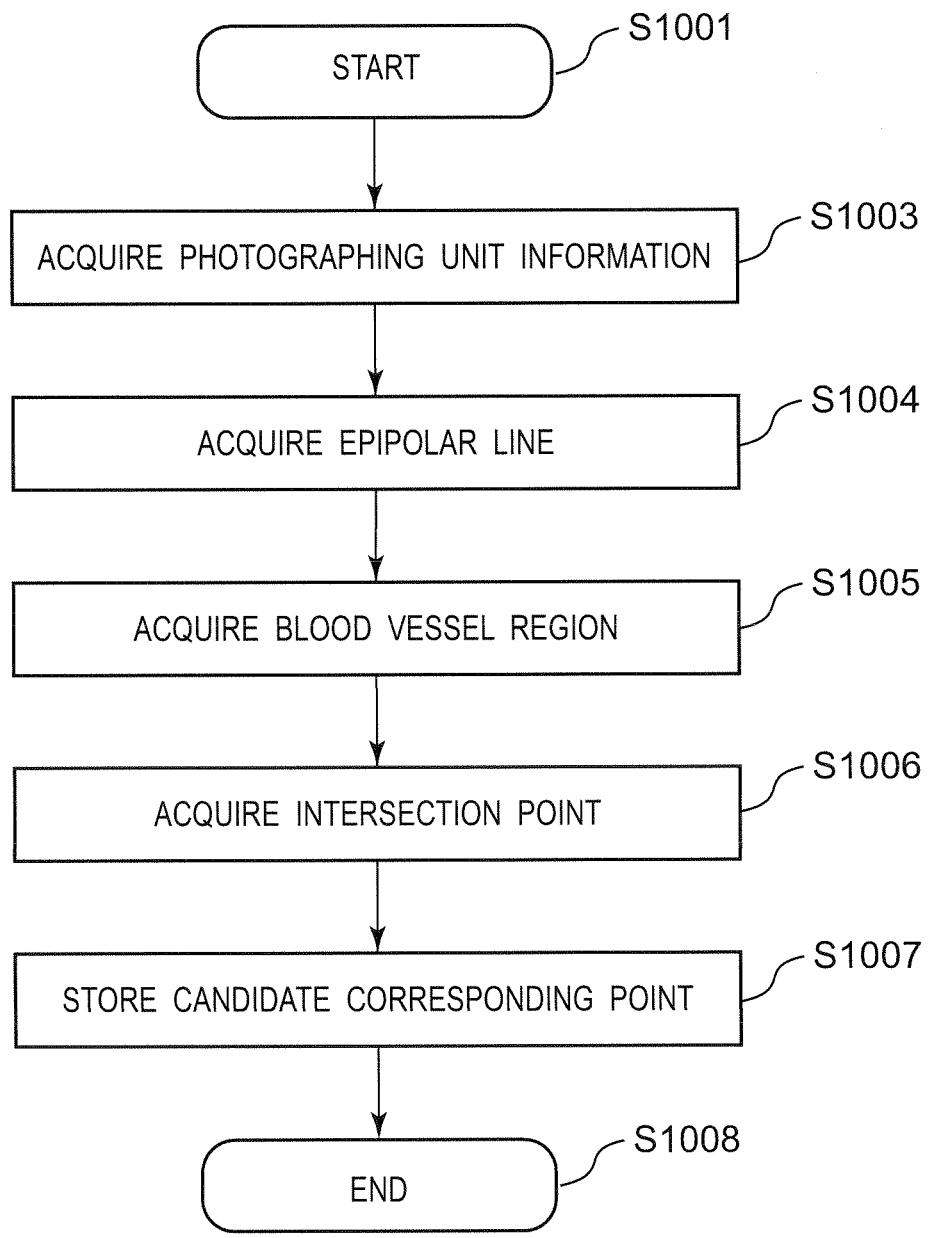
FIG. 31 is a flowchart of a candidate corresponding region acquiring unit according to the third embodiment.

A specific method is described below with reference to the flowchart in FIG. 31 of the processes executed by the blood vessel region acquiring unit 105.

The candidate corresponding region acquiring unit 1705 starts the processes in step S1001.

Subsequently in step S1003, the candidate corresponding region acquiring unit 1705 acquires the translation vector T, the rotation vector R, and the internal parameters A1 and A2 from the photographing unit information holder 104.

Then in step S1004, the candidate corresponding region acquiring unit 1705 calculates the epipolar line L2 corresponding to an acquired contrast region. The epipolar line L2 has a linear range in which the corresponding point of the contrast point Pk possibly appears on a second screen and is determined by the position of the contrast point Pk and a geometrical positional relation between the radiographing unit 101 and the radiographing unit 102. The position of the contrast point Pk corresponds to a position of a point located in the blood vessel region on the first blood vessel region image 1101. In the present embodiment, this point holds a value indicating the blood vessel 1201 on an image held by the blood vessel region holder 106.

Figure 32:
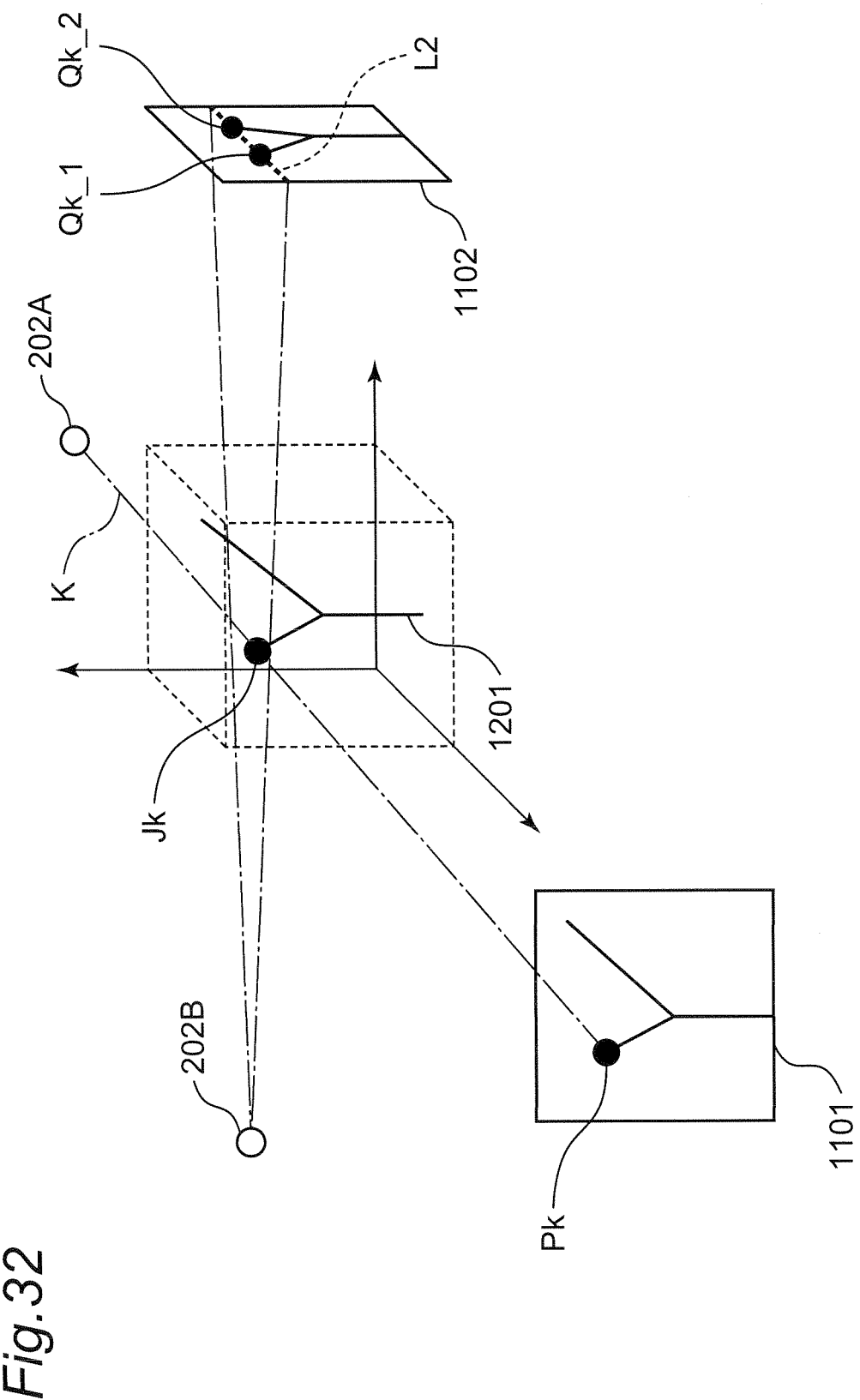
FIG. 32 is a view of an epipolar line L2 according to the third embodiment.

The epipolar line L2 is schematically described below with reference to FIG. 32. The contrast point Pk on a thin line image 1_END corresponds to a projection point of the point Jk in the 3D space (hereinafter, referred to as the 3D point Jk). FIG. 32 shows the X-ray generator 202A in the radiographing unit 101. FIG. 32 also shows the blood vessel 1201. An X-ray generated by the X-ray generator 202A passes the 3D point Jk on the blood vessel 1201, is projected at one point on an X-ray detector 203A, and is projected at the contrast point Pk on the first image.

The position of the 3D point Jk cannot be specified only from the position of the contrast point Pk on the thin line image 1_END. The 3D point Jk is assumed to be located somewhere on the straight line K that connects the X-ray generator 202A and the contrast point Pk.

The point on the straight line K is projected on a straight line on the second image 1102. The straight line on the second image is called the epipolar line. The epipolar line is denoted by reference character L2 in the present embodiment. The epipolar line L2 is a straight line where a plane including the X-ray generator 202B in the radiographing unit 102, the X-ray generator 202A, and the contrast point Pk and the image plane of the second image 1102 (or the X-ray detector 203) cross each other. The epipolar line L2 can be calculated only from relative positional information on the positions of the radiographing units 101 and 102 (the translation vector T and the rotation vector R) and information on the camera used for capture (the internal parameters A1 and A2). More specifically, the candidate corresponding region acquiring unit 1705 calculates the parameter l2 of the epipolar line L2 in accordance with Equations 8 and 9.

$$F = A1^{-T}[T]_x RA2^{-1} \quad \text{(Equation 8)}$$

$$l2 = Fm \quad \text{(Equation 9)}$$

In Equation 9, m indicates coordinates of the contrast point Pk.

In Equation 8, F denotes a matrix called a fundamental matrix, $A1^{-T}$ denotes a transpose of a transposed matrix of the internal parameter A1, and $[T]_x$ denotes a skew-symmetric matrix of the translation vector T.

Assume that the calculated parameter l2 of the epipolar line L2 is expressed by (a, b, c)T, the epipolar line L2 satisfies ax+by +c=0.

The plane including the X-ray generators 202A and 202B and the contrast point Pk is called the epipolar plane including the contrast point Pk.

Then in step S1005, the candidate corresponding region acquiring unit 1705 acquires the second blood vessel region image 1102 from the blood vessel region holder 106.

Subsequently in step S1006, the candidate corresponding region acquiring unit 1705 acquires positions of points on the epipolar line L2 on the second blood vessel region image 1102. In the following description, these points are called the candidate corresponding points Qk_n (n=1, 2, . . . , N; where N is the number of points). In the example shown in FIG. 32, the candidate corresponding region acquiring unit 1705 acquires coordinates of the candidate corresponding points Qk_1 and Qk_2.

Then in step S1007, the candidate corresponding region acquiring unit 1705 stores the positions of the candidate corresponding points Qk_n (n=1, 2, . . . , N) thus acquired, in the candidate corresponding region holder 1706.

The candidate corresponding region acquiring unit 1705 then ends the processes in step S1008.

The candidate corresponding region holder 1706 holds coordinates of the candidate corresponding points Qk_n (n=1, 2, . . . , N) acquired by the candidate corresponding region acquiring unit 1705. In the case of FIG. 32, the candidate corresponding region acquiring unit 1705 acquires coordinates of the candidate corresponding points Qk_1 and Qk_2.

The brightness sequence acquiring unit 1707 acquires brightness sequences of the designated contrast point PK and the candidate corresponding points Qk_n (n=1, 2, . . . , N) held by the candidate corresponding region holder 1706 and stores the acquired brightness sequences in the brightness sequence holder 1708.

The brightness sequence of the contrast point Pk is a number sequence indicating how brightness at the position same as the contrast point Pk changes when the contrast medium is injected into the blood vessel 1201.

For simplified description, the third embodiment refers to a case of, acquiring a sequence of a difference between brightness at a position of the contrast point Pk or the like and brightness of the background image at the position as a brightness sequence, instead of acquiring and storing a value of the brightness itself at the position of the contrast point Pk or the like. For simplification in the present embodiment, assume that the image captured at the time 0 is regarded as the background image. Alternatively, only the background image can be acquired separately.

Figure 33:
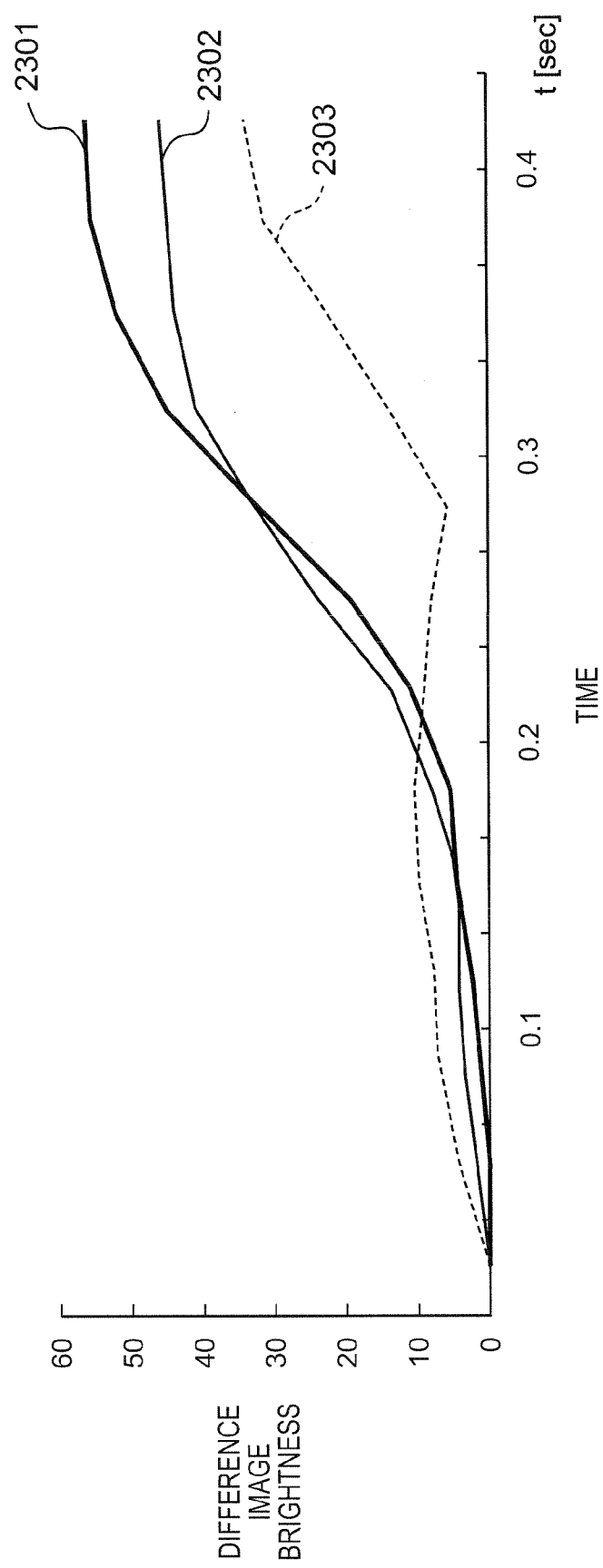
FIG. 33 is a graph indicating brightness sequences of a contrast point Pk and candidate corresponding points Qk_1 and Qk_2 according to the third embodiment.

FIG. 33 is an exemplary graph of brightness sequences acquired by the brightness sequence acquiring unit 1707. In FIG. 33, a thick line 2301, a solid line 2302, and a dotted line 2303 indicate the brightness sequence of the contrast point Pk, the brightness sequence of the candidate corresponding point Qk_1 of the contrast point Pk, and the brightness sequence of the candidate corresponding point Qk_2 thereof, respectively. The transverse axis in the graph indicates time and each scale indicates 33 msec. The ordinate axis indicates a brightness difference. This graph indicates the brightness differences at a stage where the contrast medium is injected into the blood vessel 1201 and the contrast medium in the blood vessel 1201 is increasing in concentration.

FIG. 34 is an exemplary view of a data structure of the brightness sequences held by the brightness sequence holder 1708. Data of the brightness sequences acquired by the brightness sequence acquiring unit 1707 includes brightness sequences L_Pk_t (t=0, 1, . . . , and END) of the contrast point Pk and brightness sequences L_Qk_n_t (n=1, 2, . . . , N, t=0, 1, . . . , and END) of the candidate corresponding points Qk_n.

As described earlier, the brightness sequence acquiring unit 1707 acquires the value of the brightness difference between each brightness 1_Pk_t (t=0, 1, . . . , and END) at the position of the contrast point Pk and brightness 1_Pk_0 of the background image at the position, that is, a value of L_Pk_t=1_Pk_t−1_Pk_0, and regards the value as the brightness sequence of the contrast point Pk. The brightness 1_pk_t indicates brightness at coordinates (x, y) of an image it.

The brightness sequence acquiring unit 1707 similarly acquires a brightness sequence of each of the candidate corresponding points Qk_n (n=1, 2, . . . , N) and stores the acquired brightness sequences in the brightness sequence holder 1708.

The brightness sequence holder 1708 holds the brightness sequences acquired by the brightness sequence acquiring unit 1707. The view in FIG. 34 indicates brightness sequences held by the brightness sequence holder 1708 in a case where the contrast point Pk has two candidate corresponding points Qk_n (n=1 and 2).

Figure 35:
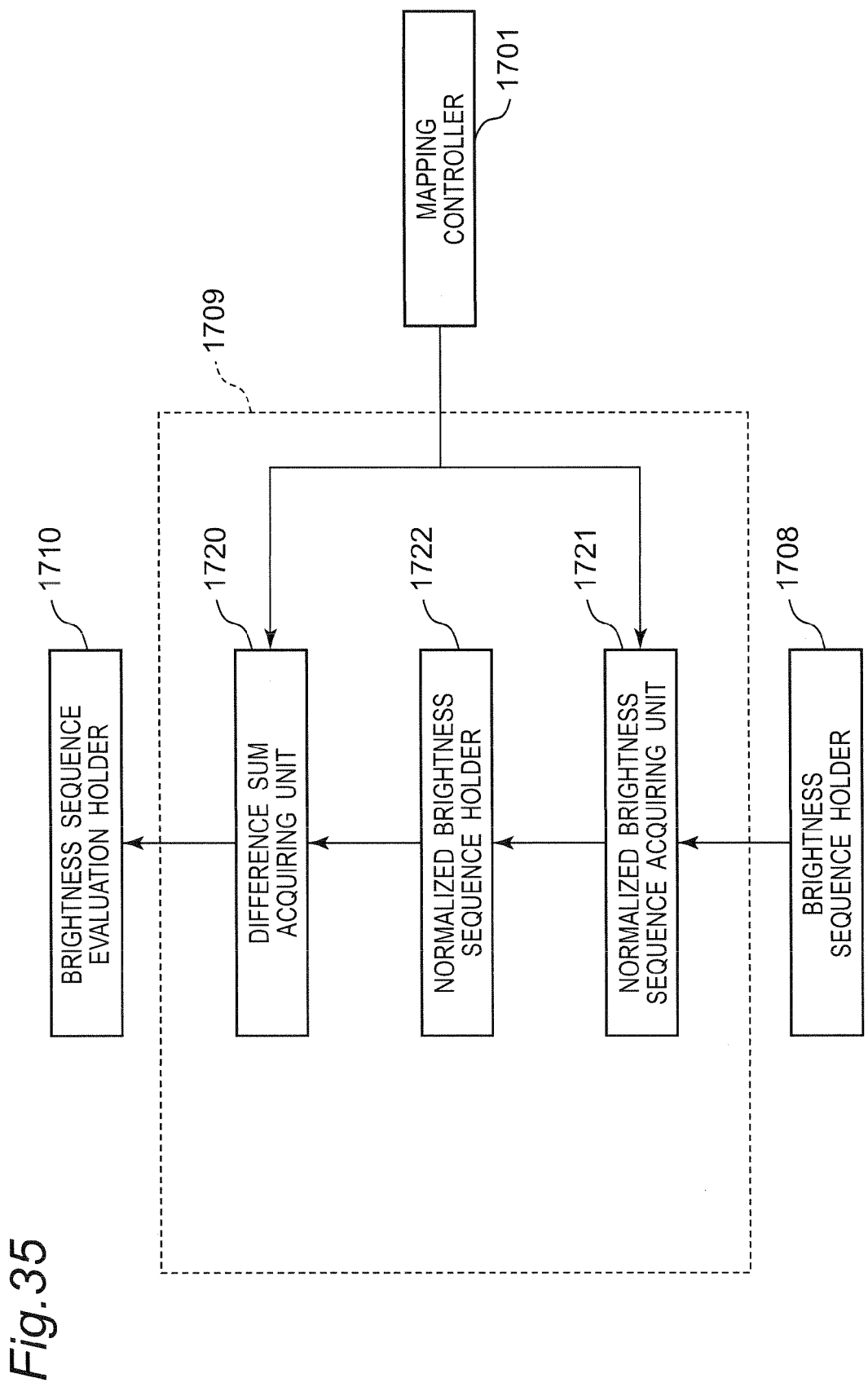
FIG. 35 is a view of the configuration of a brightness sequence evaluator according to the third embodiment.

The brightness sequence evaluator 1709 evaluates each of the candidate corresponding points Qk_n (n=1, 2, . . . , N) held by the brightness sequence holder 1708. FIG. 35 is a view of the configuration of the brightness sequence evaluator 1709.

The brightness sequence evaluator 1709 includes a normalized brightness sequence acquiring unit 1721, a normalized brightness sequence holder (holding unit) 1722, and a difference sum acquiring unit 1720.

The normalized brightness sequence acquiring unit 1721 normalizes a brightness sequence held by the brightness sequence holder 1708. In the present embodiment, the maximum value of the brightness sequences held by the brightness sequence holder 1708 is extracted, and sequences of values obtained by dividing respective values of the brightness sequences by the extracted maximum value are stored in the normalized brightness sequence holder 1722 as normalized brightness sequences.

Figure 36:
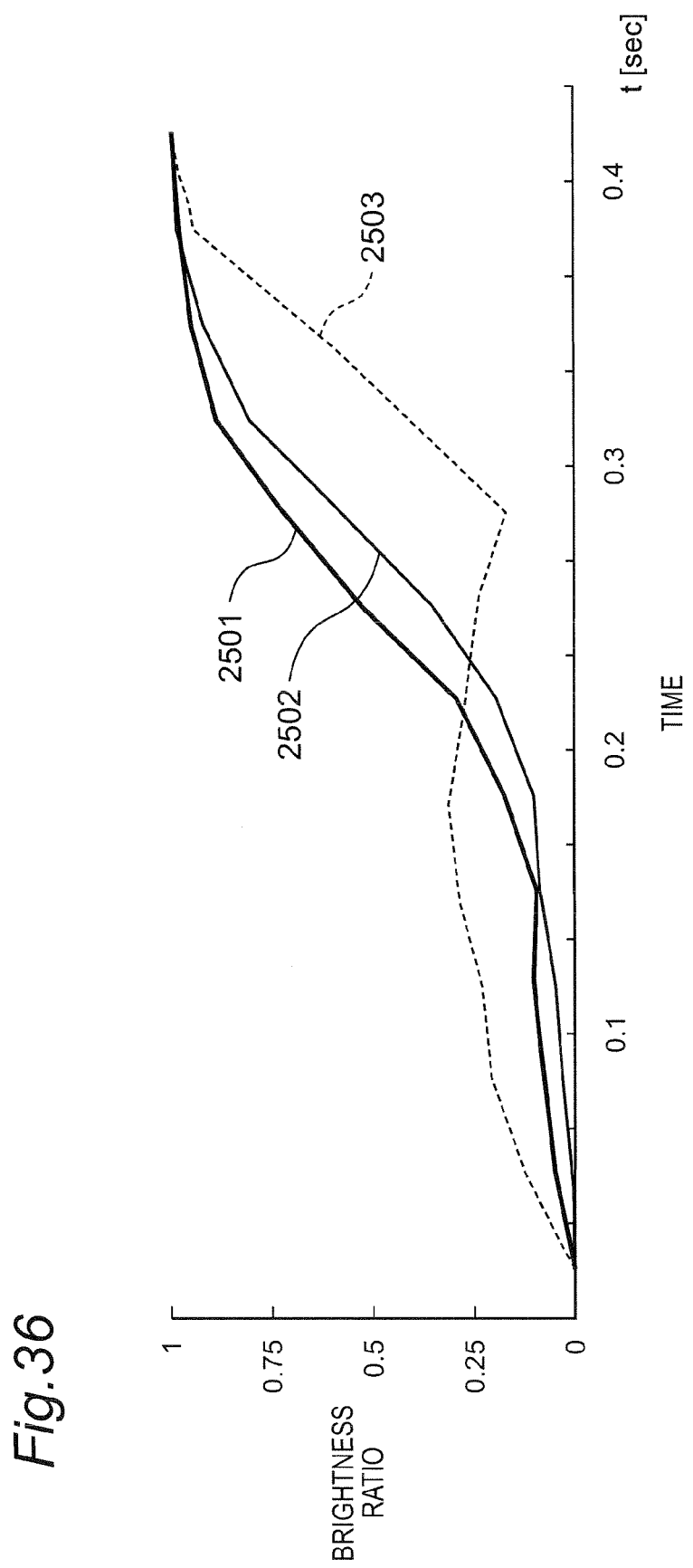
FIG. 36 is a graph indicating normalized brightness sequences of the contrast point Pk and corresponding points Qk and Qx according to the third embodiment.

FIG. 36 is a graph of normalized brightness sequences that are obtained by normalizing the brightness sequences indicated in FIG. 33. In FIG. 36, a thick line 2501, a solid line 2502, and a dotted line 2503 indicate a normalized brightness sequence of the contrast point Pk, a normalized brightness sequence of the candidate corresponding point Qk_1, and a normalized brightness sequence of the candidate corresponding point Qk_2, respectively.

The normalized brightness sequence holder 1722 stores the normalized brightness sequences generated by the normalized brightness sequence acquiring unit 1721.

The difference sum acquiring unit 1720 calculates evaluation values H_n (n=1, 2, . . . , N) indicating whether the normalized brightness sequences of the candidate corresponding points Qk_n (n=1, 2, . . . , N) held by the normalized brightness sequence holder 1722 each have a brightness change similar to or different from that of the normalized brightness sequence of the contrast point Pk, and stores the evaluation values in the brightness sequence evaluation holder 1710. The evaluation is executed in accordance with Equation 10 in the third embodiment.

$$H\_n = \sum_{t=0}^{END} |L\_Pk\_t - L\_Qk\_n\_t| \qquad \text{(Equation 10)}$$

In Equation 10, |X| indicates the absolute value of X. The evaluation value H_n according to the third embodiment is the sum of the absolute values of the differences between the normalized brightness of the contrast point Pk and the normalized brightness of the candidate corresponding point Qk_n at respective times.

Figure 37:
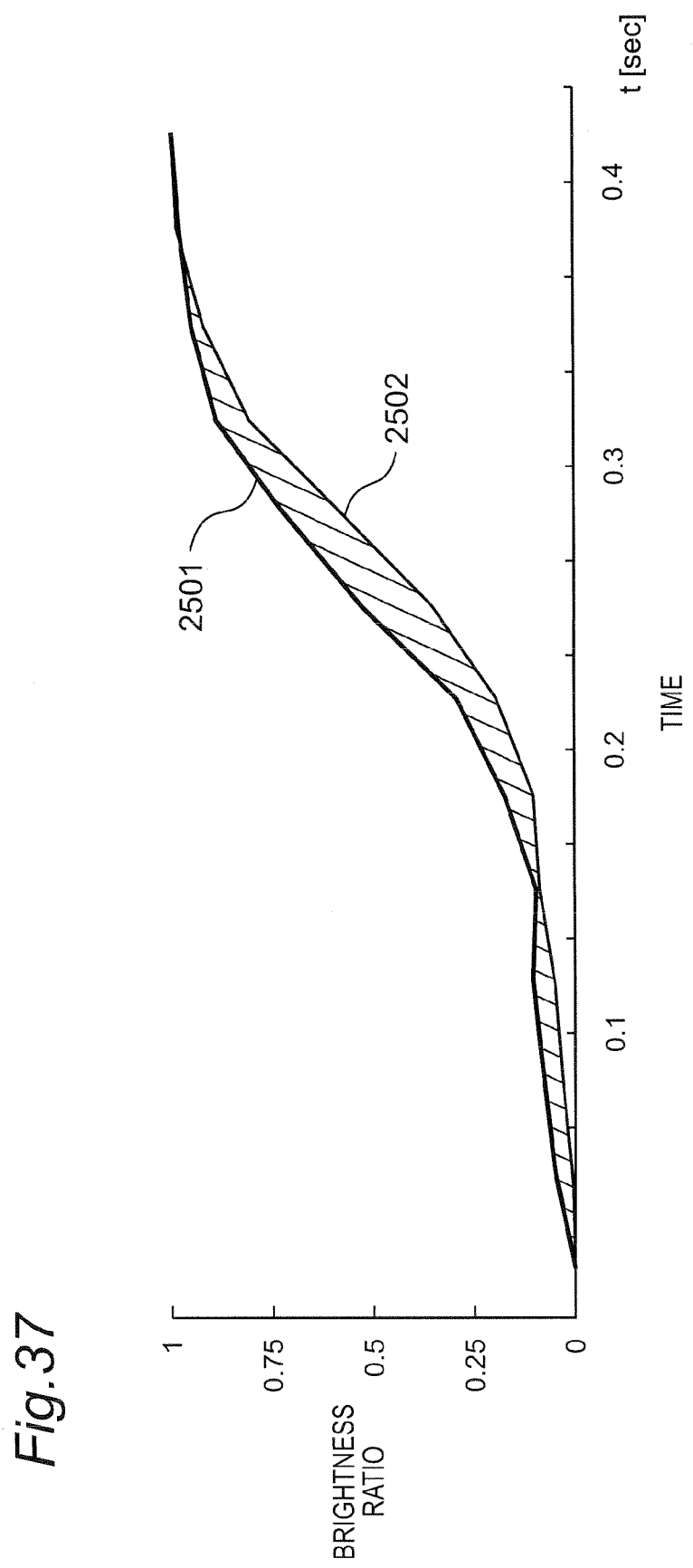
FIG. 37 is a graph indicating an evaluation value for the candidate corresponding point Qk_1 according to the third embodiment.

FIG. 37 is a graph indicating the evaluation value H_n for the candidate corresponding point Qk_1. In FIG. 37, the thick line 2501 and the solid line 2502 indicate the normalized brightness sequence of the contrast point Pk and the normalized brightness sequence of the candidate corresponding point Qk_1, respectively. The evaluation value H_n for the candidate corresponding point Qk_1 corresponds to the area of the shaded region in FIG. 37.

Figure 38:
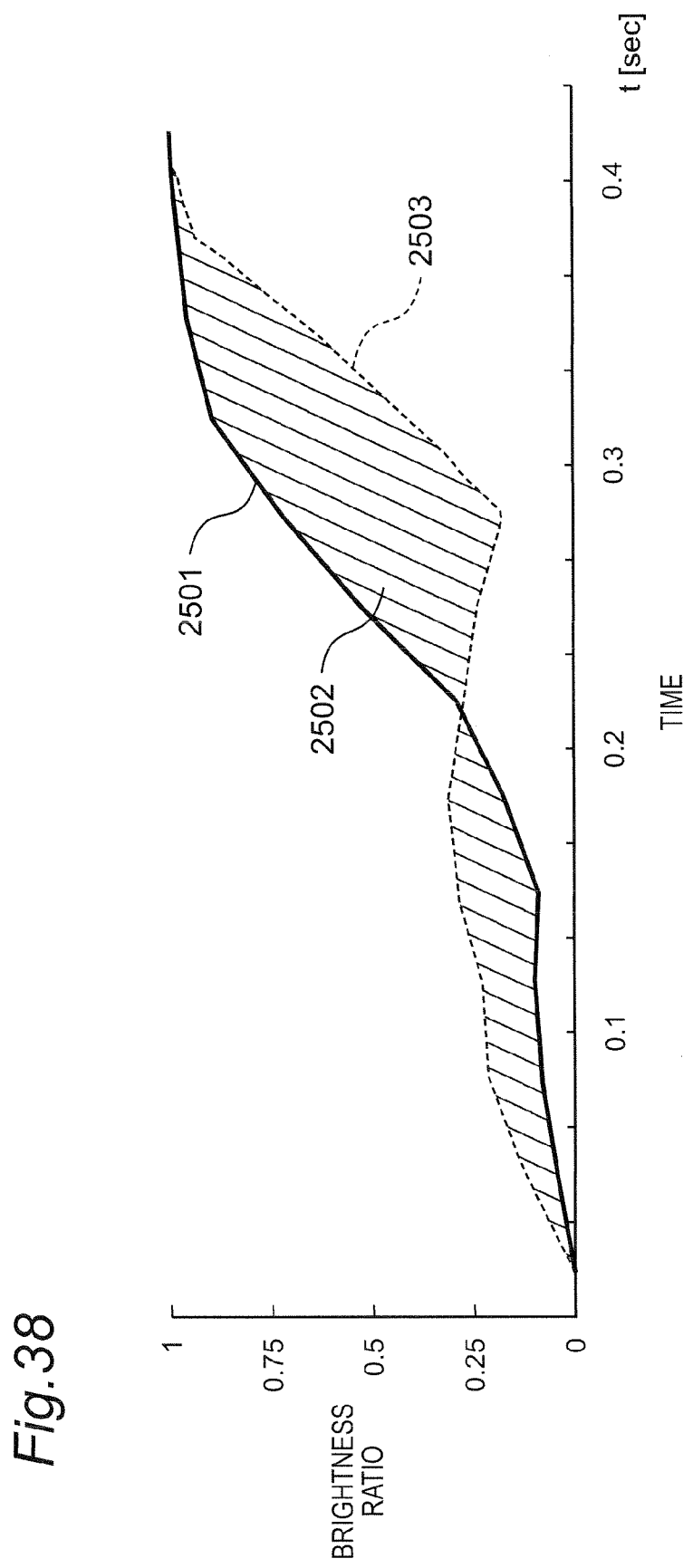
FIG. 38 is a graph indicating an evaluation value for the candidate corresponding point Qk_2 according to the third embodiment.

FIG. 38 is a graph indicating the evaluation value H_n for the candidate corresponding point Qk_2. In FIG. 38, the thick line 2501 and the dotted line 2503 indicate the normalized brightness sequence of the contrast point Pk and the normalized brightness sequence of the candidate corresponding point Qk_2, respectively. The evaluation value H_n for the candidate corresponding point Qk_2 corresponds to the area of the shaded region in FIG. 38.

The brightness sequence evaluation holder 1710 holds the evaluation values (or a difference sum) H_n (n=1, 2, . . . , N) for the brightness sequences of the candidate corresponding points Qk_n (n=1, 2, . . . , N) acquired by the brightness sequence holder 1708.

The corresponding region determiner 1711 selects the minimum evaluation value from the evaluation values H_n (n=1, 2, . . . , N) held by the brightness sequence evaluation holder 1710. When the corresponding region determiner 1711 selects the evaluation value H_n, the corresponding region determiner 1711 determines the candidate corresponding point Qk_n as a corresponding point Qk of the contrast point Pk. In a case where the evaluation values H_1 and H_2 correspond to the areas of the shaded regions in FIGS. 37 and 38, the corresponding region determiner 1711 determines the candidate corresponding point Qk_1 having the smaller area as the corresponding point Qk of the contrast point Pk.

Figure 39:
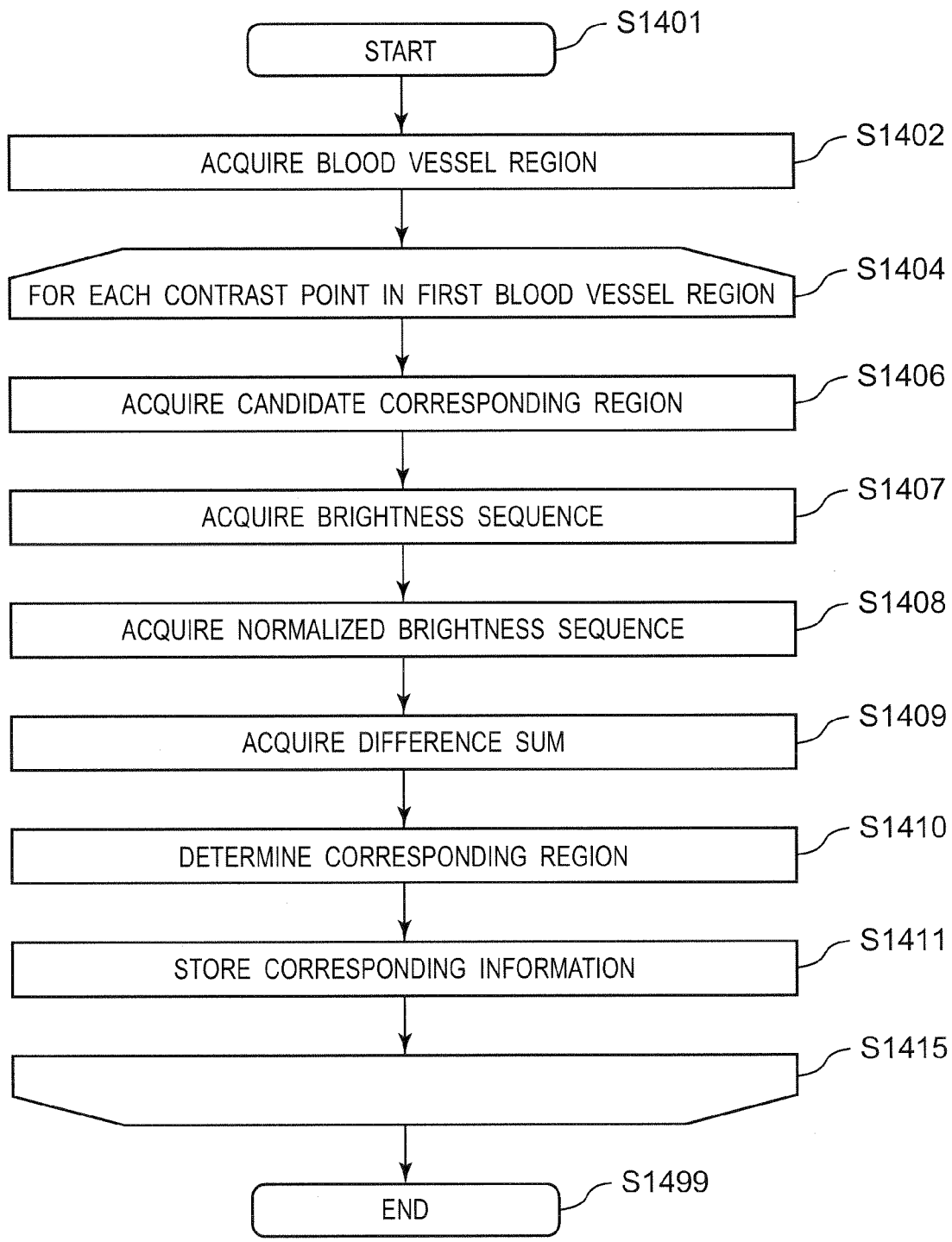
FIG. 39 is a flowchart of a mapping controller according to the third embodiment.

The mapping controller 1701 controls the respective units in the mapping unit 107 to execute mapping. FIG. 39 is a flowchart of a flow of the processes executed by the mapping controller 1701.

The mapping controller 1701 starts the processes in step S1401.

Subsequently in step S1402, the mapping controller 1701 acquires the first blood vessel region image 1101 from the blood vessel region holder 106.

The mapping controller 1701 then executes the processes in steps S1404 to S1415 to a black point (s) in the blood vessel region on the first blood vessel region image 1101 acquired in step S1402. Assume that the black point (s) corresponds to each of the contrast points Pk (k=1, 2, ..., K; where K is the number of black points) in the following description.

Initially in step S1406, the mapping controller 1701 commands the candidate corresponding region acquiring unit 1705 to execute the process. The candidate corresponding region acquiring unit 1705 acquires the candidate corresponding points Qk_n (n=1, 2, ..., N; where N is the number of candidate corresponding points) of the contrast point Pk, and stores coordinates of the candidate corresponding points Qk_n (n=1, 2, ..., N) thus acquired in the candidate corresponding region holder 1706.

Then in step S1407, the mapping controller 1701 commands the brightness sequence acquiring unit 1707 to execute the process. The brightness sequence acquiring unit 1707 acquires the brightness sequences of the contrast point PK and the candidate corresponding points Qk_n (n=1, 2, ..., N) held by the candidate corresponding region holder 1706 and stores the acquired brightness sequences in the brightness sequence holder 1708.

Then in step S1408, the mapping controller 1701 commands the normalized brightness sequence acquiring unit 1721 to execute the process. The normalized brightness sequence acquiring unit 1721 extracts the maximum value of the brightness sequences held by the brightness sequence holder 1708, calculates, as normalized brightness sequences, sequences of values obtained by dividing respective values of the brightness sequences by the extracted maximum value to acquire normalized brightness sequences of the contrast point Pk and the candidate corresponding points Qk_n (n=1, 2, ..., N), and stores the normalized brightness sequences in the normalized brightness sequence holder 1722.

Then in step S1409, the mapping controller 1701 commands the difference sum acquiring unit 1720 to execute the process. The difference sum acquiring unit 1720 calculates the evaluation values H_n (n=1, 2, ..., N) indicating whether the normalized brightness sequences of the candidate corresponding points Qk_n (n=1, 2, ..., N) held by the normalized brightness sequence holder 1722 each have a brightness change similar to or different from that of the normalized brightness sequence of the contrast point Pk to acquire the evaluation values (or a difference sum) of the candidate corresponding points Qk_n (n=1, 2, ..., N), and stores the evaluation values in the brightness sequence evaluation holder 1710.

Then in step S1410, the mapping controller 1701 commands the corresponding region determiner 1711 to execute the process. The corresponding region determiner 1711 determines the corresponding point Qk of the contrast point Pk. More specifically, the corresponding region determiner 1711 selects a candidate corresponding point Qk_x (x is an identifier of a candidate corresponding point having an evaluation value Hk) having the minimum evaluation value Hk out of the evaluation values H_n held by the brightness sequence evaluation holder 1710. The corresponding region determiner 1711 regards the minimum evaluation value Hk as the evaluation value for the corresponding point Qk.

In step S1411, under the control of the mapping controller 1701, the corresponding region determiner 1711 stores, in the corresponding information holder 108, coordinates of the contrast point Pk, coordinates of the corresponding point Qk, and the evaluation value Hk for the corresponding point Qk. The processes from step S1404 thus end.

The mapping controller 1701 ends the processes in step S1499.

The corresponding information holder 108 stores the coordinates of the contrast points Pk (k=1, 2, ..., K; where K is the number of contrast points), the coordinates of the corresponding points Qk (k=1, 2, ..., K), and the evaluation values Hk (k=1, 2, ..., K) for the corresponding points Qk, which are acquired by the mapping unit 107. FIG. 40 exemplarily indicates a data structure of the corresponding information holder 108. The corresponding information holder 108 holds no set in the initial state. One line of data is added to the corresponding information holder 108 every time the process of the mapping controller 1701 in step S1411 is executed.

The 3D position acquiring unit 109 shown in FIG. 21 calculates coordinates of the 3D points Jk in 3D (three dimensions) from the coordinates of the contrast point Pk in each line and the coordinates of the corresponding point Qk in each line held by the corresponding information holder 108 in accordance with the triangulation principle, and stores the calculated coordinates of the 3D points Jk (k=1, 2, ..., K) in the 3D position holder 110.

Figures 41, 42:
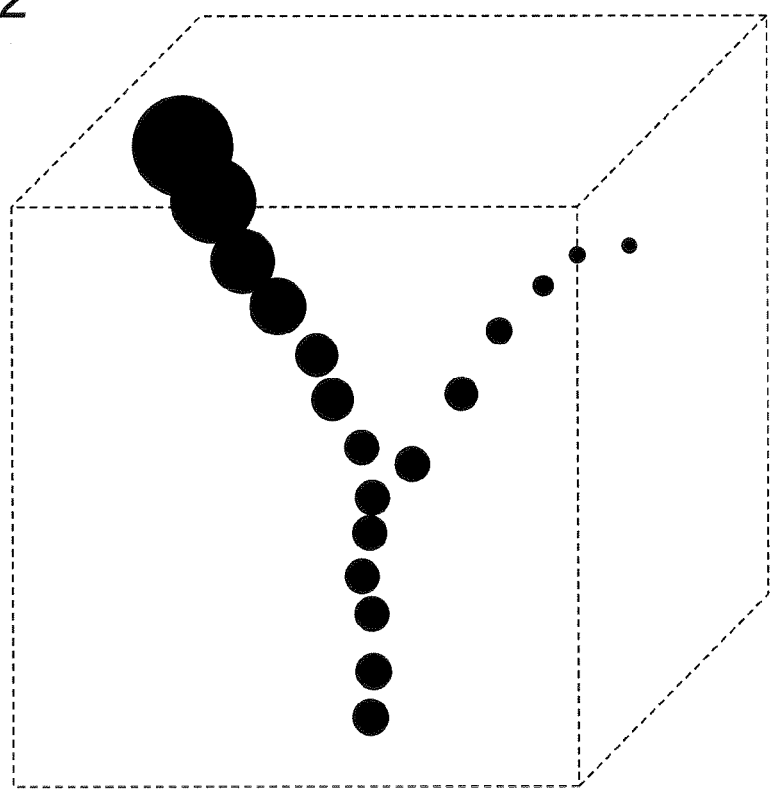
FIG. 41 is an exemplary view of a data structure of a 3D position holder according to the third embodiment.
FIG. 42 is a view of a display screen generated by a display screen generator according to the third embodiment.

The 3D position holder 110 holds the coordinates of the 3D points Jk (k=1, 2, ..., K) calculated by the 3D position acquiring unit 109. FIG. 41 is an exemplary view of a data structure of the 3D position holder 110. The 3D position holder 110 holds coordinates (JK_X, JK_Y, JK_Z) in a line K. The 3D point Jk has X, Y, and Z coordinates of JK_X, JK_Y, and JK_Z, respectively.

The display screen generator 111 generates a computer graphics (CG) screen displaying the 3D points Jk (k=1, 2, ..., K) held by the 3D position holder 110. FIG. 42 is an exemplary view of the display screen generated by the display screen generator 111. Each 3D point is indicated by a sphere in an exemplary 3D display manner in FIG. 42, but each 3D point can be indicated in any other manner. Each 3D point can be indicated by a polygon or the like.

The display unit 112 displays the screen generated by the display screen generator 111. More particularly, the display unit 112 is a display device such as a display or a projector.

<Flow of Processes Executed by Shape Restoring Apparatus 1>

Figure 43:
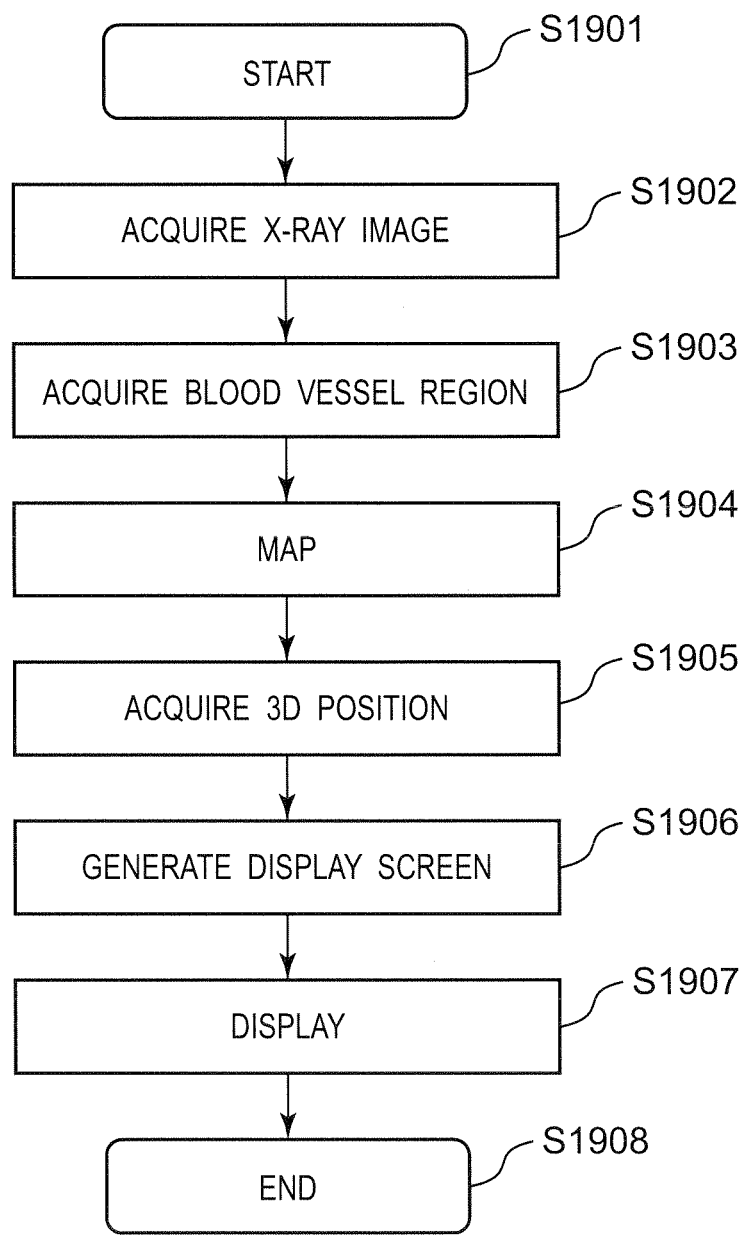
FIG. 43 is a flowchart of a shape restoring apparatus according to the third embodiment.

FIG. 43 is a flowchart of the processes executed by the shape restoring apparatus 1.

The shape restoring apparatus 1 starts the processes in step S1901.

Subsequently in step S1902, the X-ray image acquiring unit 113 executes the above-described process of the X-ray image acquiring unit 113. More specifically, the X-ray image acquiring unit 113 acquires X-ray images from the radiographing units 101 and 102 and stores the acquired X-ray images in the X-ray image holder 103.

Subsequently in step S1903, the blood vessel region acquiring unit 105 executes the above-described process of the blood vessel region acquiring unit 105. More specifically, the blood vessel region acquiring unit 105 acquires the first and second blood vessel region images 1101 and 1102 in accordance with the images held by the X-ray image holder 103, and stores the first and second blood vessel region images 1101 and 1102 thus acquired in the blood vessel region holder 106.

Subsequently in step S1904, the mapping unit 107 executes the above-described process of the mapping unit 107. More specifically, the mapping unit 107 determines the corresponding point Qk of each of the contrast points Pk (k=1, 2, . . . , K) on the first blood vessel region image 1101 held by the blood vessel region holder 106, and stores corresponding information in the corresponding information holder 108.

Subsequently in step S1905, the 3D position acquiring unit 109 executes the above-described process of the 3D position acquiring unit 109. More specifically, the 3D position acquiring unit 109 calculates a 3D position of the 3D point Jk for each of the contrast points Pk (k=1, 2, . . . , K) on the first blood vessel region image 1101 in accordance with the corresponding information stored in the corresponding information holder 108, and stores the 3D positions in the 3D position holder 110.

Then in step S1906, the display screen generator 111 generates a CG screen displaying the 3D points Jk (k=1, 2, . . . , K) in accordance with the 3D positions of the 3D points Jk held by the 3D position holder 110.

Then in step S1907, the display unit 112 displays the screen generated by the display screen generator 111. The series of processes then ends in step S1908.

<Principle of Processes Executed by Shape Restoring Apparatus 1>

When the contrast medium is injected into the blood vessel 1201, the contrast medium staying at the 3D point Jk on the blood vessel 1201 changes in amount as time passes. The contrast point Pk obtained by capturing the 3D point Jk and the corresponding point Qk change in brightness in this case. The shape restoring apparatus 1 acquires brightness change information on the contrast point Pk and the plurality of candidate corresponding points Qk_n (n=1, 2, . . . , N), evaluates a similarity degree for the brightness change information, and causes the corresponding region determiner 1711 to determine the corresponding point Qk out of the candidate corresponding points Qk_n.

Figure 44:
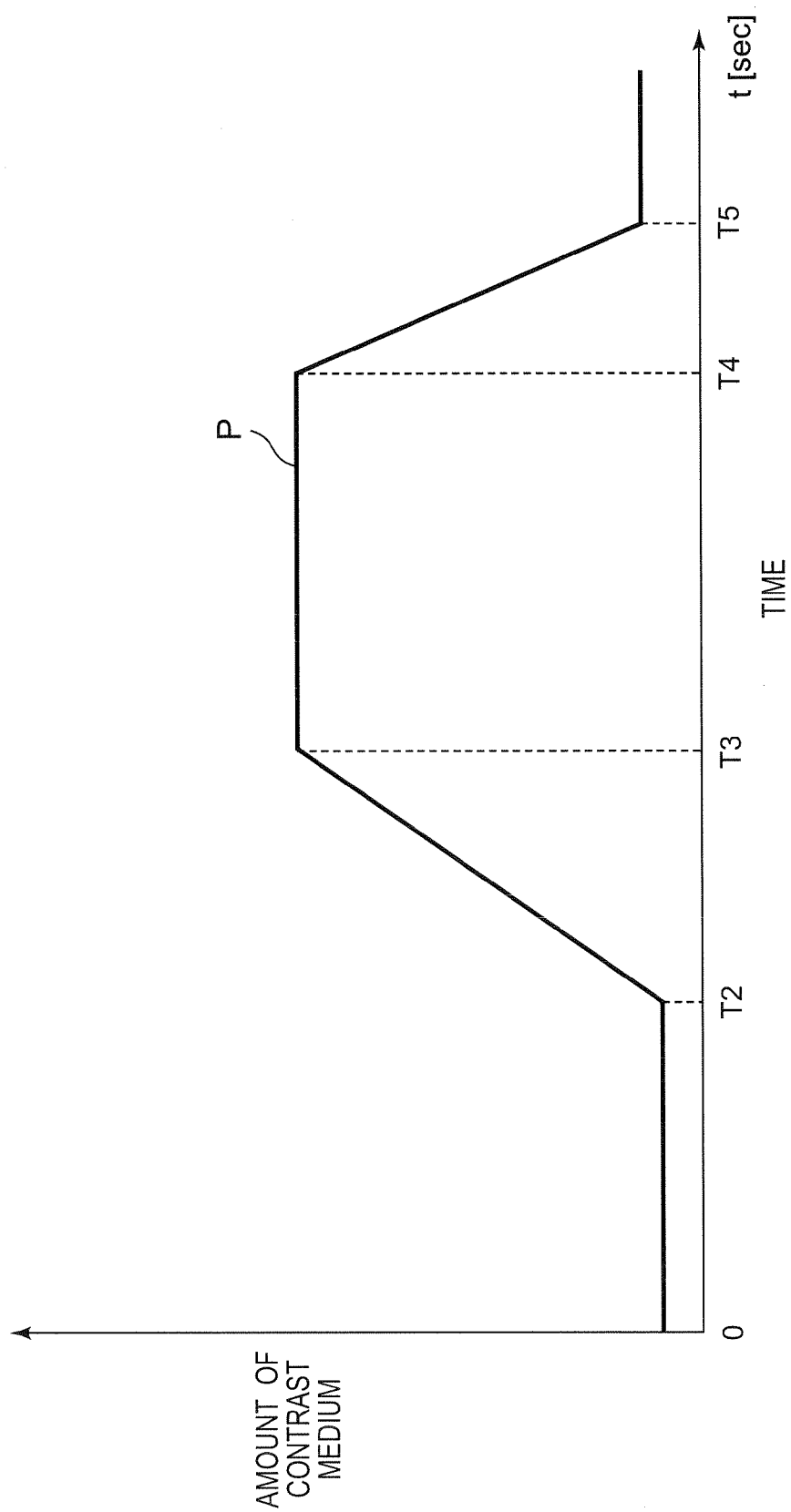
FIG. 44 is a graph indicating an amount of a contrast medium flowing to a 3D point Jk according to the third embodiment.

Initially described is a change in amount of the contrast medium at the 3D point Jk on the blood vessel 1201. FIG. 44 indicates a change in amount of the contrast medium at a 3D point Jk. The contrast medium does not flow before the contrast medium is injected (until a time T2). The contrast medium starts flowing gradually from the time T2 and flows constantly at a time T3. The contrast medium starts decreasing gradually from a time T4 and does not flow at a time T5.

Such a change in amount of the contrast medium in the blood vessel 1201 with time differs at portions of the blood vessel. For example, the change in amount of the contrast medium with time at the time T2 when the contrast medium starts flowing is fast at a position close to a point of jetting the contrast medium. In contrast, the change in amount of the contrast medium with time at the time T2 when the contrast medium starts flowing is slow at a position distant from the point of jetting the contrast medium. The change in amount of the contrast medium with time at the time T4 when the contrast medium starts decreasing also differs at portions of the blood vessel.

The change in amount of the contrast medium with time from the time T2 when the contrast medium starts flowing to the time T3 when the contrast medium flows constantly also differs at portions of the blood vessel. For example, at a portion where blood flows upward, the contrast medium flows against the gravity and it takes a long time period for the contrast medium to increase in concentration. A time period (T3–T2) required for the contrast medium to become constant in concentration is thus long. In contrast, at a portion where the contrast medium flows downward, the contrast medium is increased in speed by the gravity. The time period (T3–T2) required for the contrast medium to become constant in concentration is thus short. Blood flows fast in a narrow blood vessel and the time period (T3–T2) required for the contrast medium to become constant in concentration is thus short. In contrast, blood flows slowly in a wide blood vessel and the time period (T3–T2) required for the contrast medium to become constant in concentration is thus long. As described above, the contrast medium flowing at a certain portion of a blood vessel changes in amount with time, and how the contrast medium changes in amount defers at portions of the blood vessel. A time period (T5–T4) from the start to the end of decrease of the contrast medium also differs at portions of the blood vessel.

Described next are brightness changes at the contrast point Pk and the corresponding point Qk in a case where the contrast medium at the 3D point Jk changes in concentration. Brightness of the contrast point Pk that is obtained by projecting the 3D point Jk on an X-ray image changes at a degree similar to the change in concentration of the contrast medium at the 3D point Jk. The contrast point Pk and the corresponding point Qk are decreased in brightness when the contrast medium at the 3D point Jk is increased in concentration. In contrast, the contrast point Pk and the corresponding point Qk are increased in brightness when the contrast medium at the 3D point Jk is decreased in concentration. The contrast point Pk and the corresponding point Qk are obviously changed in brightness at a degree similar to the change in concentration of the contrast medium.

FIG. 33 indicates the brightness sequences in a case where a certain 3D point Jk is captured in two different directions. In FIG. 33, the thick line 2301 indicates the brightness sequence of the contrast point Pk of the 3D point Jk, and the solid line 2302 indicates the brightness sequence of the corresponding point Qk of the contrast point Pk. The dotted line 2303 indicates a brightness change of a corresponding point Qx captured in a direction different from the direction of capturing an image including a contrast point Pk of a 3D point Jx (x≠k) that is different from the 3D point Jk. The transverse axis in the graph indicates time and each scale indicates 33 msec. The ordinate axis indicates brightness of a difference image. This graph indicates the brightness from the time when the contrast medium is injected to the time when the contrast medium is stabilized halfway in concentration. In this graph, the brightness sequences of the contrast point Pk and the corresponding point Qk are increased and decreased at similar degrees, but the brightness sequences of the contrast point Pk and the corresponding point Qx are changed at different degrees.

However, the brightness itself of the contrast point Pk and the brightness itself of the corresponding point Qk do not match each other as indicated in FIG. 33. For example, the contrast point Pk has brightness of "56" whereas the corresponding point Qk has brightness of "46" at a time 13 (at 0.4 sec in the figure).

Figure 45:
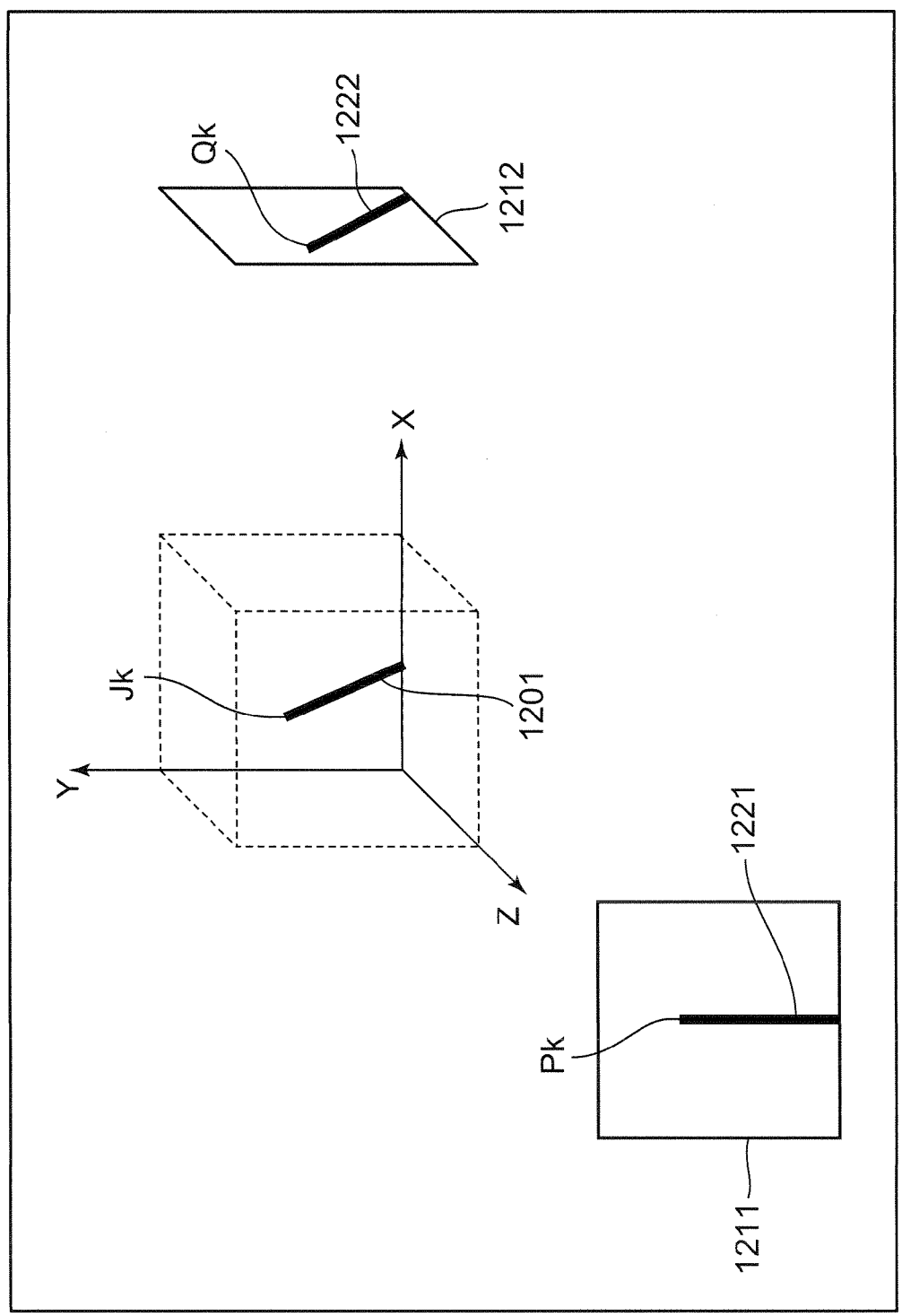
FIG. 45 is an exemplary view of a 3D blood vessel according to the third embodiment.
Figure 46:
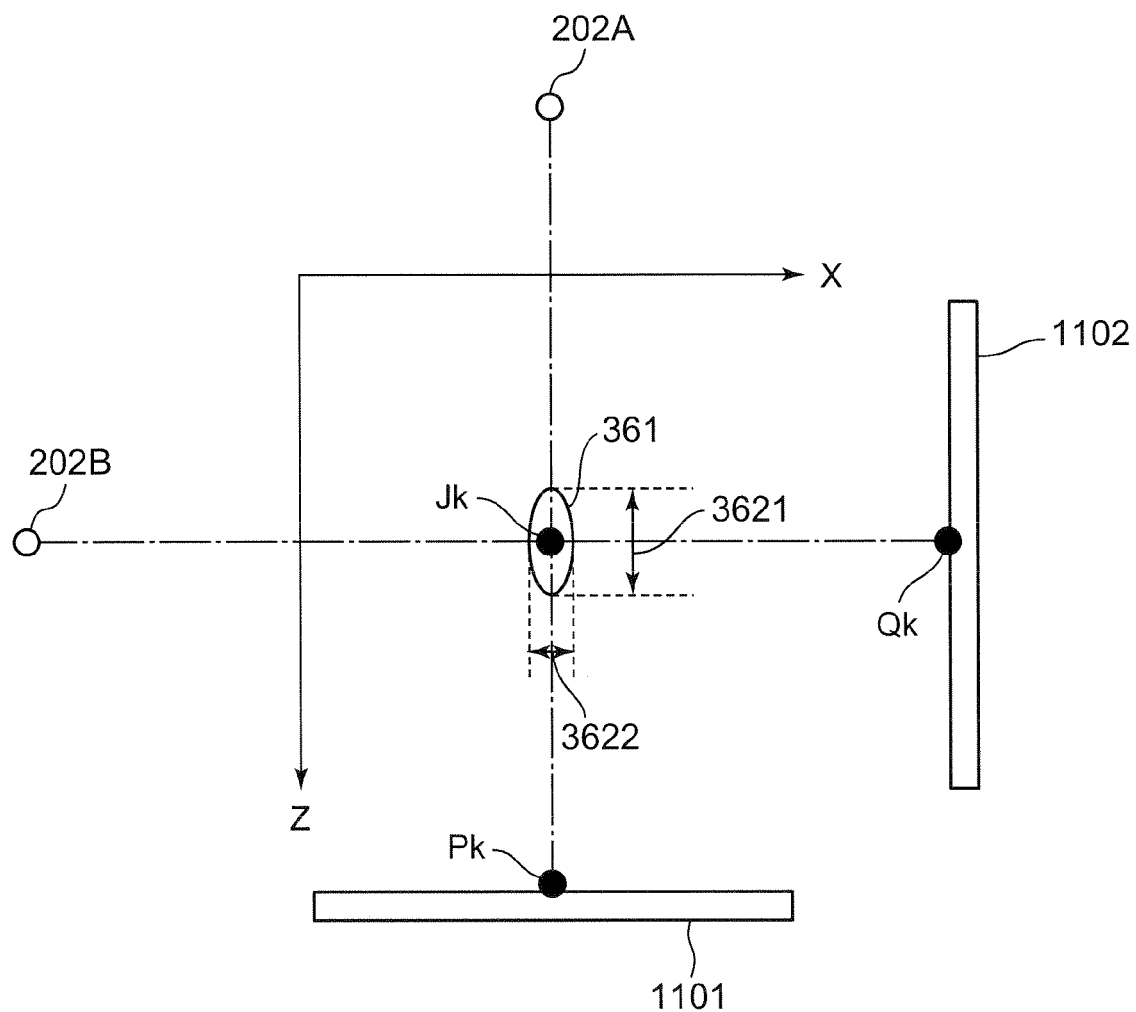
FIG. 46 is a view of a section of the blood vessel according to the third embodiment.

The reason for such a brightness difference is relevant to a sectional shape of the blood vessel 1201. The relevance is described below with reference to FIGS. 45 and 46. FIG. 45 is an exemplary view of the blood vessel 1201. An X-ray image 1211 is captured by the radiographing unit 101, and a blood vessel image 1221 is an image of the blood vessel 1201 on the X-ray image 1211. Similarly, an X-ray image 1212 is captured by the radiographing unit 102, and a blood vessel image 1222 is an image of the blood vessel 1201 on the X-ray image 1212. Reference characters Jk, Pk, and Qk indicate the 3D point Jk, the contrast point Pk of the 3D point Jk, and the corresponding point Qk of the contrast point Pk, respectively. FIG. 46 is a view of a plane (epipolar plane) including the 3D point Jk, the contrast point Pk, and the corresponding point Qk, which is viewed from a +Y position toward a −Y position in FIG. 45. The blood vessel 1201 has a blood vessel section 361 in an elliptical shape as shown in FIG. 46. (The blood vessel 1201 typically has an elliptical sectional shape except in a specific case.) The blood vessel 1201 has a thickness 3621 at a portion where an X-ray passes to reach the contrast point Pk, and has a thickness 3622 at a portion where an X-ray passes to reach the contrast point Qk. The thickness 3621 and the thickness 3622 are different from each other because the blood vessel 1201 has the elliptical sectional shape (not a circular shape). An X-ray passes the thicker blood vessel section to reach the contrast point Pk, and the contrast point Pk thus has brightness lower than the brightness of the corresponding point Qk (with a smaller brightness difference from the background). In this manner, the brightness of the contrast point Pk (or the corresponding point Qk) obtained by capturing the 3D point Jk on the blood vessel 1201 has a smaller value as an X-ray passes a thicker portion of the blood vessel 1201. The thickness of the portion of the blood vessel 1201 where an X-ray passes differs depending on the direction of capturing the blood vessel 1201. The contrast point has different brightness depending on the capture direction even though the identical 3D point Jk is projected.

In order to eliminate such a brightness difference depending on the capture direction, the brightness sequences are normalized and normalized brightness sequences are compared for determination of the corresponding point in the third embodiment.

The normalized brightness sequences are compared in accordance with Equation 10 on difference summing in the third embodiment. When the normalized brightness sequence of the contrast point Pk and the normalized brightness sequence of the corresponding point Qk change at the same degrees, values of normalized brightness are equal to each other at each time. When the brightness sequence evaluator 1709 calculates the sum of the absolute values of the differences in normalized brightness at respective times, the sum of the absolute values is theoretically 0. The brightness sequence evaluator 1709 according to the third embodiment regards the value obtained in accordance with Equation 10 as an evaluation value and determines the candidate corresponding point Qk_n having the minimum evaluation value as the corresponding point Qk of the contrast point Pk.

<Effects of the Third Embodiment>

The image region mapping device and the 3D model generating apparatus according to the present disclosure can determine a corresponding point in accordance with a change in normalized brightness sequence in a case where the epipolar line L2 includes a plurality of candidate corresponding points Qk_n (n=1, 2, . . . , N) of the contrast point Pk.

Firstly, a corresponding point can be determined for each of the contrast points Pk on the blood vessel into which the contrast medium is injected. According to the technique of Non-Patent Literature 1, a blood vessel can be mapped only at an end point of a blood vessel region. In contrast, the image region mapping device and the 3D model generating apparatus according to the third embodiment of the present disclosure can map points in addition to the end point to restore a finer shape.

According to the present disclosure, the evaluation value is obtained by summing differences between normalized brightness of the contrast point Pk and normalized brightness of the candidate corresponding point Qk_n of the contrast point Pk at respective times. Such an evaluation value for the corresponding point Qk of the contrast point Pk is smaller (than evaluation values for the candidate corresponding points other than the corresponding point). The corresponding point can be thus determined in accordance with the evaluation value.

Secondly, the contrast point Pk can be mapped even when the blood vessel 1201 has an elliptical sectional shape.

Figure 47:
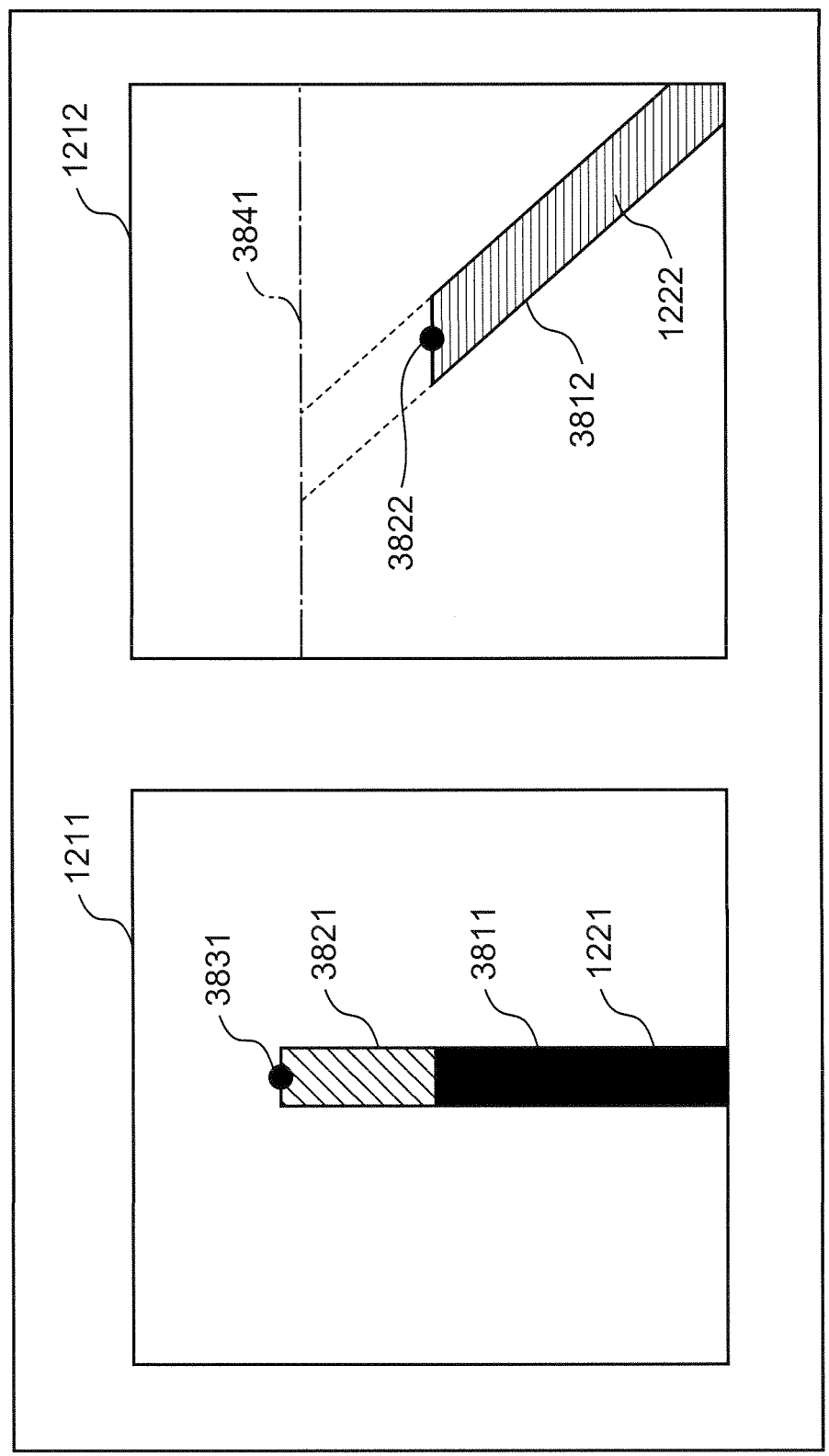
FIG. 47 is a view of X-ray images 1211 and 1212 that captured the 3D blood vessels according to the third embodiment.

Two illustrations in FIG. 47 show the enlarged X-ray images 1211 and 1212 in FIG. 45. The blood vessel image 1221 on the X-ray image 1211 has a dark portion 3811 (the portion with low brightness, in other words, the portion largely different in brightness from the background) and a bright portion 3821 (the portion with high brightness, in other words, the portion slightly different in brightness from the background). The bright portion 3821 actually has gradation in brightness, and is gradually brighter in the upward direction. The contrast medium injected into the blood vessel 1201 is mixed with peripheral blood, so that the contrast medium is gradually decreased in concentration toward the end. In other words, the brightness is higher (brighter) toward the end. The blood vessel image 1221 has a blood vessel end point 3831 at its end point. A blood vessel portion captured as the dark portion 3811 on the X-ray image 1211 corresponds to a bright portion 3812 on the X-ray image 1212. This is because the X-ray images 1211 and 1212 are different from each other in brightness of the blood vessel images, as described earlier. A blood vessel portion captured as the dark portion 3811 on the X-ray image 1211 appears brighter on the X-ray image 1212 and cannot be extracted (the range surrounded with a dotted line in the right illustration in FIG. 47 cannot be extracted). The blood vessel image 1222 thus has an endpoint at the position denoted by reference numeral 3822. The end point 3831 extracted on the X-ray image 1211 and the end point 3822 extracted on the X-ray image 1212 are thus projection points of different 3D points. Any corresponding point is not located on an epipolar line 3841 for the end point 3831 and the end points cannot be mapped in this case. There is assumed to be only one blood vessel 1201 in this case. If an endpoint of a different blood vessel is located on the epipolar line 3841, the different blood vessel may be mapped erroneously. The normalized brightness changes of the contrast point Pk and the candidate corresponding point Qk_n are compared in the present disclosure. Even when the contrast point Pk and the corresponding point Qk are different from each other in brightness, comparison between the brightness sequences achieves accurate mapping. Even when the contrast point Pk and the corresponding point Qx (x≠k) are equal to each other in brightness at a specific time, comparison between the brightness sequences achieves accurate mapping.

According to the third embodiment, for calculation of the evaluation value for the candidate corresponding point Qk_n, the normalized brightness sequences are generated first and compared with each other. In a case where the radiographing units 101 and 102 are located in similar directions (or in different directions at about 180 degrees), the brightness sequences themselves can be compared alternatively.

According to the third embodiment, injection of the contrast medium starts after the X-ray image acquiring unit 113 starts the process. Alternatively, the X-ray image acquiring unit 113 can start the process after injection of the contrast medium starts.

According to the third embodiment, the blood vessel region acquiring unit 105 executes the process after the input IF 114 commands end of image capture. Alternatively, subsequent steps S1903 to S1907 can be executed every time the image acquiring unit 113 acquires an X-ray image. In such a configuration, an operating person (operator) can view the display unit 112 to check a 3D shape of the blood vessel 1201 also at timing when the contrast medium is expanding in the blood vessel 1201.

According to the third embodiment, the display screen generator 111 generates the candidate corresponding point Qk_n having the best evaluation value out of the candidate corresponding points Qk_n (n=1, 2, ..., N) of the contrast point Pk and the display unit 112 displays the generated candidate corresponding point Qk_n. However, the corresponding point of the contrast point Pk is not always captured. For example, the corresponding point is not captured when the 3D point Jk is located at a position not captured by the radiographing unit 102. When the best evaluation value is worse than a predetermined threshold (when the minimum evaluation value out of the evaluation values for the candidate corresponding points is larger than a predetermined evaluation value in this case), the display unit 112 can be configured not to display the candidate corresponding point Qk_n. The display unit 112 can optionally include a unit configured to input the predetermined threshold. In this case, the display unit 112 displays only the corresponding point that has an evaluation value smaller than the predetermined threshold.

The brightness sequence acquiring unit 1707 according to the third embodiment acquires the brightness sequence of the difference between the brightness at each time and the brightness of the background image. The brightness sequence acquiring unit 1707 can alternatively acquire a brightness sequence of the brightness itself at each time. In this case, normalization is executed by acquiring the minimum value and the maximum value of the brightness sequence and regarding a sequence of a value of {(brightness)−(minimum value)}/{(maximum value)−(minimum value)} as the normalized brightness sequence.

According to the third embodiment, the photographing unit information holder 104 preliminarily holds the photographing unit information including the translation vector T, the rotation vector R, and the internal parameters A1 and A2. Alternatively, the photographing unit information holder 104 can acquire and hold such information at any given time from the positions of the X-ray generators 202 and the X-ray detectors 203 of the radiographing units 101 and 102.

The blood vessel region acquiring unit 105 according to the third embodiment acquires the region of the blood vessel 1201 into which the contrast medium is injected from the images 1_END and 2_END. Alternatively, the blood vessel region acquiring unit 105 can acquire the region into which the contrast medium is injected at each time and regard the sum of the acquired regions as the blood vessel region. In such configuration, if there is a range not extracted as a blood vessel region at the time END and such a range can be extracted as the blood vessel region at a different time, the blood vessel region acquiring unit 105 can eventually extract a blood vessel region including the region.

The process of the line thinning unit 1503 in the blood vessel region acquiring unit 105 according to the third embodiment may not be executed. The line thinning unit 1503 executes the process in order to reduce the number of contrast points Pk of which corresponding points are to be found by the mapping unit 107. When the process of the line thinning unit 1503 is not executed, the process of the mapping unit 107 takes a longer time period.

The brightness sequence evaluator 1709 according to the third embodiment compares the normalized brightness sequences of the contrast point Pk and the candidate corresponding points Qk_n and obtains the sum of the brightness differences as the evaluation value. The brightness sequence evaluator 1709 can alternatively regard the maximum value of the brightness differences as the evaluation value.

(Fourth Embodiment)

According to the third embodiment of the present disclosure, the difference sum acquiring unit 1720 acquires the difference sum obtained in accordance with Equation 10 for the respective candidate corresponding points Qk_n (n=1, 2, . N) of the contrast point Pk, and the corresponding region determiner 1711 determines the candidate corresponding point Qk_n having the minimum difference sum as the corresponding point Qk of the contrast point Pk.

Figure 48:
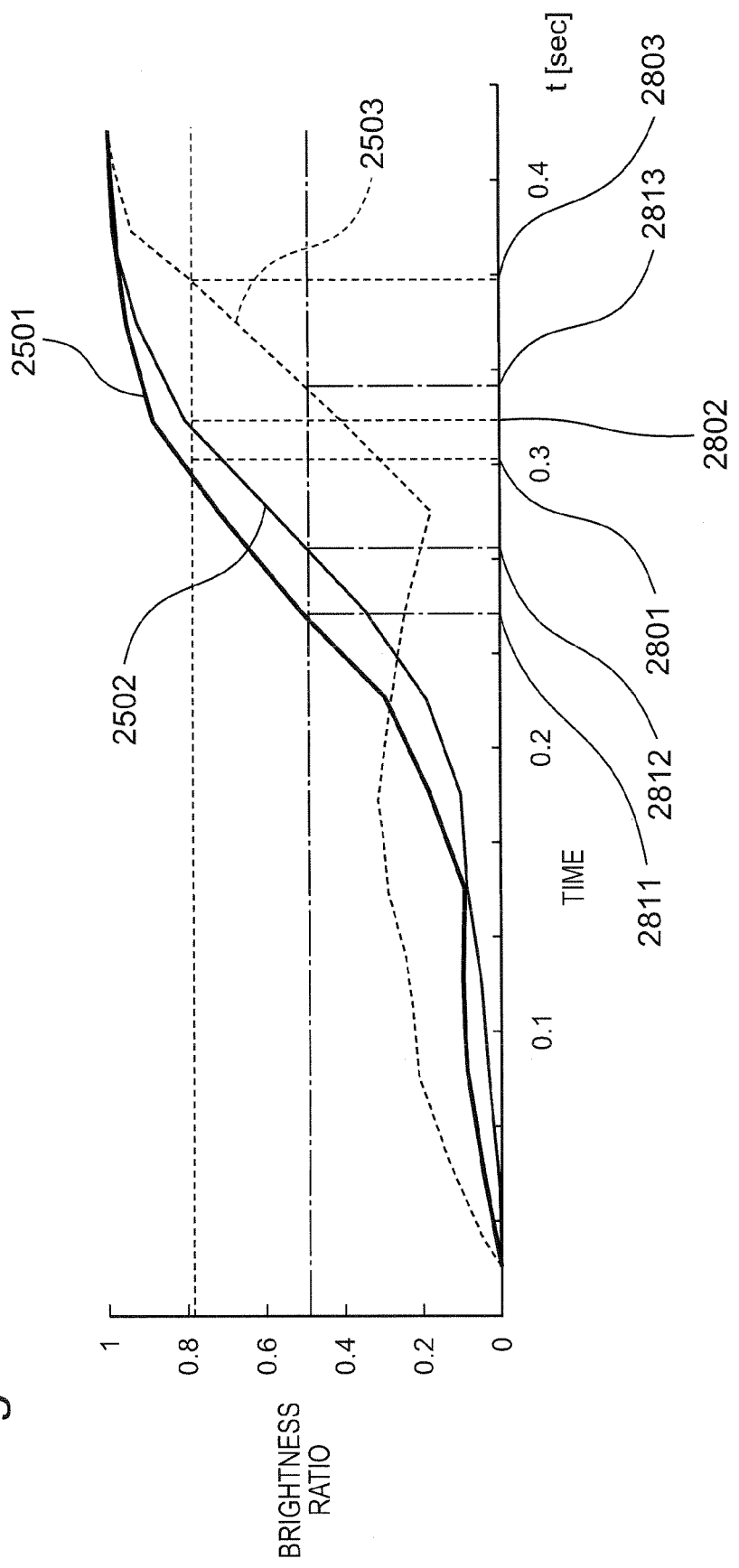
FIG. 48 is a graph indicating a predetermined ratio time according to a fourth embodiment.

The difference sum is replaced with a predetermined ratio time in the fourth embodiment of the present disclosure. The predetermined ratio time is a time when brightness of the contrast point Pk (or the candidate corresponding point Qk_n) reaches a predetermined ratio (predetermined percentage) (e.g. 80% or 50%) to the maximum brightness of the point. The predetermined ratio time is described below with reference to FIG. 48. FIG. 48 includes the line 2501 of the normalized brightness sequence of the contrast point Pk, the line 2502 of the normalized brightness sequence of the corresponding point Qk of the contrast point Pk, and the line 2503 of the normalized brightness sequence of the corresponding point Qx (x≠k) other than the corresponding point Qk captured by the radiographing unit 102. FIG. 48 also indicates predetermined ratio times 2801, 2802, and 2803 of the contrast point Pk, the corresponding point Qk, and the corresponding point Qx for a case where the predetermined ratio (predetermined percentage) is 0.8 (80%). FIG. 48 further indicates predetermined ratio times 2811, 2812, and 2813 of the contrast point Pk, the corresponding point Qk, and the corresponding point Qx for a case where the predetermined ratio (predetermined percentage) is 0.5 (50%).

Figure 49:
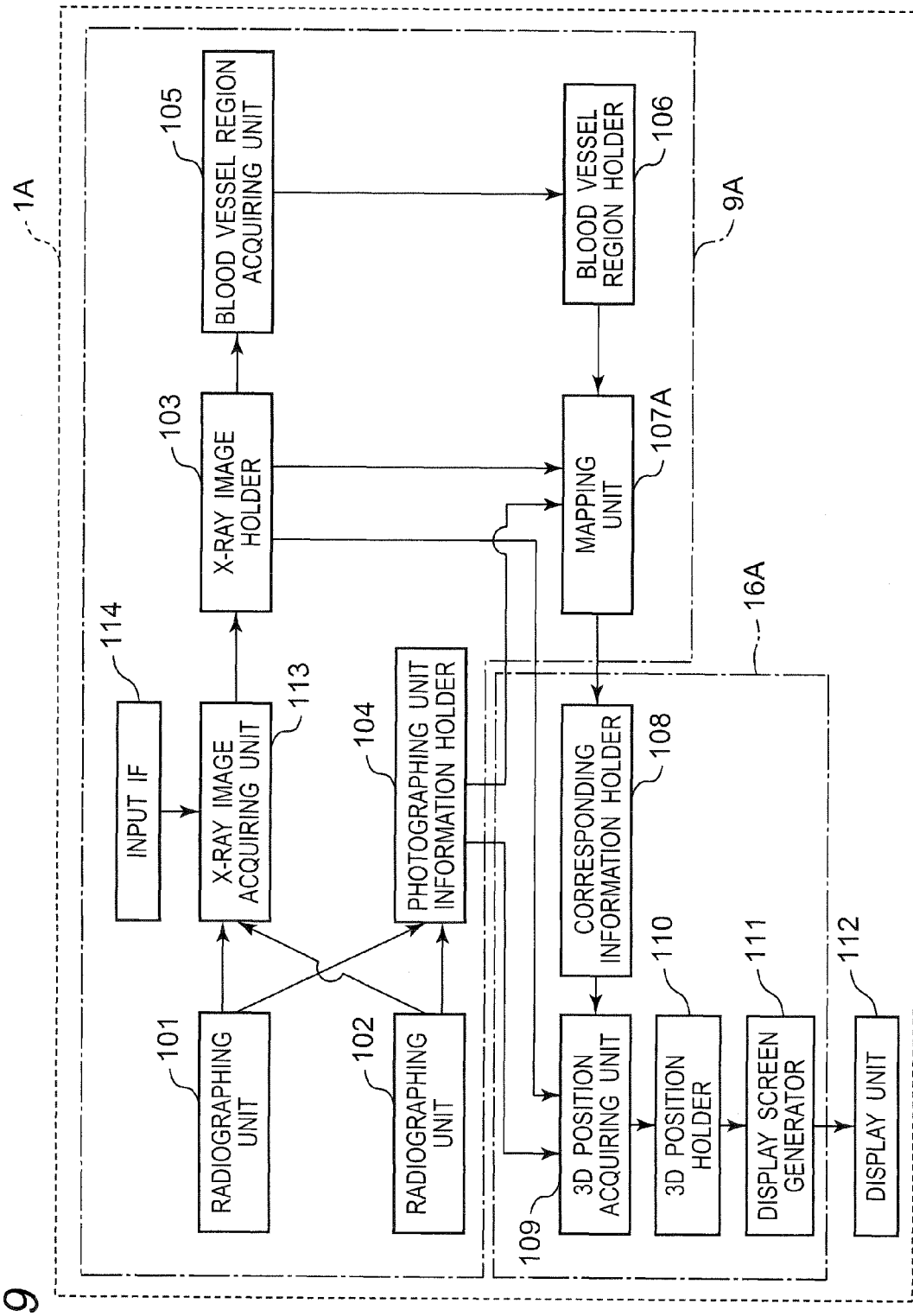
FIG. 49 is a view of the configuration of a shape restoring apparatus according to the fourth embodiment.

FIG. 49 is a view of the configuration of a shape restoring apparatus (3D model generating apparatus) 1A according to the fourth embodiment. The shape restoring apparatus 1A includes an image region mapping device 9A, a 3D model generator (generating unit) 16A, and the display unit 112, for example.

The image region mapping device 9A is configured similarly to the image region mapping device 93 and the 3D model generator 16A is configured similarly to the 3D model generator 163, but there are the following differences.

Figure 50:
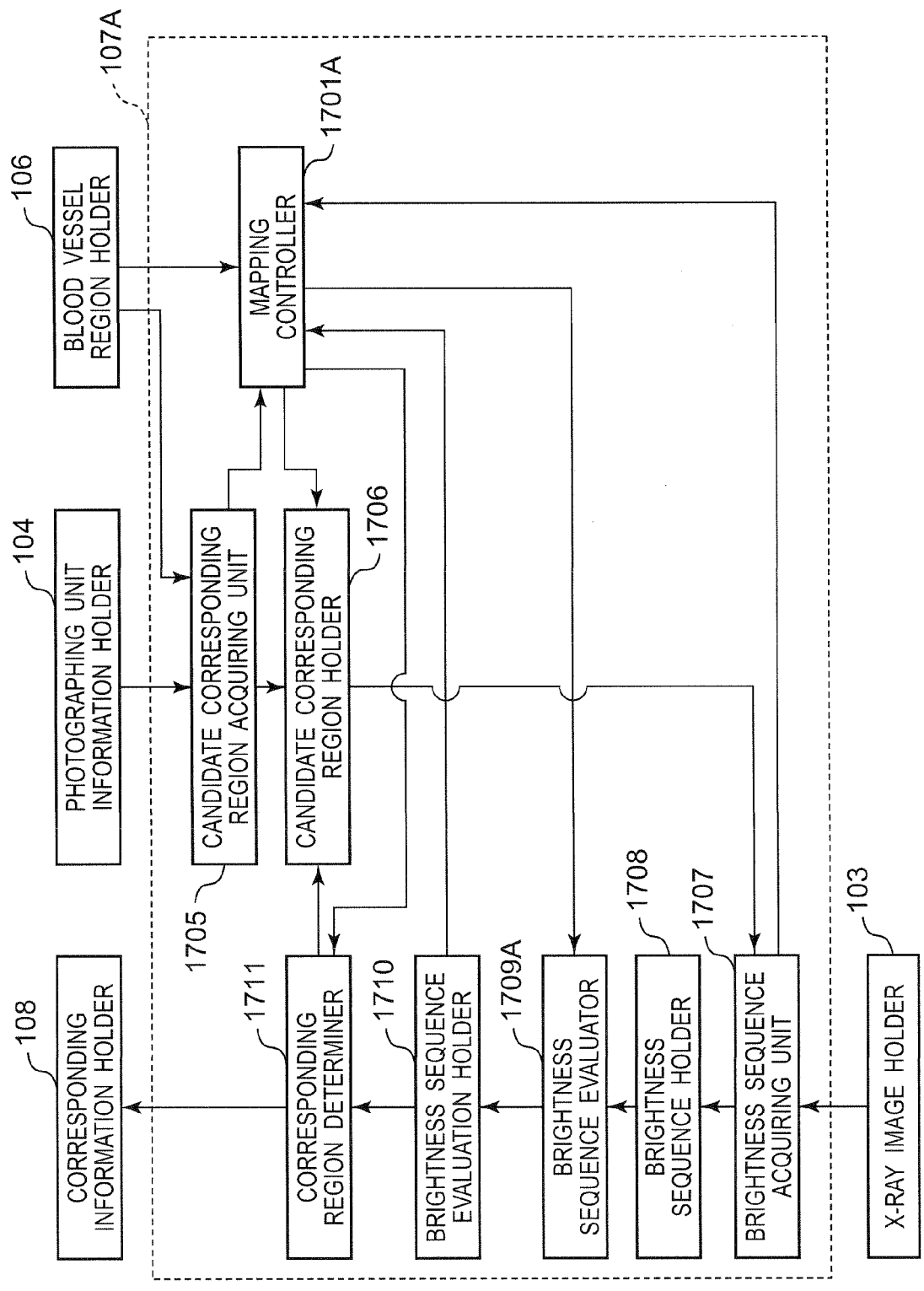
FIG. 50 is a view of the configuration of a mapping unit according to the fourth embodiment.
Figure 80:
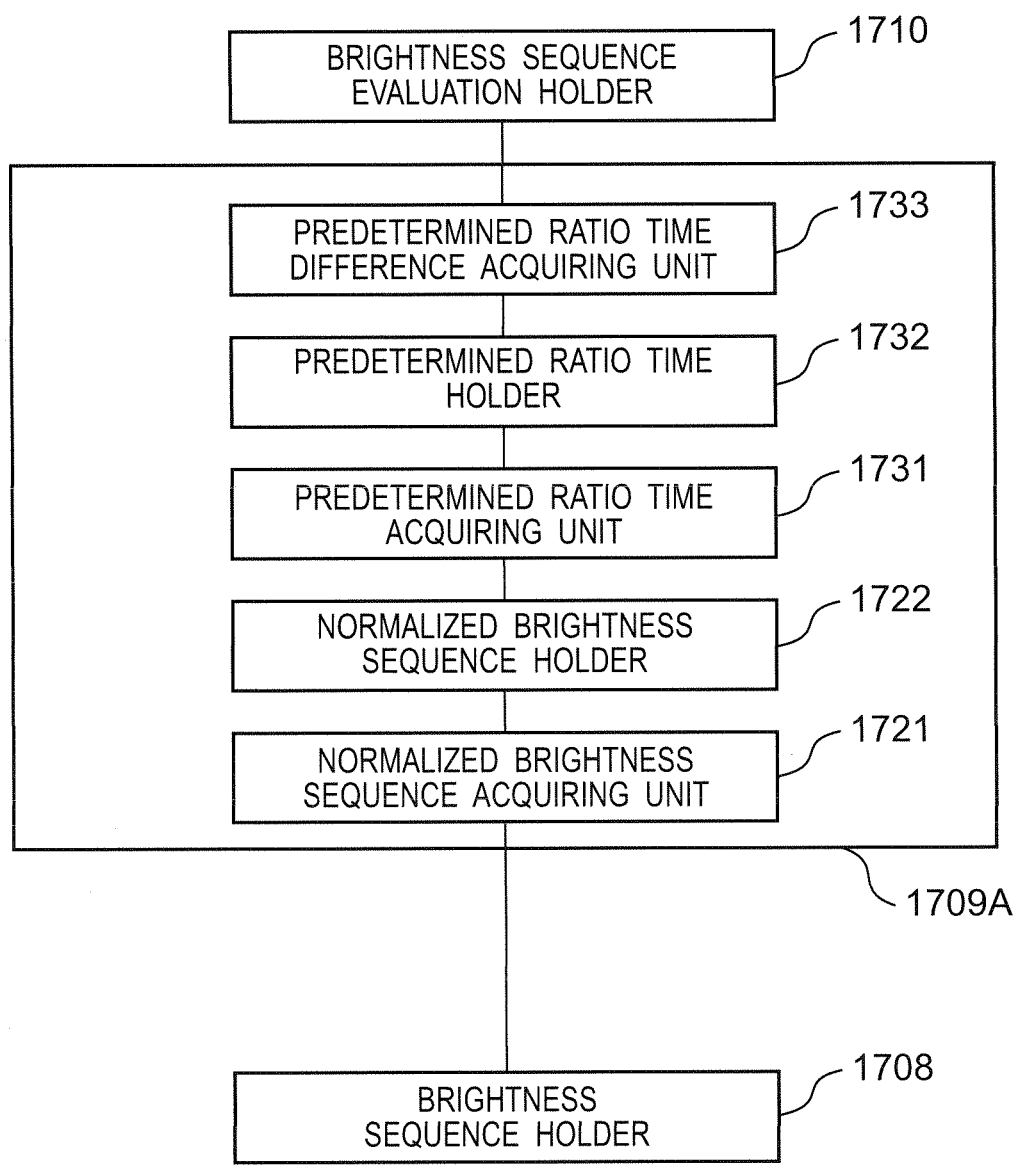
FIG. 80 is a view of the configuration of a brightness sequence evaluator in the shape restoring apparatus according to the fourth embodiment in FIG. 49.

The shape restoring apparatus 1A includes a mapping unit 107A in place of the mapping unit 107 according to the third embodiment. FIG. 50 is a view of the configuration of the mapping unit 107A. The mapping unit 107A includes a brightness sequence evaluator (evaluating unit) 1709A and a mapping controller (controlling unit) 1701A in place of the brightness sequence evaluator 1709 and the mapping controller 1701. As shown in FIG. 80, the brightness sequence evaluator 1709A includes the normalized brightness sequence acquiring unit 1721, the normalized brightness sequence holder 1722, a predetermined ratio time acquiring unit 1731, a predetermined ratio time holder (holding unit) 1732, and a predetermined ratio time difference acquiring unit 1733. The normalized brightness sequence acquiring unit 1721 and the normalized brightness sequence holder 1722 are configured similarly to the normalized brightness sequence acquiring unit 1721 and the normalized brightness sequence holder 1722 according to the third embodiment. The differences from the third embodiment are mainly described below. The configurations similar to those of the other embodiments are denoted by the same reference numerals and will not be described repeatedly where appropriate.

The predetermined ratio time acquiring unit 1731 acquires a time when the brightness of the contrast point Pk (or the candidate corresponding point Qk_n) reaches the predetermined ratio to the maximum brightness of the point from the normalized brightness sequences held by the normalized brightness sequence holder 1722, and stores the acquired time in the predetermined ratio time holder 1732. More specifically, the predetermined ratio time acquiring unit 1731 acquires the time when the brightness reaches the predetermined ratio from the normalized brightness sequence of the contrast point Pk, and stores the acquired time in the predetermined ratio time holder 1732. The predetermined ratio time acquiring unit 1731 also acquires a time when the brightness reaches the predetermined ratio from the normalized brightness sequences of the candidate corresponding points Qk_n (n=1, 2, . . . , N) of the contrast point Pk, and stores the acquired time in the predetermined ratio time holder 1732. The exemplary predetermined ratio includes two values, namely, a first predetermined ratio S_1=0.5 and a second predetermined ratio S_2=0.8.

Assume in the following description that the predetermined ratio time acquiring unit 1731 sets first predetermined ratio times to Tk_n_1 (n=1, 2, . . . , N) and second predetermined ratio times to Tk_n_2 (n=1, 2, . . . , N) for the candidate corresponding points Qk_n (n=1, 2, . . . , N). The predetermined ratio time acquiring unit 1731 also sets a first predetermined ratio time to Tk_p_1 and a second predetermined ratio time to Tk_p_2 for the contrast point Pk.

In the case of FIG. 48, the predetermined ratio time acquiring unit 1731 acquires the times 2801, 2802, and 2803 (e.g., 0.3, 0.325, and 0.366) and the times 2811, 2812, and 2813 (e.g., 0.25, 0.275, and 0.325).

The predetermined ratio time holder 1732 holds times acquired by the predetermined ratio time acquiring unit 1731. More specifically, the predetermined ratio time holder 1732 holds the first predetermined ratio time Tk_p_1 and the second predetermined ratio time Tk_p_2 for the contrast point Pk, the first predetermined ratio times Tk_n_1 (n=1, 2, . . . , N) and the second predetermined ratio times Tk_n_2 (n=1, 2, . . . , N) for the candidate corresponding points Qk_n (n=1, 2, . . . , N). FIG. 51 is an exemplary view of a data structure of the predetermined ratio times held by the predetermined ratio time holder 1732. The predetermined ratio time holder 1732 holds, at s-th line of data, s-th predetermined ratio times for the contrast point Pk and the candidate corresponding points Qk_n (n=1, 2, . . . , N; a case of n=1 and 2 is exemplified in the present embodiment) (s=1 and 2 in this case).

The predetermined ratio time difference acquiring unit 1733 acquires evaluation values for the candidate corresponding points Qk_n of the contrast point Pk in accordance with predetermined ratio times Tk_n_s (s=1, 1.1, . . . , S; where the number of predetermined ratio times S=2 in the fourth embodiment) held by the predetermined ratio time holder 1732, and stores the acquired evaluation values in the brightness sequence evaluation holder 1710. More specifically, the predetermined ratio time difference acquiring unit 1733 calculates an evaluation value in accordance with Equation 11 for each of the candidate corresponding points Qk_n (n=1, 2, . N), and stores the calculated evaluation values in the brightness sequence evaluation holder 1710.

$$H\_n = \sum_{s=1}^{S} |Tk\_p\_s - Tk\_n\_s| \qquad \text{(Equation 11)}$$

Assume that the number of predetermined ratio times S is 2 (there are two predetermined ratio times) and Equation 12 is established in the fourth embodiment.

$$H\_n = |Tk\_p\_1 - Tk\_n\_1| + |Tk\_p\_2 - Tk\_n\_2| \qquad \text{(Equation 12)}$$

In Equation 12, the first predetermined ratio time Tk_p_1 for the contrast point Pk and the first predetermined ratio time Tk_n_1 for the candidate corresponding point Qk_n have a smaller difference as these times are close to each other. The second predetermined ratio time Tk_p_2 for the contrast point Pk and the second predetermined ratio time Tk_n_2 for the candidate corresponding point Qk_n have a smaller difference as these times are close to each other. Equation 12 has the evaluation value H_n in the fourth embodiment, so that the corresponding region determiner 1711 selects a candidate corresponding point similar to brightness change information on the contrast point Pk out of the candidate corresponding points Qk_n (n=1, 2, . . . , N).

Figure 52:
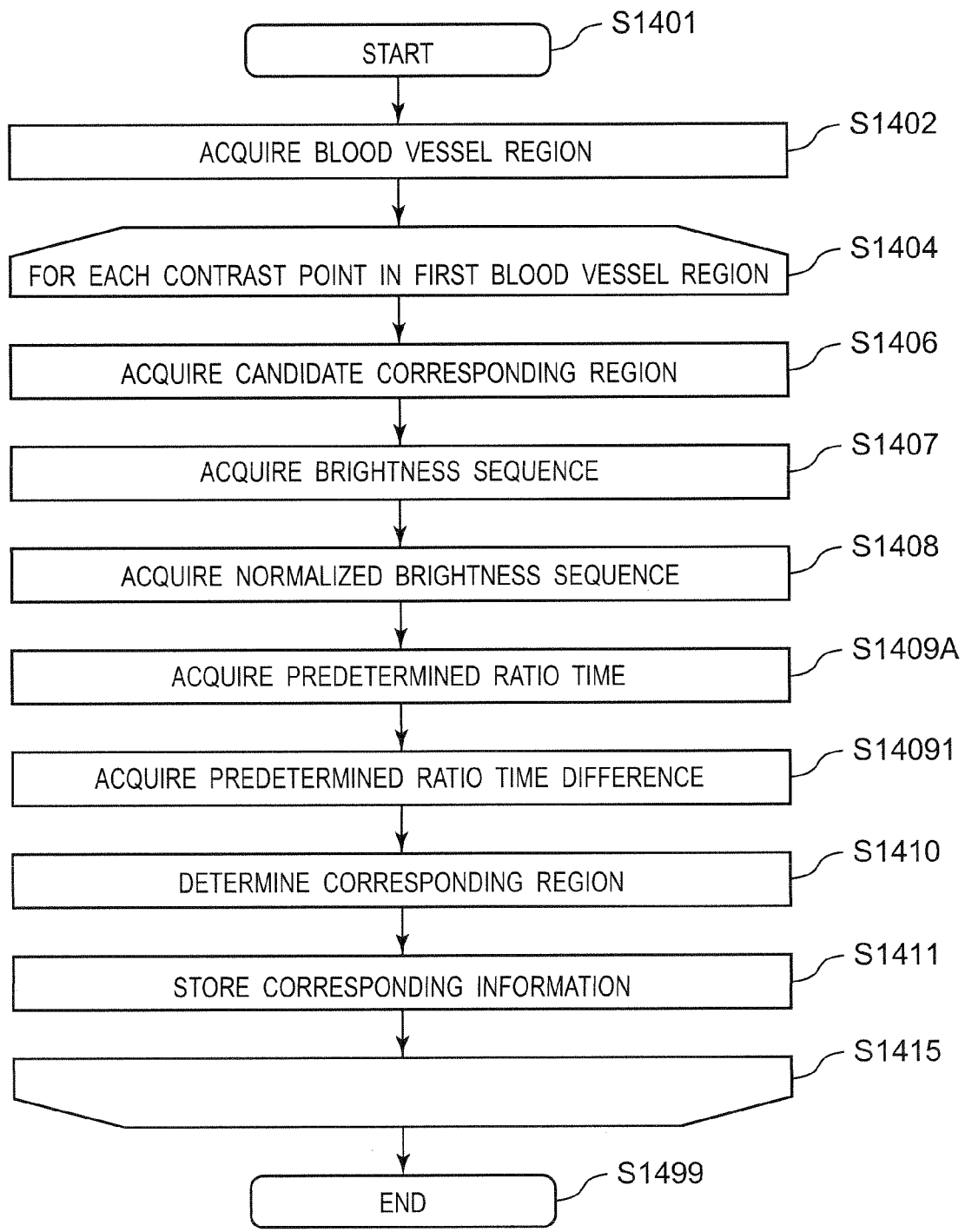
FIG. 52 is a flowchart of the mapping unit according to the fourth embodiment.

The mapping controller 1701A controls the respective units in the mapping unit 107A to execute mapping. FIG. 52 is a flowchart of a flow of the processes executed by the mapping controller 1701A. Steps S1409A and S14091 are executed in place of step S1409. The other steps are similar to those of the third embodiment and will not be described repeatedly.

In step S1409A after step S1408, the mapping controller 1701A commands the predetermined ratio time acquiring unit 1731 to execute the process. The predetermined ratio time acquiring unit 1731 executes the above-described process of the predetermined ratio time acquiring unit 1731. More specifically, the predetermined ratio time acquiring unit 1731 acquires the predetermined ratio times for the contrast point Pk and the candidate corresponding points Qk_n (n=1, 2, . . . , N), and stores the predetermined ratio times thus acquired in the predetermined ratio time holder 1732.

Then in step S14091, the mapping controller 1701A commands the predetermined ratio time difference acquiring unit 1733 to execute the process. The predetermined ratio time difference acquiring unit 1733 acquires the evaluation values for the candidate corresponding points Qk_n (n=1, 2, . . . , N) of the contrast point Pk in accordance with the predetermined ratio times Tk_n_s (s=1, 1.1, . . . , S; where the number of predetermined ratio times S=2 in the fourth embodiment) held by the predetermined ratio time holder 1732, and stores the acquired evaluation values in the brightness sequence evaluation holder 1710. The process in step S1410 is executed subsequently.

<Flow of Processes Executed by Shape Restoring Apparatus 1A>

In step S1904 in FIG. 43, the mapping unit 107A executes the above-described process of the mapping unit 107A.

More specifically, the mapping unit 107A determines the corresponding point Qk of each of the contrast points Pk in the contrast region and stores corresponding information in the corresponding information holder 108. The other steps are similar to those of the third embodiment.

The corresponding information holder 108 can alternatively store the positions of the contrast point Pk and the corresponding point Qk as well as a difference Sk between the second predetermined ratio time and the first predetermined ratio time for the contrast point Pk or the corresponding point Qk. The difference Sk has a smaller value at a portion with a fast blood flow and has a larger value at a portion with a slow blood flow. Acquisition of the difference Sk enables acquisition of appropriate blood speed at the contrast point Pk. The display screen generator 111 generates a display screen in accordance with the blood speed. More specifically, the display screen generator 111 can generate a display screen that includes a yellow region indicating a blood vessel having the difference Sk larger than a first predetermined value and a red region indicating the remaining portion. Such display enables an indication of the blood vessel having a fast flow. Furthermore, the display screen generator 111 can generate a display screen that includes a blue region indicating a blood vessel having the difference Sk smaller than a second predetermined value. Such display enables an indication of the blood vessel having a slow flow.

<Effects of the Fourth Embodiment>

The fourth embodiment exerts effects similar to those of the third embodiment.

The radiographing units 101 and 102 capture the state of increase in amount of the contrast medium for a radiographing device in the present embodiment. The radiographing units 101 and 102 can alternatively capture the state of decrease in amount of the contrast medium. Acquired in this case is not the first time when the normalized brightness sequence has brightness larger than a predetermined ratio but the first time when the normalized brightness sequence has brightness lower than the predetermined ratio.

(Fifth Embodiment)

In the third embodiment, the predetermined ratio time is acquired from each of the candidate corresponding points Qk_n (n=1, 2, ..., N) and the candidate corresponding point Qk_x having a predetermined ratio time close to that of the contrast point Pk is selected as the corresponding point Qk from the candidate corresponding points Qk_n.

Acquired in the fifth embodiment of the present disclosure is not the predetermined ratio time but a peak time for a differential brightness sequence. A differential brightness sequence is a sequence of a value obtained by differentiating a brightness sequence, and the differential brightness sequence has the maximum value at the peak time. In the fifth embodiment, a peak time for each of the candidate corresponding points Qk_n (n=1, 2, ..., N) is acquired and the candidate corresponding point having a peak time close to that of the contrast point Pk is selected as the corresponding point Qk from the candidate corresponding points Qk_n.

Figure 53:
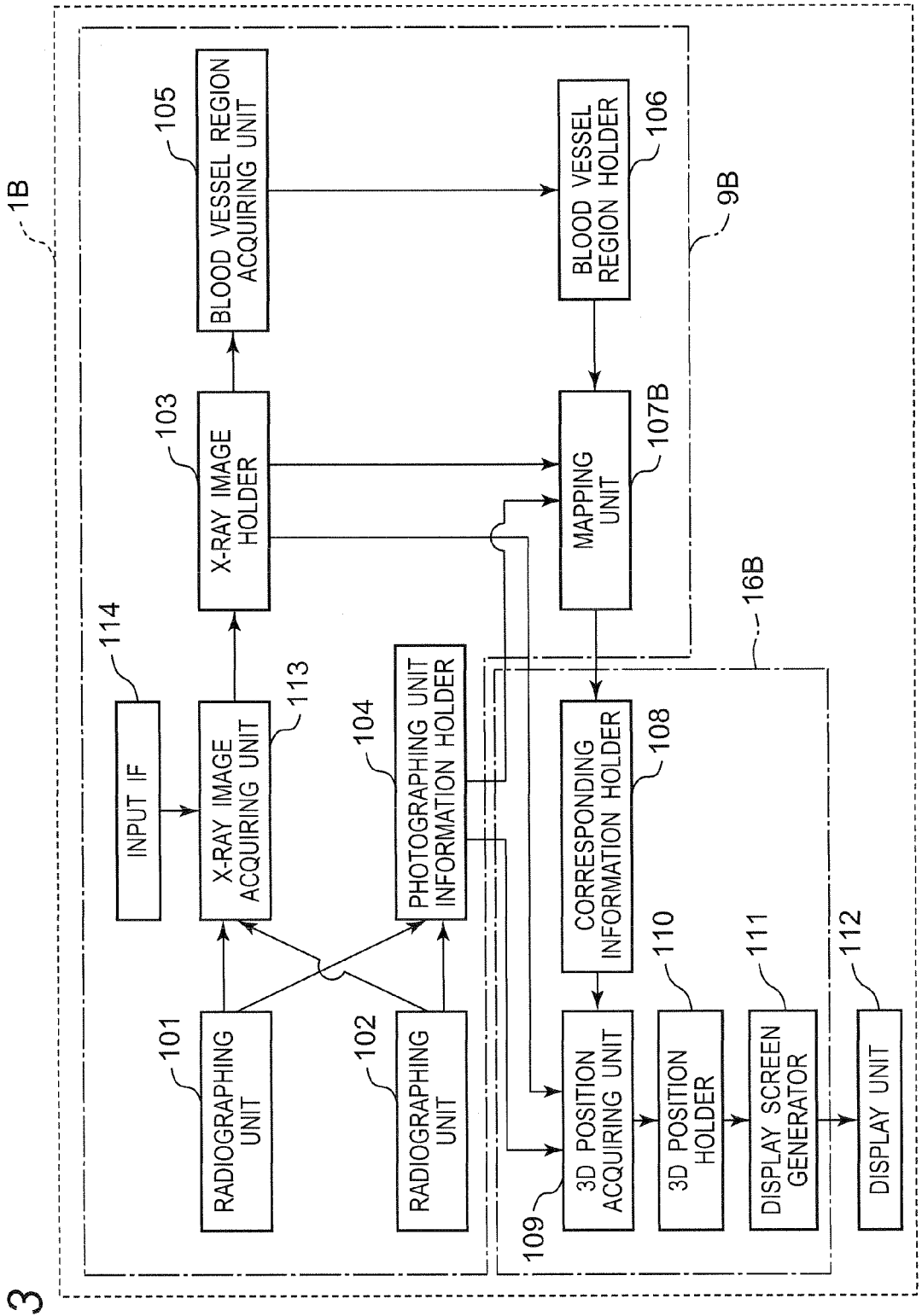
FIG. 53 is a view of the configuration of a shape restoring apparatus according to a fifth embodiment.

FIG. 53 is a view of the configuration of a shape restoring apparatus (3D model generating apparatus) 1B according to the fifth embodiment. The shape restoring apparatus 1B includes an image region mapping device 9B, a 3D model generator (generating unit) 16B, and the display unit 112, for example.

The image region mapping device 9B is configured similarly to the image region mapping device 93 shown in FIG. 21 and the 3D model generator 16B is configured similarly to the 3D model generator 163 shown in FIG. 21, but there are the following differences.

Figure 54:
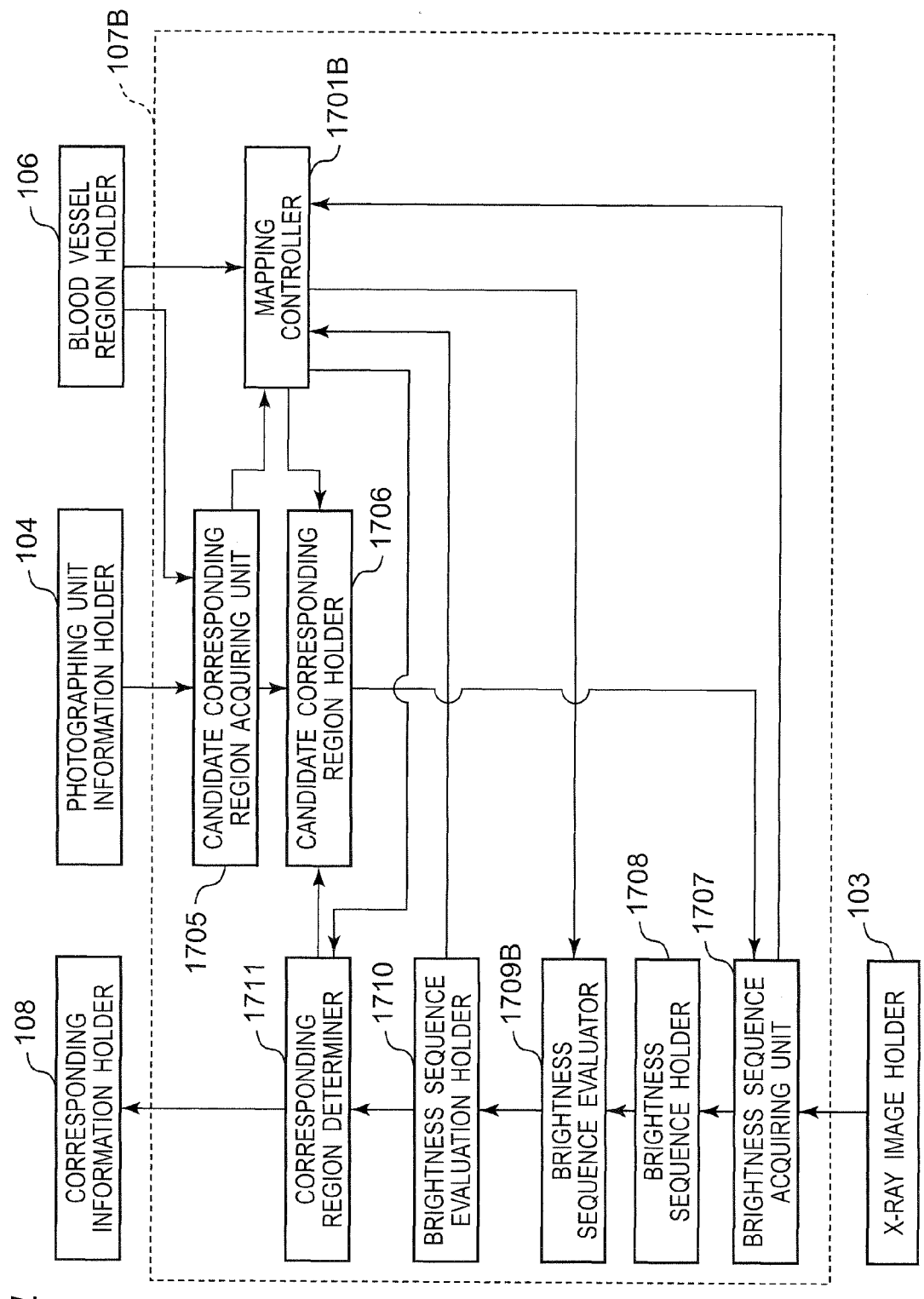
FIG. 54 is a view of the configuration of a mapping unit according to the fifth embodiment.

The shape restoring apparatus 1B includes a mapping unit 107B in place of the mapping unit 107 according to the third embodiment. FIG. 54 is a view of the configuration of the mapping unit 107B. The mapping unit 107B includes a mapping controller (controlling unit) 1701B and a brightness sequence evaluator (evaluating unit) 1709B in place of the mapping controller 1701 and the brightness sequence evaluator 1709. The configurations similar to those of the other embodiments are denoted by the same reference numerals and will not be described repeatedly where appropriate.

Figure 55:
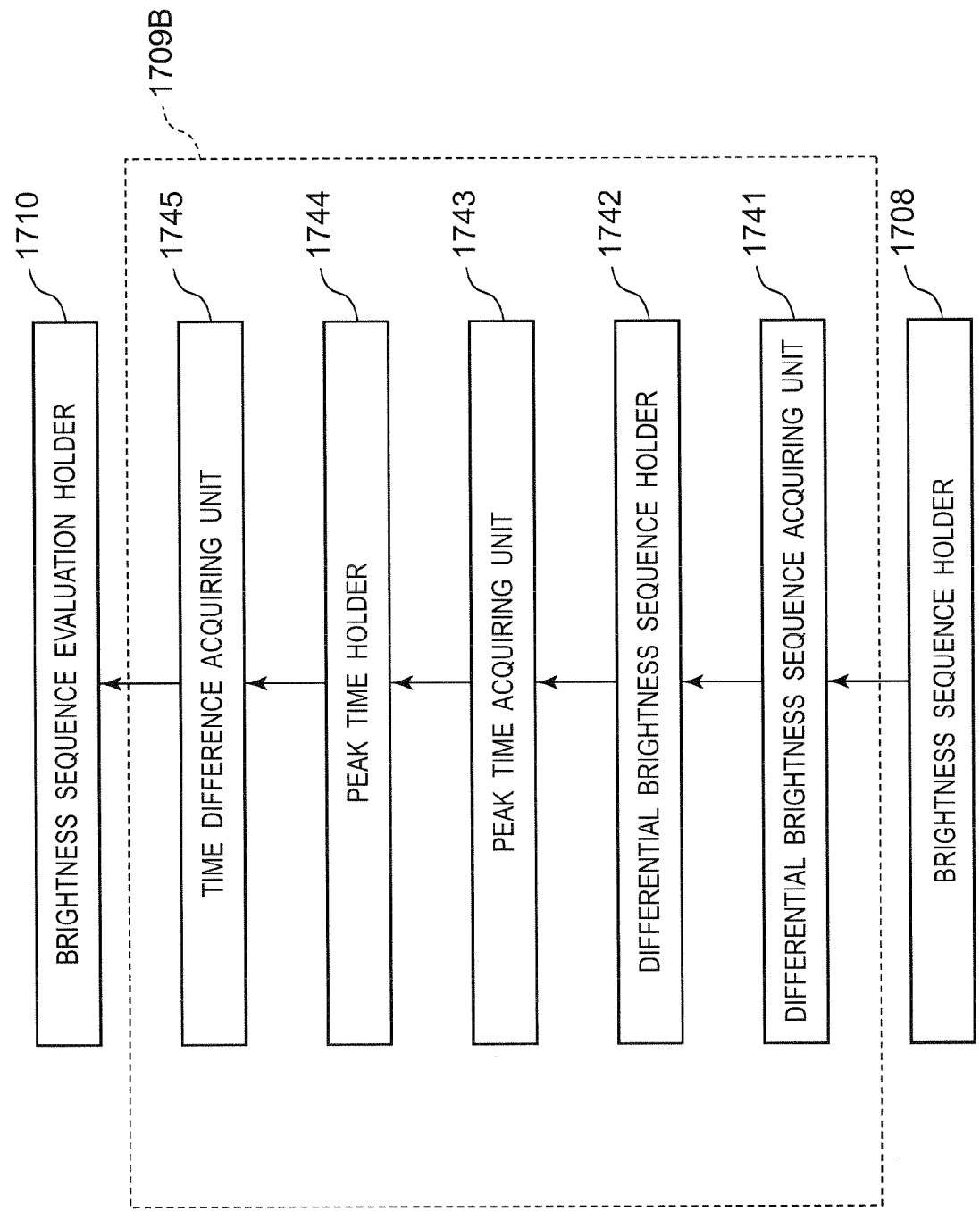
FIG. 55 is a view of the configuration of a brightness sequence evaluator according to the fifth embodiment.

The brightness sequence evaluator 1709B evaluates the candidate corresponding points Qk_n (n=1, 2, ..., N). FIG. 55 shows the configuration of the brightness sequence evaluator 1709B. The brightness sequence evaluator 1709B includes a differential brightness sequence acquiring unit 1741, a differential brightness sequence holder (holding unit) 1742, a peak time acquiring unit 1743, a peak time holder (holding unit) 1744, and a time difference acquiring unit 1745.

The differential brightness sequence acquiring unit 1741 differentiates the brightness sequence held by the brightness sequence holder 1708 to generate a differential brightness sequence and stores the differential brightness sequence thus generated in the differential brightness sequence holder 1742.

Figure 57:
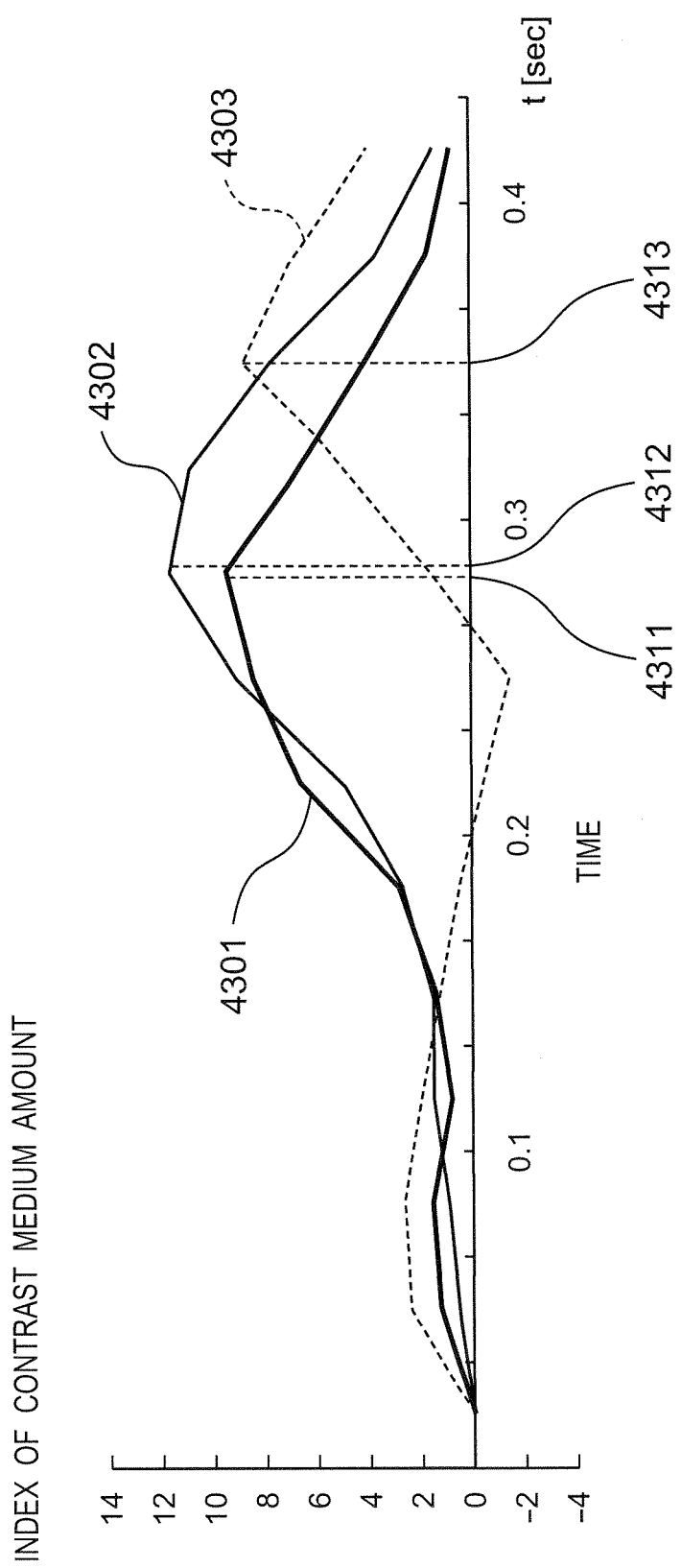
FIG. 57 is a graph indicating differential brightness sequences of the contrast point Pk and the candidate corresponding points Qk_1 and Qk_2 according to the fifth embodiment.

For simplification of the process, assume that the differential brightness sequence has the value of 0 at the time 0 and the differential brightness sequence has a value of L_Pk_t−L_Pk_(t−1) at a time t. More specifically, assume that the differential brightness sequence at the time t is the difference between the value of the brightness sequence at the time t and the value of the brightness sequence at a time (t−1). FIG. 56 exemplarily shows a data structure of differential brightness sequences in a case where brightness sequences have the values indicated in FIG. 24. FIG. 56 indicates only the differential brightness sequences of the contrast point Pk and the candidate corresponding point Qk_2 due to the limited space in the drawing sheet. FIG. 57 is a graph indicating differential brightness sequences of the contrast point Pk and the corresponding points Qk and Qx (x≠k) for the brightness sequences indicated in FIG. 56. In FIG. 57, a thick line 4301, a solid line 4302, and a dotted line 4303 indicate the differential brightness sequence of the contrast point Pk, the differential brightness sequence of the candidate corresponding point Qk_1 of the contrast point Pk (the corresponding point Qk of the contrast point Pk), and the differential brightness sequence of the candidate corresponding point Qk_2 of the contrast point Pk (the corresponding point Qx of a contrast point Px (x≠k)), respectively.

Alternatively, the differential brightness sequence acquiring unit 1741 can smooth the brightness sequences held by the brightness sequence holder 1708 and then acquire the differential brightness sequences. Still alternatively, the differential brightness sequence acquiring unit 1741 can smooth the differential brightness sequences thus acquired and store the differential brightness sequences thus smoothed in the differential brightness sequence holder 1742.

The differential brightness sequence holder 1742 holds the differential brightness sequences generated by the differential brightness sequence acquiring unit 1741. The differential brightness sequence holder 1742 holds the differential brightness sequences having the data structure shown in FIG. 56, for example. The differential brightness sequence holder 1742 holds the differential brightness sequences indicated in the graph in FIG. 57, for example.

The peak time acquiring unit 1743 acquires peak time(s) each having the maximum differential brightness from the differential brightness sequences held by the differential brightness sequence holder 1742, and stores the peak time(s) in the peak time holder 1744. For example, the peak time acquiring unit 1743 acquires peak times 4311 to 4313 indicated in FIG. 57 and stores the peak times 4311 to 4313 in the peak time holder 1744.

Figure 58:
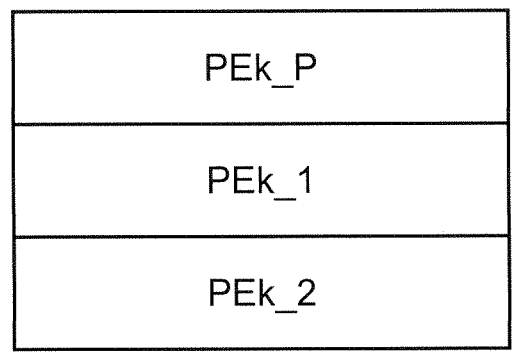
FIG. 58 is a view of a data structure of a peak time holder according to the fifth embodiment.
Figure 59:
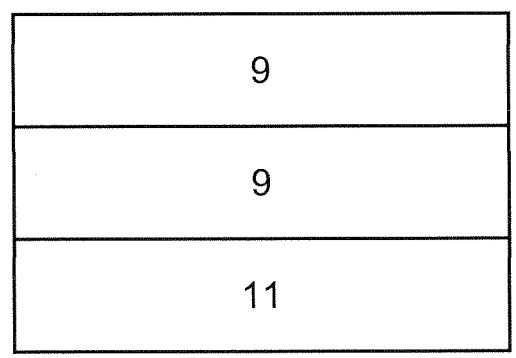
FIG. 59 is an exemplary view of data held by the peak time holder according to the fifth embodiment.

The peak time holder 1744 holds the peak times for the differential brightness sequences acquired by the differential brightness sequence acquiring unit 1741. FIG. 58 is a view of a data structure of the peak time holder 1744. The peak time holder 1744 holds a peak time PEk_p for the contrast point Pk and a peak time PEk_n for each of the candidate corresponding points Qk_n (n=1, 2, ..., N) of the contrast point Pk. FIG. 58 indicates the structure in the case of N=2. FIG. 59 is an exemplary view of data held by the peak time holder 1744. FIG. 59 indicates the peak times held in the case of the differential brightness sequences indicated in FIG. 57.

The time difference acquiring unit 1745 calculates the evaluation values for the candidate corresponding points Qk_n (n=1, 2, ..., N) in accordance with the peak times held by the peak time holder 1744. The evaluation values are calculated in accordance with Equation 13.

$$H\_n = |PEk\_p - PEk\_n| \quad \text{(Equation 13)}$$

More specifically, the time difference acquiring unit 1745 regards as an evaluation value a difference between the peak time PEk_p for the contrast point Pk and each of the peak time PEk_n for the candidate corresponding points Qk_n (n=1, 2, ..., N). When the peak times are indicated in FIG. 59, $H\_1 = |9-9| = 0$ and $H\_2 = |9-11| = 2$ are established.

According to Equation 13, the evaluation value is smaller as the peak time PEk_p for the contrast point Pk is close to the peak time PEk_n for the candidate corresponding point Qk_n. In the fifth embodiment, the evaluation values are calculated in accordance with Equation 13, and a candidate corresponding point having a brightness change similar to that of the contrast point Pk is selected from the candidate corresponding points Qk_n.

Figure 60:
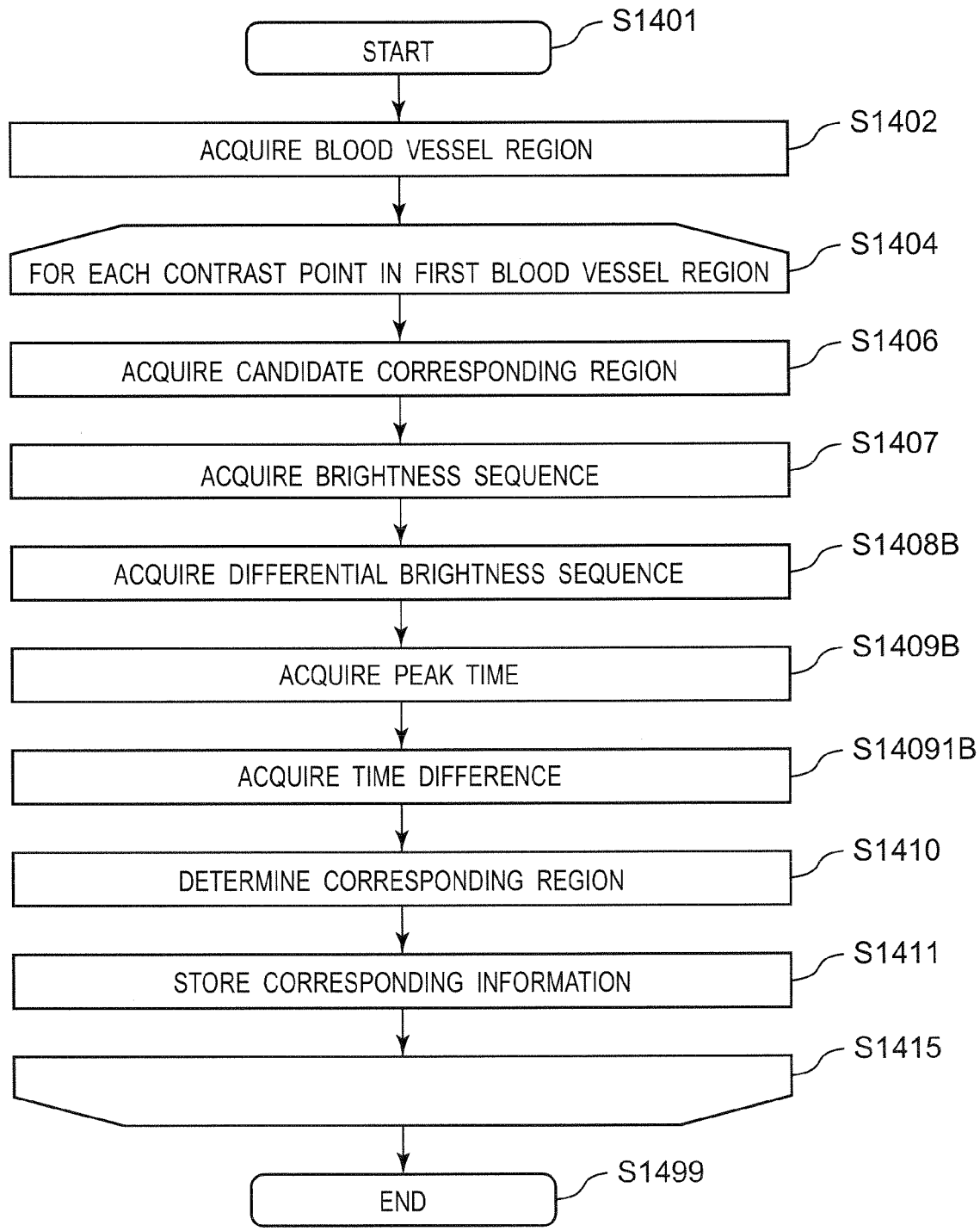
FIG. 60 is a flowchart of the mapping unit according to the fifth embodiment.

The mapping controller 1701B controls the respective units in the mapping unit 107B to execute mapping. FIG. 60 is a flowchart of a flow of the processes executed by the mapping controller 1701B. The mapping controller 1701B executes steps S1408B, S1409B, and S14091B in place of steps S1408 and 1409 in FIG. 39 executed by the mapping controller 1701 according to the third embodiment. The other steps are similar to those of the third embodiment and will not be described repeatedly.

In step S1408B subsequent to step S1407, the differential brightness sequence acquiring unit 1741 executes the above-described process of the differential brightness sequence acquiring unit 1741. More specifically, the differential brightness sequence acquiring unit 1741 generates the differential brightness sequences by differentiating the brightness sequences held by the brightness sequence holder 1708 to acquire the differential brightness sequences of the contrast point Pk and the candidate corresponding point Qk_n, and stores the differential brightness sequences in the differential brightness sequence holder 1742.

In step S1409B, the peak time acquiring unit 1743 executes the above-described process of the peak time acquiring unit 1743. More specifically, the peak time acquiring unit 1743 acquires the peak times PEk_p and PEk_n (n=1, 2, ..., N) each having the maximum differential brightness from the differential brightness sequences held by the differential brightness sequence holder 1742, and stores the peak times in the peak time holder 1744.

In step S14091B, the time difference acquiring unit 1745 executes the above-described process of the time difference acquiring unit 1745. More specifically, the time difference acquiring unit 1745 calculates the evaluation values H_n for the candidate corresponding points Qk_n (n=1, 2, ..., N) in accordance with the peak times held by the peak time holder 1744. The process in step S1410 is executed subsequently.

<Flow of Processes Executed by Shape Restoring Apparatus 1B>

In step S1904 in FIG. 43, the mapping unit 107B executes the above-described process of the mapping unit 107B. More specifically, the mapping unit 107B determines the corresponding point Qk of each of the contrast points Pk in the contrast region and stores corresponding information in the corresponding information holder 108. The other steps are similar to those of the third embodiment.

<Effects of the Fifth Embodiment>

The fifth embodiment exerts effects similar to those of the third embodiment.

The radiographing units 101 and 102 capture the state of increase in amount of the contrast medium for a radiographing device in the present embodiment. The radiographing units 101 and 102 can alternatively capture the state of decrease in amount of the contrast medium. Acquired in this case is not a time having the maximum differential brightness sequence but a time having the minimum differential brightness sequence.

(Sixth Embodiment)

A shape restoring apparatus (3D model generating apparatus) 1C according to the sixth embodiment of the present disclosure that restores shapes of a plurality of blood vessels that overlap each other and appear as a single blood vessel on an image captured by the radiographing unit 101 (or 102) will be explained.

Figure 61:
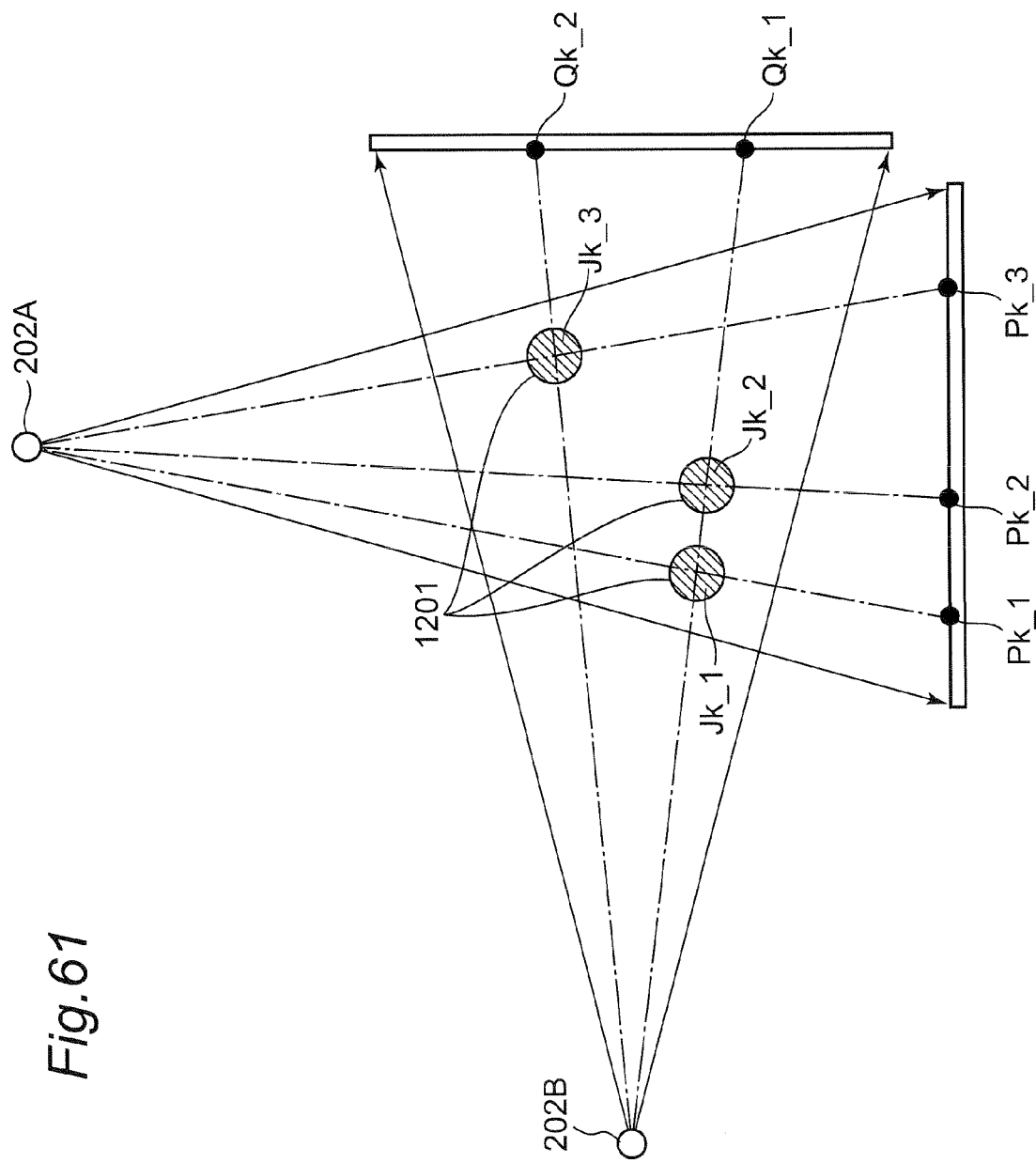
FIG. 61 is a view of an epipolar plane according to a sixth embodiment.

FIG. 61 shows an epipolar section in a case where two blood vessels 1201 overlap each other on an image captured by the radiographing unit 102. An X-ray generated by the X-ray generator 202B in the radiographing unit 102 and having passed a 3D point Jk_1 of a first one of the blood vessels 1201 further passes a 3D point Jk_2 of a second one of the blood vessels 1201 and reaches the corresponding point Qk_1. An X-ray generated by the X-ray generator 202B in the radiographing unit 102 and having passed a 3D point Jk_3 reaches the corresponding point Qk_2. An X-ray generated by the X-ray generator 202A in the radiographing unit 101 and having passed the 3D point Jk_1 is projected at a contrast point Pk_1 on the captured image. An X-ray generated by the X-ray generator 202A and having passed the 3D point Jk_2 is projected at a contrast point Pk_2 on the captured image. An X-ray generated by the X-ray generator 202A in the radiographing unit 101 and having passed the 3D point Jk_3 is projected at a first image projection point Pk_3 on the captured image.

Figure 62:
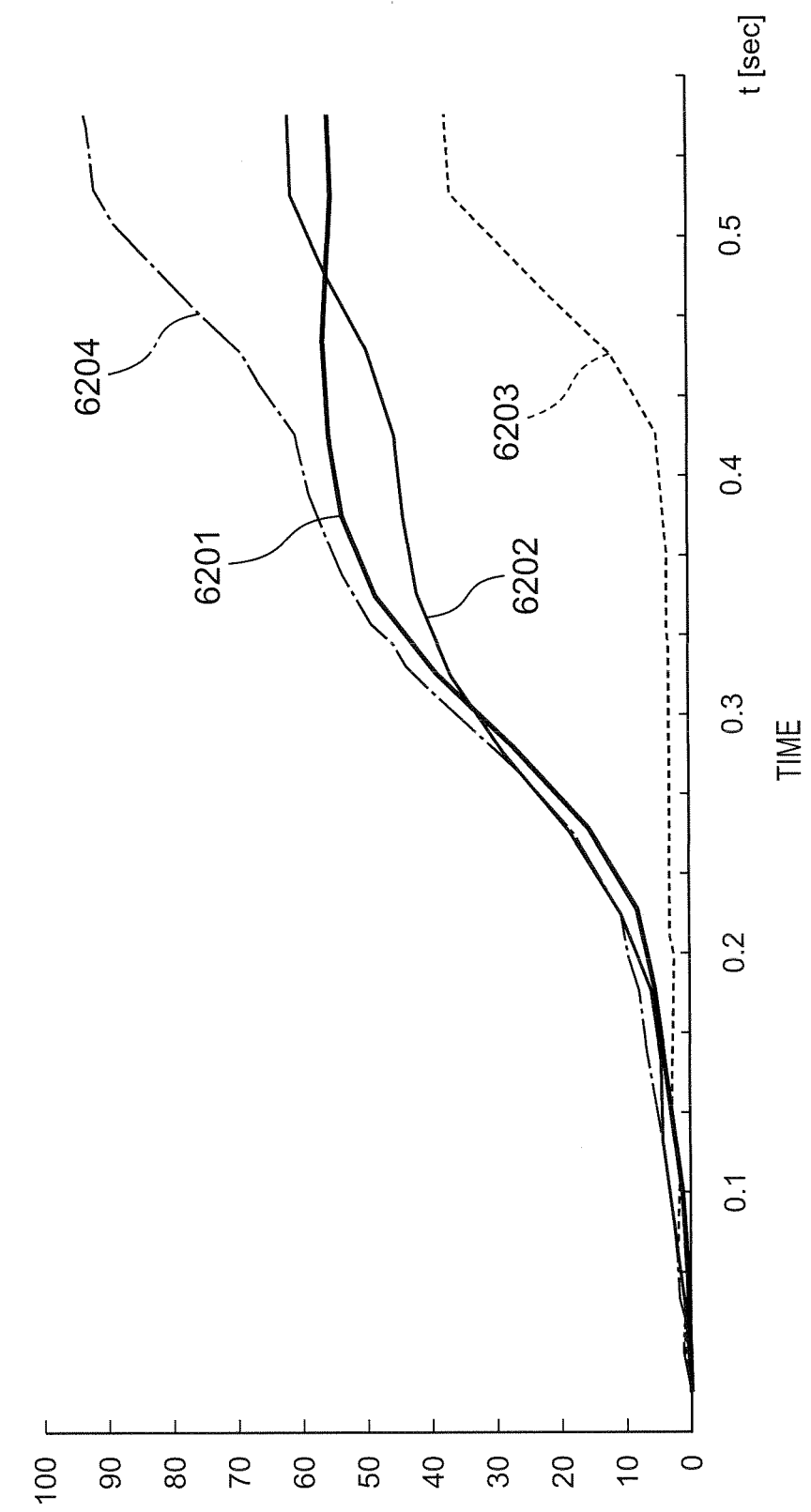
FIG. 62 is a graph indicating brightness sequences of contrast points Pk_1 to Pk_3 and the candidate corresponding points Qk_1 and Qk_2 according to the sixth embodiment.
Figure 63:
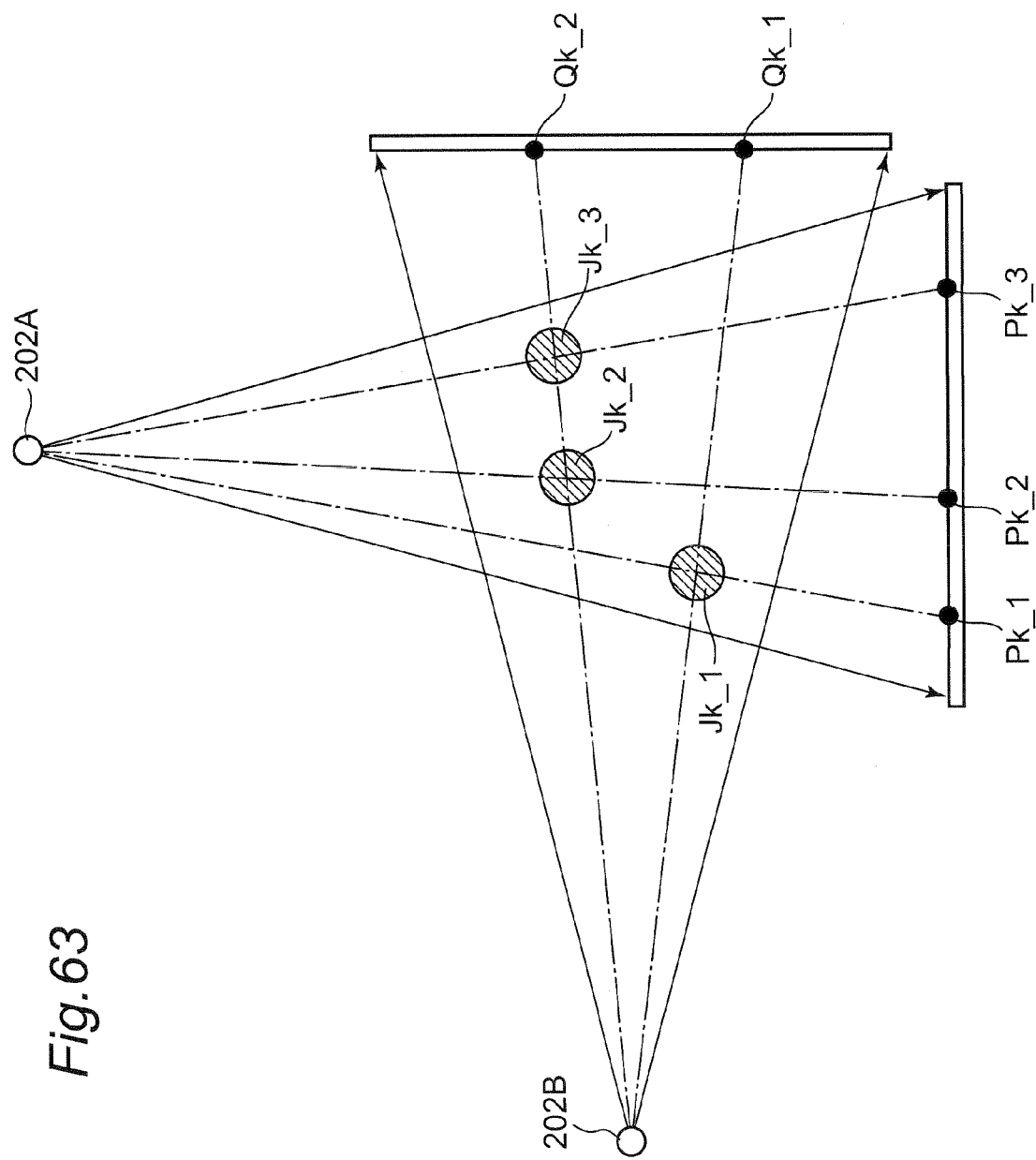
FIG. 63 is a view of an epipolar plane according to the sixth embodiment.
Figure 64:
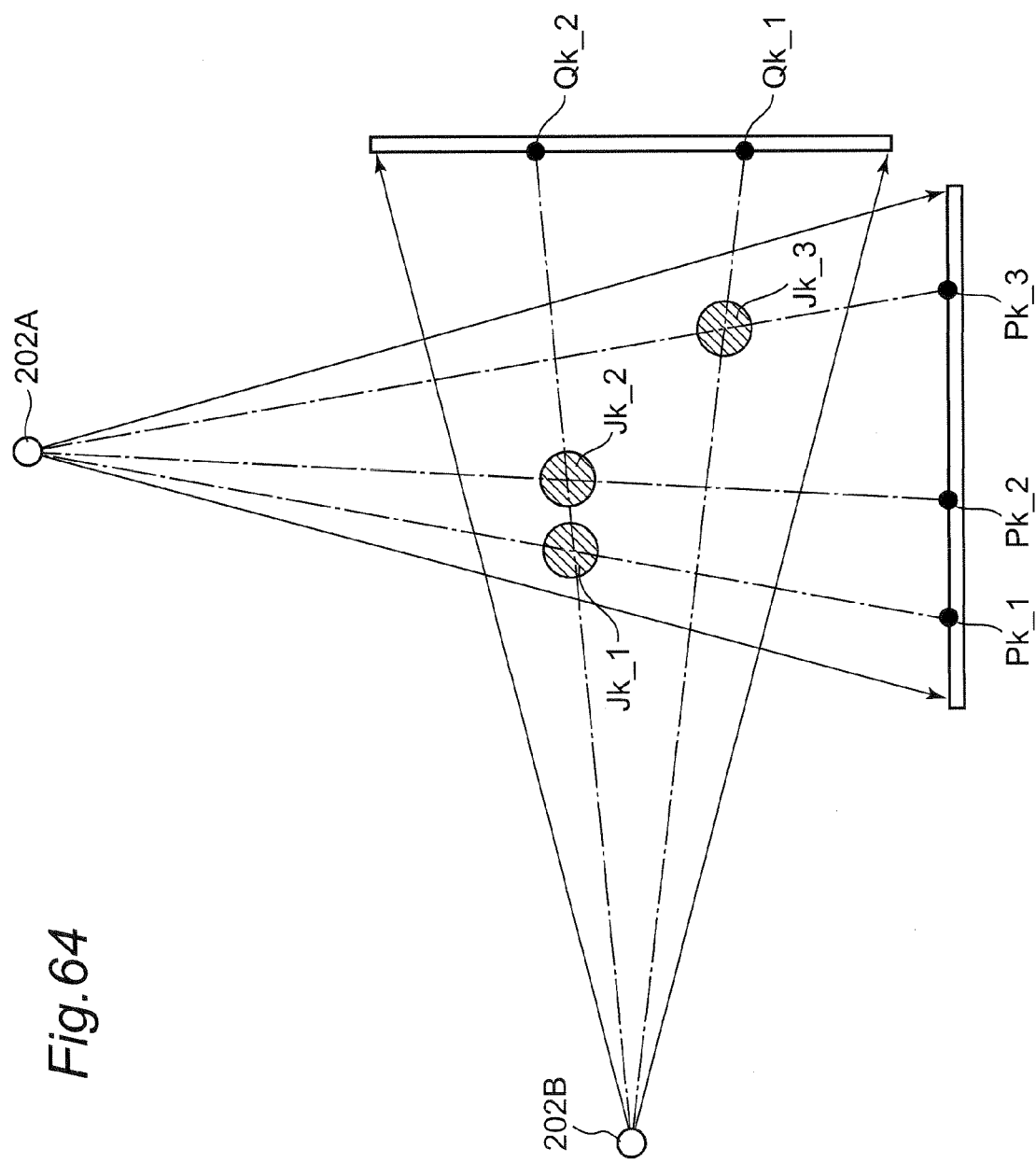
FIG. 64 is a view of an epipolar plane according to the sixth embodiment.
Figure 65:
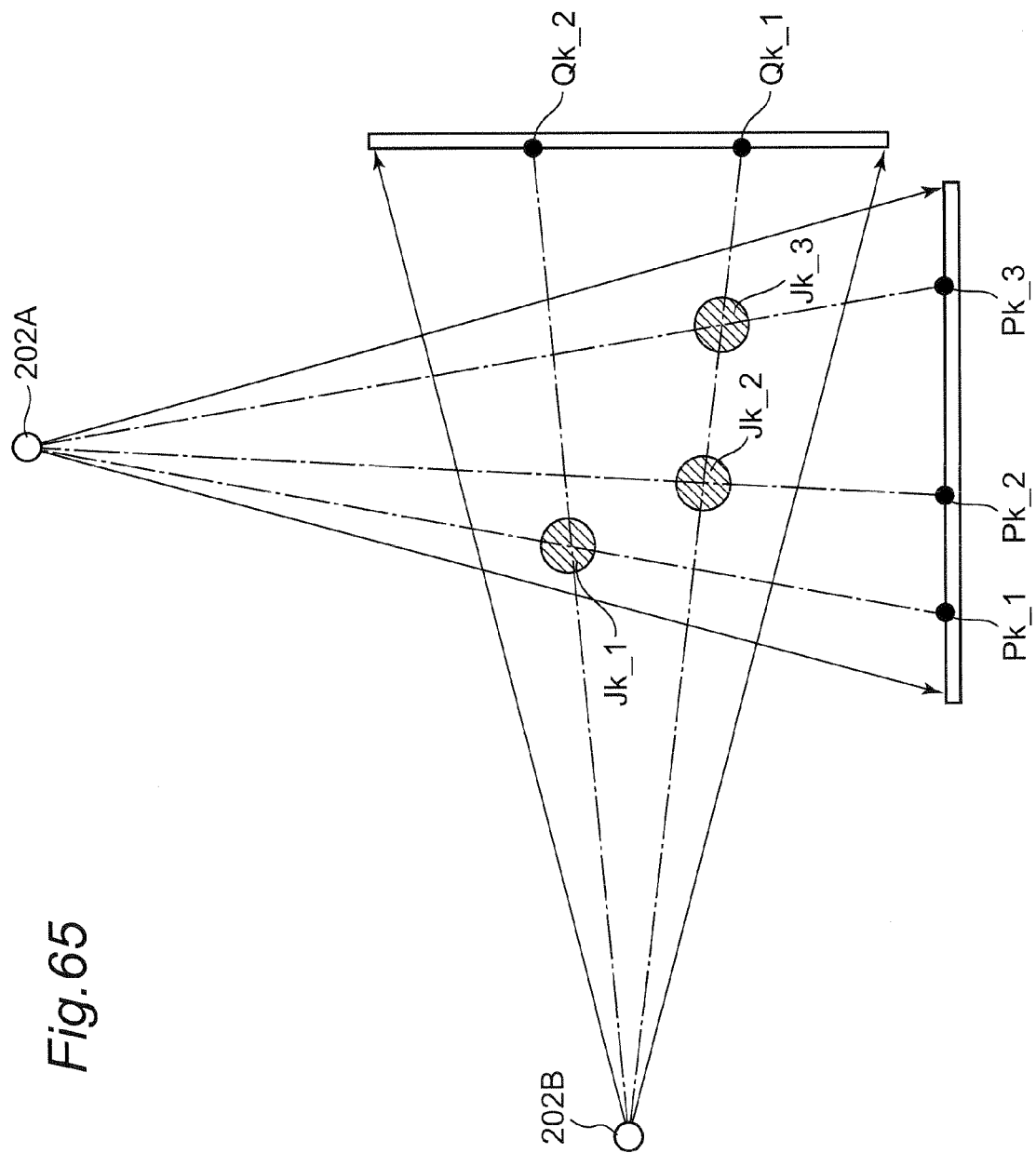
FIG. 65 is a view of an epipolar plane according to the sixth embodiment.
Figure 66:
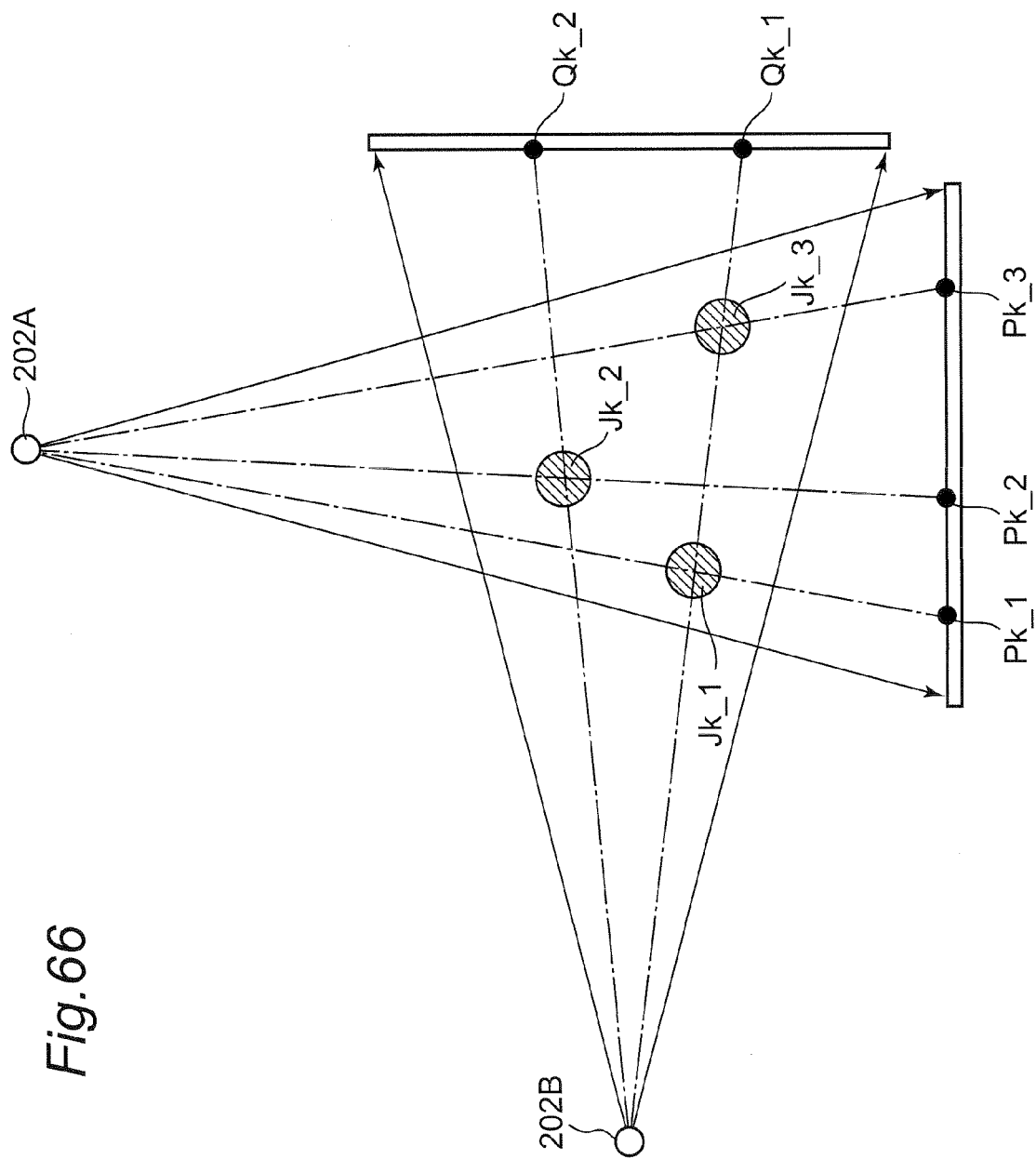
FIG. 66 is a view of an epipolar plane according to the sixth embodiment.
Figure 67:
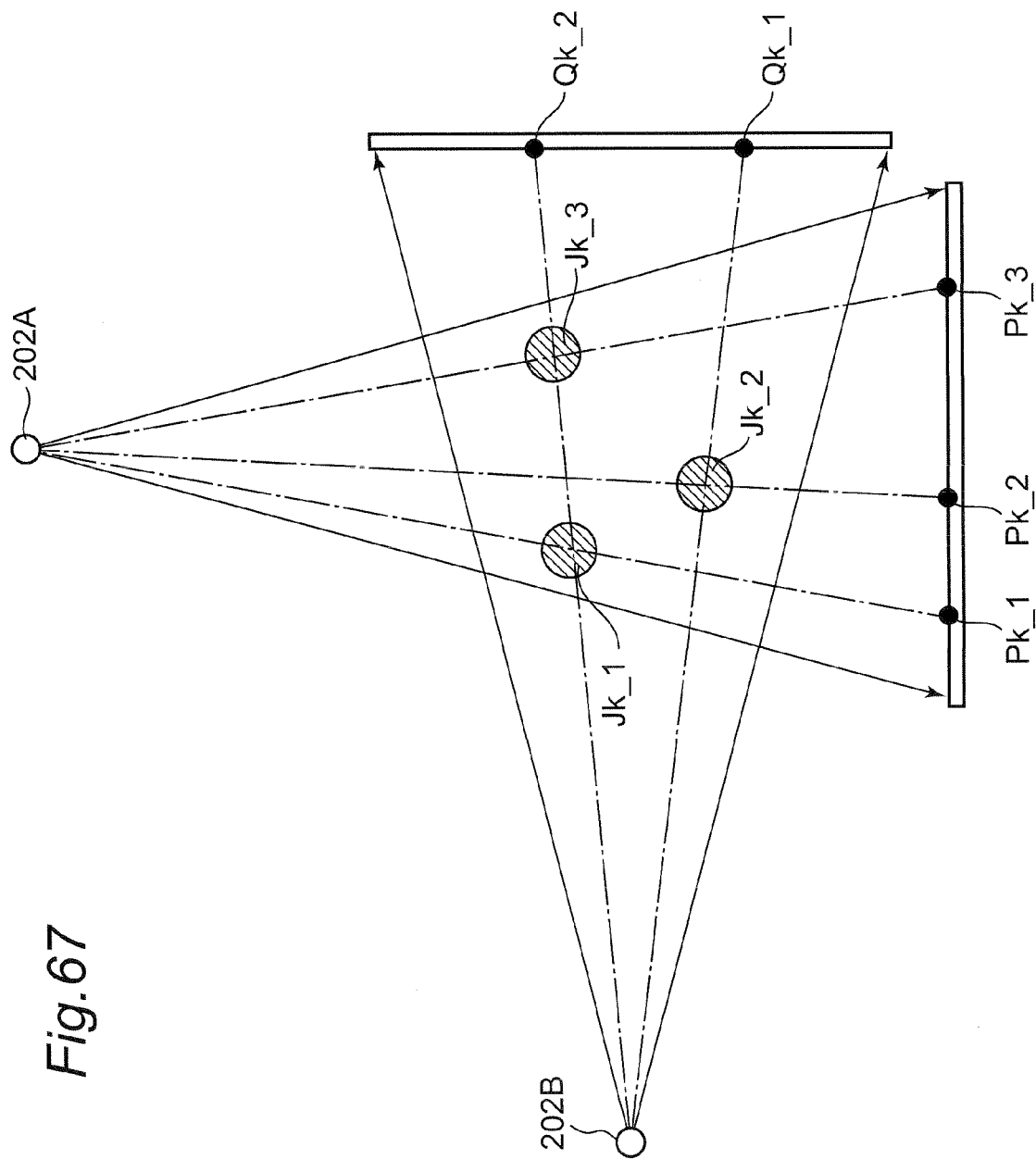
FIG. 67 is a view of an epipolar plane according to the sixth embodiment.

FIG. 62 is a graph indicating brightness sequences of the contrast points Pk_1 and Pk_2 and the corresponding point Qk_1 in FIG. 61. In FIG. 62, a thick line 6201 indicates a brightness change of the contrast point Pk_1, a dotted line 6203 indicates a brightness change of the contrast point Pk_2, and a solid line 6202 indicates a brightness change of the corresponding point Qk_1. The blood vessels 1201 overlap each other, and the brightness sequence of the corresponding point Qk_1 and the brightness sequence of the contrast point Pk_1 are increased and decreased at different degrees. Furthermore, the brightness sequence of the corresponding point Qk_1 and the brightness sequence of the contrast point Pk_2 are increased and decreased at different degrees.

When the contrast medium increases in amount at the 3D point Jk_1 indicated in FIG. 61, the contrast point Pk_1 and the corresponding point Qk_1 are darker (with a larger brightness difference). When the contrast medium increases in amount at the 3D point Jk_2, the contrast point Pk_2 and the corresponding point Qk_1 are darker (with a larger brightness difference). In this manner, the brightness change at the corresponding point Qk_1 is relevant to both of the brightness change at the contrast point Pk_1 and the brightness change at the contrast point Pk_2.

The shape restoring apparatus 1C according to the sixth embodiment thus compares a normalized brightness sequence of the sum of brightness of a plurality of contrast points with a normalized brightness sequence of the candidate corresponding point to execute mapping. In the case of FIG. 61, a normalized brightness sequence of the sum of the contrast points Pk_1 and Pk_2 is compared with the normalized brightness sequence of the corresponding point Qk_1. In FIG. 62, a dashed line 6204 indicates a brightness sequence of the sum of a brightness value of the contrast point Pk_1 and a brightness value of the contrast point Pk_2. The dashed line 6204 is increased and decreased at a degree similar to that of the solid line 6202.

In the following description, a projection point on the first blood vessel region image 1101 is called a candidate corresponding point (with no specification of a corresponding point of which point). When a normalized brightness sequence of the sum of contrast points Pk_x and Pk_y and a normalized brightness sequence of a candidate corresponding point Qk_z are compared with each other, description is simplified such that [{x, y}, {z}] are compared as a group.

The blood vessels 1201 shown in FIG. 61 are projected at the contrast points Pk_1 to Pk_3 on an image captured by the radiographing unit 101 and are projected at the candidate corresponding points Qk_1 and Qk_2 on an image captured by the radiographing unit 102. In addition to the case of FIG. 61, there may be a blood vessel that is projected at the same position as the case of FIG. 61. More specifically, also when the 3D points Jk_1 to Jk_3 are located at the positions indicated in FIGS. 63 to 67, the contrast points and the candidate corresponding points appear at similar positions. (Although there may be additionally specific locations in actual cases, such cases will not be considered in the present embodiment.) The shape restoring apparatus 1C can extract a set of the projection point and the corresponding point of the blood vessel to be restored in shape from these blood vessels, and accurately restore the shape of the blood vessel.

<Configuration According to the Sixth Embodiment>

Figure 68:
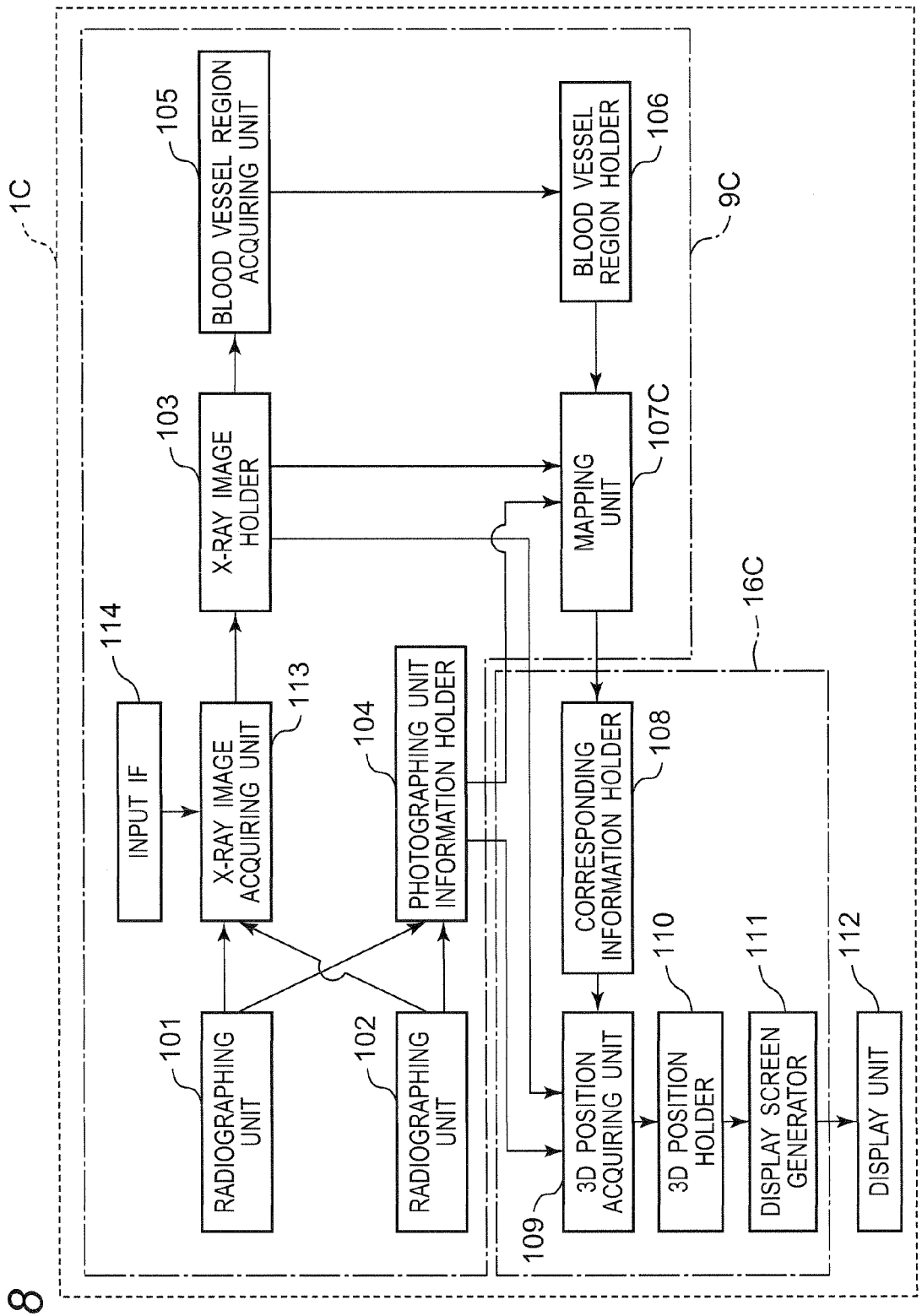
FIG. 68 is a view of the configuration of a shape restoring apparatus according to the sixth embodiment.

FIG. 68 is a view of the configuration of the shape restoring apparatus 1C according to the sixth embodiment. The shape restoring apparatus 1C includes an image region mapping device 9C, a 3D model generator (generating unit) 16C, and the display unit 112, for example.

The image region mapping device 9C is configured similarly to the image region mapping device 93 shown in FIG. 21 and the 3D model generator 16C is configured similarly to the 3D model generator 163 shown in FIG. 21, but there are the following differences. The configurations similar to those of the other embodiments are denoted by the same reference numerals and will not be described repeatedly where appropriate.

Figure 69:
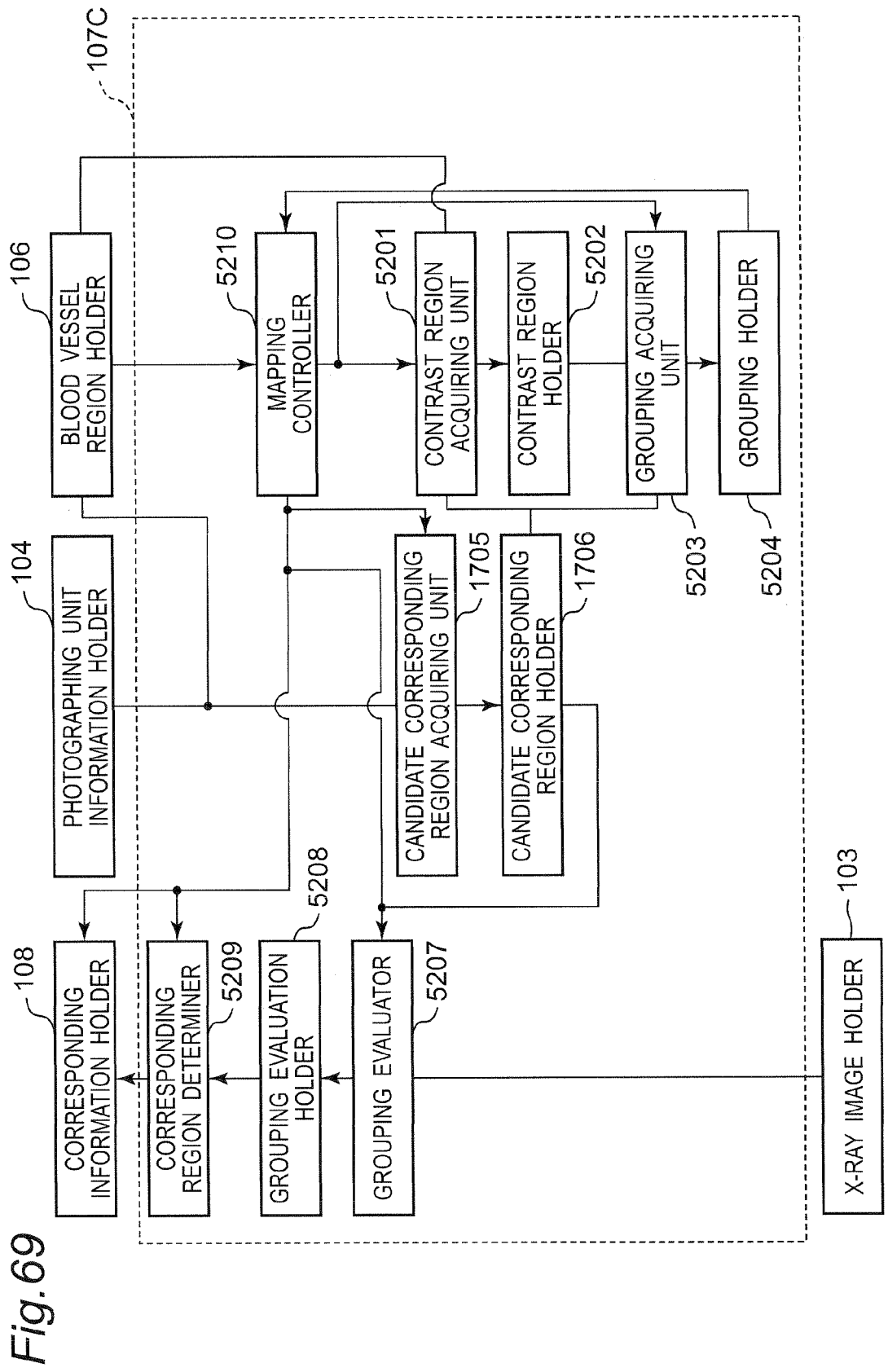
FIG. 69 is a view of the configuration of a mapping unit according to the sixth embodiment.

A mapping unit 107C is included in place of the mapping unit 107 according to the third embodiment. FIG. 69 is a view of the configuration of the mapping unit 107C.

The mapping unit 107C includes the candidate corresponding region acquiring unit 1705, the candidate corresponding region holder 1706, a contrast region acquiring unit 5201, a contrast region holder (holding unit) 5202, a grouping acquiring unit 5203, a grouping holder (holding unit) 5204, a grouping evaluator (evaluating unit) 5207, a grouping evaluation holder (holding unit) 5208, and a corresponding region determiner (determining unit) 5209.

The contrast region acquiring unit 5201 acquires positions of contrast points Pk_m (m=1, 2, . . . , M) on a straight line (epipolar line) where an epipolar plane including the contrast point Pk designated by a mapping controller (controlling unit) 5210 to be described later and a blood vessel region in the first blood vessel region image 1101 cross each other, and stores the positions in the contrast region holder 5202. A contrast point Pk_0 is assumed to be the same as the contrast point Pk.

A specific method is described below. A parameter l1 of an epipolar line L1 is initially calculated in accordance with Equation 14.

$$l1 = F^T m \qquad \text{(Equation 14)}$$

In Equation 14, F denotes a matrix called a fundamental matrix that is calculated in accordance with Equation 8, and $F^T$ denotes a transposed matrix of the fundamental matrix F. Furthermore, m denotes coordinates of an arbitrary projection point Qk_n acquired from the candidate corresponding region holder 1706.

Assume that the calculated parameter l1 of the epipolar line L1 is expressed by (a, b, c) T, the epipolar line L1 satisfies ax+by +c=0. Coordinates of an intersection point between the calculated epipolar line L1 and the first blood vessel region image 1101 are acquired similarly to the case of the candidate corresponding region acquiring unit 1705, and will not be described repeatedly.

The contrast region holder 5202 holds the coordinates of the contrast points Pk_m (m=1, 2, . . . , M) acquired by the contrast region acquiring unit 5201.

The grouping acquiring unit 5203 generates grouping of the contrast points Pk_m (m=1, 2, . . . , M) and the projection points Qk_n (n=1, 2, . . . , N). In an exemplary case where m=3 and n=2 are established, six grouping options are generated as indicated in FIG. 79. Grouping numbers (n=1, 2, . . . , N), grouping results, and the number of figures showing corresponding epipolar sections are indicated in first, second, and third rows, respectively, in FIG. 79

Figure 70:
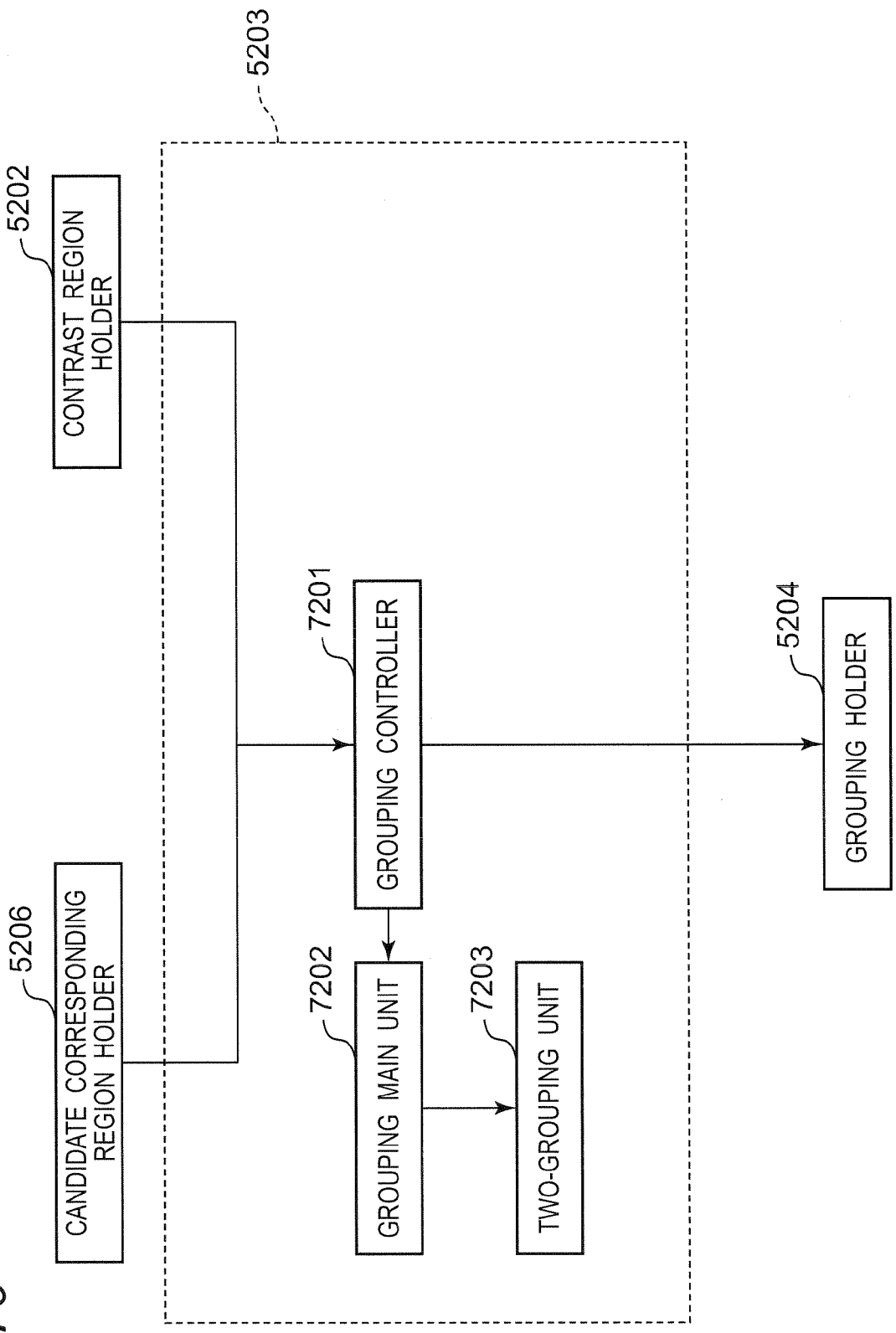
FIG. 70 is an exemplary view of grouping acquired by a grouping acquiring unit according to the sixth embodiment.

FIG. 70 is a view of the configuration of the grouping acquiring unit 5203. The grouping acquiring unit 5203 includes a grouping controller (controlling unit) 7201, a grouping main unit 7202, and a two-grouping unit 7203.

The two-grouping unit 7203 generates a set of two-grouping for a group designated by the grouping main unit 7202, and transmits the set to the grouping main unit 7202.

Described below is a specific exemplary case of two-grouping when the grouping main unit 7202 transmits a group G={{F1, F2, F3}, {S1, S2}} to the two-grouping unit 7203. FIG. 71 is a view of sets for two-grouping (into a group G0 and a group G1). The view in FIG. 71 has one set in each line. Each row includes a numerical value indicating to which group each element in a mass belongs. The value "0" indicates that an element is assigned to the group G0 whereas the value "1" indicates that an element is assigned to the group G1. In the set in the first line, an identifier S2 is assigned to the group G1 and other identifiers F1 to S1 are assigned to the group G0, for example. As indicated in FIG. 71, the group to which a first element in a mass G is assigned is called the group G0.

The number of grouping sets is $2^{\wedge}(N-1)-1$ when the total number of elements is N, and generated are sets of the numbers from 1 to $2^{\wedge}(N-1)-1$. An operator "^" indicates exponentiation operation. In the view in FIG. 71, a U-th column from the right end has a value of (number) % ($2^{\wedge}$U).

FIG. 72 exemplifies indications of respective element groups by grouping into groups 0 and 1 in accordance with FIG. 71.

The grouping controller 7201 acquires a number M of contrast regions held by the contrast region holder 5202 and a number N of candidate corresponding regions held by the candidate corresponding region holder 1706, causes the grouping main unit 7202 to be described later to execute grouping with arguments of a first element group {1, 2, . . . , M} and a second element group {1, 2, . . . , N}, and stores the grouping acquired by the grouping main unit 7202 in the grouping holder 5204.

The grouping main unit 7202 groups a first element group F {F_1, . . . , F_M} and a second element group S {S_1, . . . , S_N} having been designated. The grouping main unit 7202 groups the designated elements into groups satisfying the following conditions.

Condition 1: One element certainly belongs to one group. One element does not belong to a plurality of groups.

Condition 2: One group includes one or more elements in the first element group and one or more elements in the second element group.

Condition 3: Each group includes only one element in the first element group or only one element in the second element group.

Figure 73:
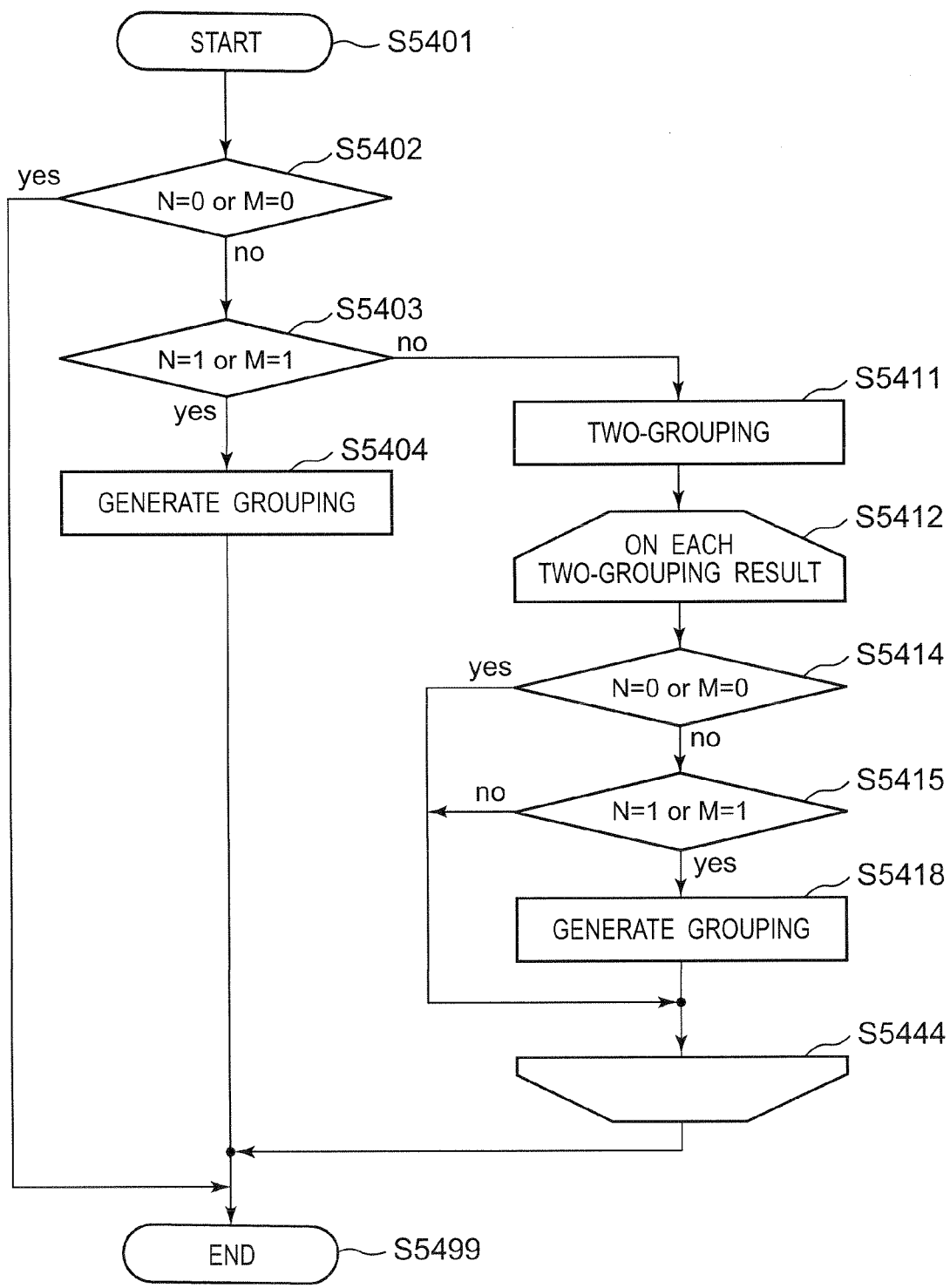
FIG. 73 is a flowchart of a grouping unit according to the sixth embodiment.

FIG. 73 is a flowchart of a flow of the processes executed by the grouping main unit 7202.

Initially in step S5401, the grouping main unit 7202 starts grouping the first element group F {F_1, . . . , F_M} and the second element group S {S_1, . . . , S_N} having been designated.

Subsequently in step S5402, the grouping main unit 7202 decides whether or not the number M of elements in the first element group has the value "0", or whether or not the number N of elements in the second element group has the value "0". If any one of the number M and the number N is "0", the flow branches to step S5499 and ends the processes. Otherwise, the flow branches to step S5403.

Subsequently in step S5403, the grouping main unit 7202 decides whether or not the number M of elements in the first element group has the value "1", or whether or not the number N of elements in the second element group has the value "1". If any one of the number M and the number N is "1", the flow branches to step S5404. Otherwise, the flow branches to step S5411.

Then in step S5404, the grouping main unit 7202 forms a group including all the elements {F_1, . . . , F_M} in the first element group and all the elements {S_1, . . . , S_N} in the second element group, and outputs the group [{F_1, . . . , F_M}, {S_1, . . . , S_N}] as a result of the processes of the grouping main unit 7202, and ends the processes in step S5499.

In a case where the first element group F includes {1, 2} and the second element group S includes {1}, the grouping main unit 7202 outputs a group [{1, 2}, {1}]. In another case where the first element group F includes {1} and the second element group S includes {2}, the grouping main unit 7202 outputs a group [{1}, {2}].

In step S5411, the grouping main unit 7202 causes the two-grouping unit 7203 to execute the above-described process. More specifically, the two-grouping unit 7203 acquires the two-grouping result indicated in FIG. 72.

The grouping main unit 7202 executes the looping processes from steps S5412 to S444 to each grouping result acquired by execution of the two-grouping unit 7203. In the case of FIG. 72, the looping processes from steps S5412 to S444 are executed to the grouping in each line in FIG. 72.

Then in step S5414, the grouping main unit 7202 executes condition decision to a group 0 generated by two-grouping. In other words, the grouping main unit 7202 decides whether or not the following condition is satisfied.

Condition: The number of elements in the first element group is "0" or the number of elements in the second element group is "0".

If the grouping main unit 7202 decides that the condition is satisfied in step S5414, the flow branches to step S5444. If the grouping main unit 7202 decides that the condition is not satisfied in step S5414, the flow branches to step S5415.

The group 0 includes an element group with the number of elements of "0" in Nos. "3, 7, 11, and 15" in FIG. 72. The flow thus branches to step S5444.

The group 1 includes an element group with the number of elements of "0" in Nos. "1, 2, (3,) 4, 8, and 12" in FIG. 72. The flow thus branches to step S5444.

Otherwise, namely, in Nos. "5, 6, 9, 10, 13, and 14", the flow branches to step S5415.

In step S5415, the grouping main unit 7202 executes condition decision to the group 0 generated by two-grouping. In other words, the grouping main unit 7202 decides whether or not the following condition is satisfied.

Condition: The number of elements in the first element group is "1" or the number of elements in the second element group is "1".

If the grouping main unit 7202 decides that the condition is satisfied, the flow branches to step S5418. If the grouping main unit 7202 decides that the condition is not satisfied, the flow branches to step S5444.

The flow branches to step S5418 in Nos. "5, 6, 9, 10, 13, and 14" in FIG. 72.

In step S5418, the grouping main unit 7202 generates grouping for the group 0 that is generated by two-grouping, and stores the grouping in the grouping holder 5204.

Figure 74:
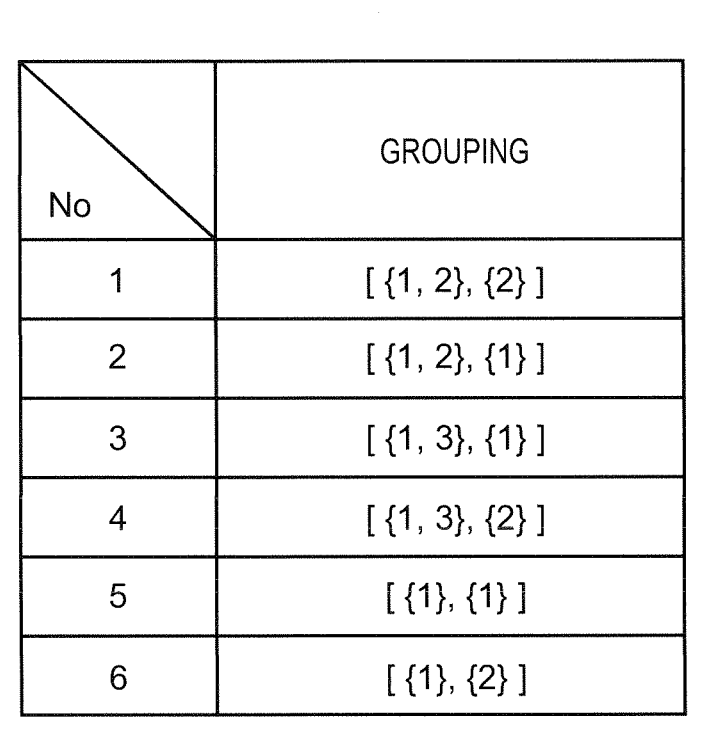

FIG. 74 indicates grouping generated in step S5418 in Nos. "5, 6, 9, 10, 13, and 14" in FIG. 72.

The grouping main unit 7202 executes the processes as described above.

The grouping holder 5204 holds sets of grouping options Gw (w=1, 2, . . . , W; where W is the number of grouping options) acquired by the grouping acquiring unit 5203. A grouping option is added every time the grouping main unit 7202 executes the process in step S5404 or S5418.

Figure 75:
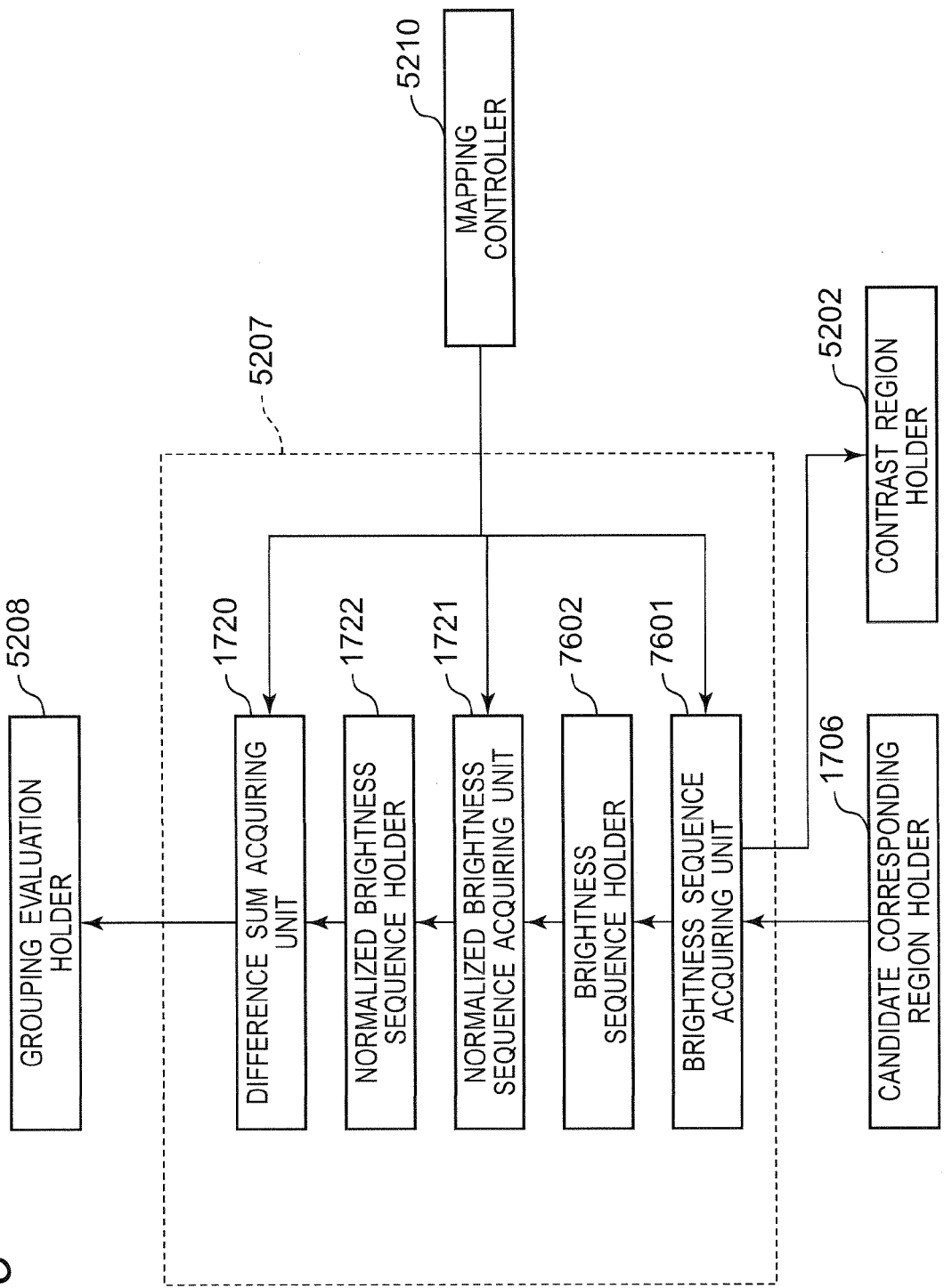
FIG. 75 is an exemplary view of a grouping result of the grouping unit according to the sixth embodiment.

The grouping evaluator 5207 acquires evaluation values Hw (w=1, 2, . . . , W) for the respective grouping options Gw (w=1, 2, . . . , W) held by the grouping holder 5204, and stores the evaluation values thus acquired in the grouping evaluation holder 5208. FIG. 75 is a view of the configuration of the grouping evaluator 5207. The grouping evaluator 5207 includes a brightness sequence acquiring unit 7601, a brightness sequence holder (holding unit) 7602, the normalized brightness sequence acquiring unit 1721, the normalized brightness sequence holder 1722, and the difference sum acquiring unit 1720. The normalized brightness sequence acquiring unit 1721, the normalized brightness sequence holder 1722, and the difference sum acquiring unit 1720 are configured similarly to those according to the third embodiment, and will not be described repeatedly.

The brightness sequence acquiring unit 7601 acquires a brightness sequence of the sum of the contrast points Pk_m (m=1, 2, . . . , M) belonging to the designated grouping Gw and a brightness sequence of the sum of the candidate corresponding points Qk_n (n=1, 2, . . . , N) held by the candidate corresponding region holder 1706.

The brightness sequence holder 7602 holds the brightness sequences acquired by the brightness sequence acquiring unit 7601. In accordance with the brightness sequences held by the brightness sequence holder 7602, the difference sum acquiring unit 1720 executes difference summing similar to that of the difference sum acquiring unit 1720 according to the third embodiment, and transmits the evaluation values Hw (w=1, 2, . . . , W) to the grouping evaluation holder 5208.

The grouping evaluation holder 5208 holds the evaluation values Hw (w=1, 2, . . . , W) acquired by the grouping evaluator 5207.

The corresponding region determiner 5209 selects a minimum evaluation value Hx from the evaluation values held by the grouping evaluation holder 5208.

Figure 76:
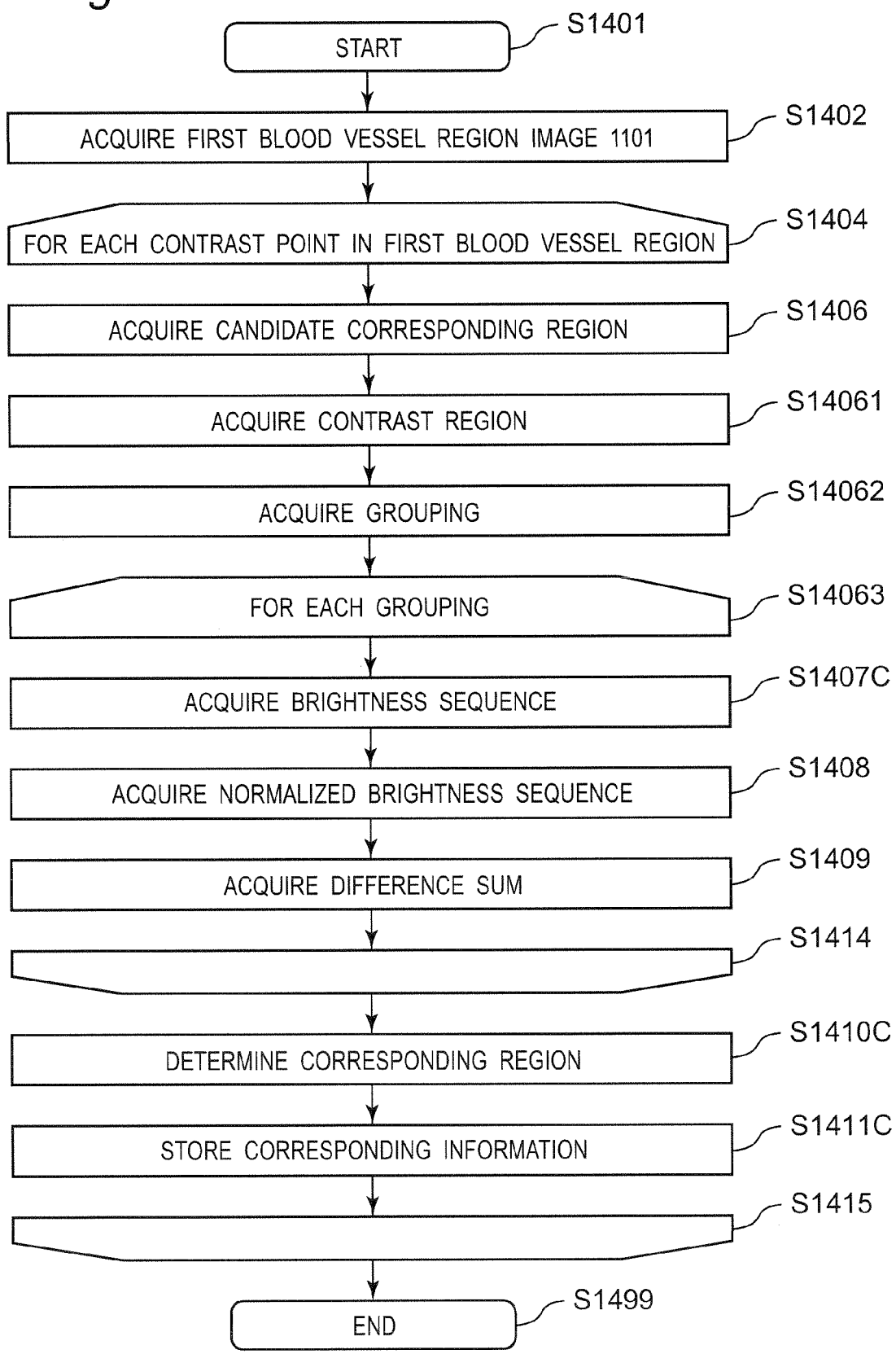
FIG. 76 is a flowchart of the processes executed by a brightness sequence acquiring unit according to the sixth embodiment.

The mapping controller 5210 controls the respective units in the mapping unit 107C to execute mapping. FIG. 76 is a flowchart of a flow of the processes executed by the mapping controller 5210.

The mapping controller 5210 starts the processes in step S1401.

Subsequently in step S1402, the mapping controller 5210 acquires the first blood vessel region image 1101 from the blood vessel region holder 106.

The mapping controller 5210 executes the processes in steps S1404 to S1415 to the black point in the blood vessel region on the first blood vessel region image 1101 acquired in step S1402. Assume that the black point corresponds to each of the contrast points Pk (k=1, 2, . . . , K; where K is the number of black points) in the following description.

Then in step S1406, the mapping controller 5210 commands the candidate corresponding region acquiring unit 1705 to execute the process. The candidate corresponding region acquiring unit 1705 acquires the candidate corresponding points Qk_n (n=1, 2, . . . , N) of the contrast point Pk, and stores coordinates of the candidate corresponding points Qk_n (n=1, 2, . . . , N) thus acquired in the candidate corresponding region holder 1706.

Then in step S14061, the mapping controller 5210 commands the contrast region acquiring unit 5201 to execute the process. The contrast region acquiring unit 5201 acquires the contrast points Pk_m (m=1, 2, . . . , M) included in the epipolar plane that also includes the contrast point Pk, and stores coordinates of the contrast points Pk_m (m=1, 2, . . . , M) thus acquired in the contrast region holder 5202.

Then in step S14062, the mapping controller 5210 commands the grouping acquiring unit 5203 to execute the process. The grouping acquiring unit 5203 generates the grouping options Gw (w=1, 2, . . . , W) for the contrast points Pk_m (m=1, 2, . M) and the candidate corresponding points Qk_n (n=1, 2, . N).

The mapping controller 5210 executes the processes in steps S14063 to S1414 to the grouping options Gw (w=1, 2, . W) acquired in step S14062.

Initially in step S1407C, the mapping controller 5210 commands the brightness sequence acquiring unit 7601 to execute the process. The brightness sequence acquiring unit 7601 acquires a brightness sequence of the sum of brightness of the contrast points Pk_m (m=1, 2, . . . , M) belonging to the grouping Gw and a brightness sequence of the sum of brightness of the candidate corresponding points Qk_n (n=1, 2, . . . , N) belonging to the grouping Gw, and stores the brightness sequences in the brightness sequence holder 7602.

Then in step S1408, the mapping controller 5210 commands the normalized brightness sequence acquiring unit 1721 to execute the process. The normalized brightness sequence acquiring unit 1721 normalizes the brightness sequence of the sum of the contrast points Pk_m and the brightness sequence of the sum of the candidate corresponding points Qk_n held by the brightness sequence holder 7602, and stores the normalized brightness sequences in the normalized brightness sequence holder 1722.

Subsequently in step S1409, the mapping controller 5210 commands the difference sum acquiring unit 1720 to execute the process. The difference sum acquiring unit 1720 calculates the sum Hw of the brightness differences at respective times between the normalized brightness sequence of the sum of the contrast points Pk_m and the normalized brightness sequence of the sum of the candidate corresponding points Qk_n, stores the sum Hw in the grouping evaluation holder 5208, and ends the process in step S1414.

Then in step S1410C, the mapping controller 5210 commands the corresponding region determiner 5209 to execute the process. The corresponding region determiner 5209 acquires a minimum evaluation value Hα from the evaluation values Hw (w=1, 2, . . . , W) held by the grouping evaluation holder 5208. Reference character α is the number of the grouping for the selected evaluation value. Assume that α=2 (corresponding to the grouping in FIG. 61) is selected in the case of FIG. 74.

Then in step S1411C, the mapping controller 5210 stores, in the corresponding information holder 108, coordinates of the contrast points Pk_m (m=1, 2, . . . , M) belonging to grouping Gα, coordinates of the candidate corresponding points Qk_n (n=1, 2, . . . , N) belonging to the grouping Gα, and the evaluation value Hα, and ends the process in step S1415.

FIG. 77 indicates corresponding information to be added in a case where the grouping Gα includes a plurality of contrast points Pk_m. As indicated in FIG. 77, the corresponding information holder 108 stores lines including the candidate corresponding point Qk_1 as the corresponding point of the contrast points Pk_m (m=1, 2, . . . , M). FIG. 78 indicates corresponding information to be added in a case where the grouping Gα includes a plurality of candidate corresponding points Qk_n (n=1, 2, . . . , N). As indicated in FIG. 78, the corresponding information holder 108 stores lines including the candidate corresponding points Qk_n (n=1, 2, . . . , N) as the corresponding points of the contrast point Pk_1.

The mapping controller 5210 ends the processes in step S1499.

<Effects of the Sixth Embodiment>

The sixth embodiment exerts effects similar to those of the third embodiment.

The contrast points and the candidate corresponding points are assigned into the two groups in the present embodiment. Alternatively, {contrast points, candidate corresponding points} assigned into a group different from the group including the contrast point Pk_1 can be further grouped, and the sum of the evaluation values for the respective grouping options can be regarded as a new reference evaluation value.

(Other Embodiments)

Described in the third embodiment is the exemplary flow of the processes. Alternatively, the order of the processes can be changed, or a plurality of processes can be executed parallelly (simultaneous parallel processing).

The elements included in the shape restoring apparatuses 10, 20, 1, 1A, 1B, and 1C can be partially or entirely configured to be actually a computer system that includes, for example, a microprocessor, ROM, RAM, hard disk unit, display unit, keyboard, mouse, and the like. A computer program is stored on the RAM or the hard disk unit. Functions of each of the apparatuses can be achieved by the microprocessor operating according to the computer program. The computer program mentioned here is a combination of a plurality of instruction codes that indicate commands to a computer for achieving predetermined functions.

The elements included in the shape restoring apparatuses 10, 20, 1, 1A, 1B, and 1C can be partially or entirely configured by one system large scale integration (LSI). A system LSI is a super-multifunctional LSI that includes a plurality of the configurations integrated on one chip, more particularly, is a computer system including a microprocessor, a ROM, a RAM, and the like. A computer program is stored in the RAM. The system LSI realizes its function when the microprocessor operates in accordance with the computer program.

The elements included in the shape restoring apparatuses 10, 20, 1, 1A, 1B, and 1C can be partially or entirely configured by an IC card or a monolithic module detachably attached to a corresponding apparatus. The IC card or the module is a computer system including a microprocessor, a ROM, a RAM, and the like. The IC card or the module can alternatively include the super-multifunctional LSI. The IC card or the module realizes its function when the microprocessor operates in accordance with the computer program. The IC card or the module can alternatively have the tamper resistant property.

The elements included in the shape restoring apparatuses 10, 20, 1, 1A, 1B, and 1C are partially or entirely applicable to methods of acquiring a tube shape. The present disclosure can be embodied by a computer program configured to cause a computer to acquire a tube shape, or digital signals configured by a computer program in accordance with the methods.

The elements included in the shape restoring apparatuses 10, 20, 1, 1A, 1B, and 1C can be partially or entirely embodied when recorded in a recording medium configured to cause a computer to read the computer program or the digital signals, such as a flexible disk, a hard disk, a CD-ROM, an MO, a DVD, a DVD-ROM, a DVD-RAM, a Blu-ray (registered trademark) disc (BD), or a semiconductor memory. These can be embodied by digital signals recorded in the recording medium.

The elements included in the shape restoring apparatuses 10, 20, 1, 1A, 1B, and 1C can be partially or entirely embodied by the computer program or the digital signals that are transmitted through a telecommunication line, a wireless communication line, a wired communication line, a network represented by the Internet, data broadcasting, or the like.

The elements included in the shape restoring apparatuses 10, 20, 1, 1A, 1B, and 1C can be partially or entirely embodied by a computer system including a microprocessor and a memory. Such a memory stores the computer program, and the microprocessor operates in accordance with the computer program.

Another independent computer system can execute the processes according to the present disclosure by transfer of the computer program or the digital signals that is recorded in a recording medium, or transfer of the computer program or the digital signals by way of a network or the like.

By properly combining the arbitrary embodiment (s) or modification(s) of the aforementioned various embodiments and modifications, the effects possessed by the embodiment (s) or modification(s) can be produced.

INDUSTRIAL APPLICABILITY

The image region mapping device, the 3D model generating apparatus, the image region mapping method, and the image region mapping program according to one of the aspects of the present disclosure enable mapping of a plurality of image regions in X-ray images of a blood vessel captured in two directions as well as generation of a 3D model of the blood vessel in accordance with the mapping result, and are thus useful for catheterization and the like.

The entire disclosure of Japanese Patent Application No. 2013-079216 filed on Apr. 5, 2013, including specification, claims, drawings, and summary are incorporated herein by reference in its entirety. Although the present disclosure has been fully described in connection with the embodiments thereof with reference to the accompanying drawings, it is to be noted that various changes and modifications are apparent to those skilled in the art. Such changes and modifications are to be understood as included within the scope of the present disclosure as defined by the appended claims unless they depart therefrom.

What is claimed is:

1. An image region mapping device configured to map a plurality of image regions of a blood vessel having a bifurcation, the device comprising:
    a projection image acquiring unit configured to capture the blood vessel through which a contrast medium is passing, serially at first and second photographing angles different from each other to acquire a plurality of image sets each including a first projection image captured at the first photographing angle and a second projection image captured at the second photographing angle;
    a first brightness change acquiring unit configured to acquire brightness change information on the contrast medium for a predetermined time period in a first image region at a predetermined potion after the bifurcation on the first projection image in each of the image sets acquired by the projection image acquiring unit;
    a second brightness change acquiring unit configured to acquire brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;
    a similarity degree calculator configured to calculate a similarity degree between the brightness change information acquired by the first brightness change acquiring unit and each of the brightness change information pieces acquired by the second brightness change acquiring unit; and
    a corresponding region determiner configured to determine one of the second image regions corresponding to the first image region in accordance with the similarity degrees calculated by the similarity degree calculator.

2. The image region mapping device according to claim 1, wherein the first brightness change acquiring unit acquires brightness of the contrast medium at each of a plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a brightness normalizer configured to normalize brightness, the brightness normalizer, normalizes by calculating a difference value between reference brightness in a case of not capturing the blood vessel and the brightness acquired by the first brightness change acquiring unit to acquire normalized brightness change information, and normalizes by calculating a difference value between the reference brightness in the case of not capturing the blood vessel and the brightness acquired by the second brightness change acquiring unit to acquire normalized brightness change information, and the similarity degree calculator calculates a similarity degree between the brightness change information acquired by the first brightness change acquiring unit and normalized by the brightness normalizer and each of the brightness change information pieces acquired by the second brightness change acquiring unit and normalized by the brightness normalizer.

3. The image region mapping device according to claim 2, wherein the first brightness change acquiring unit acquires brightness of the contrast medium at each of the plurality of times in the first image region as brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the brightness normalizer normalizes the brightness change information at each of the times acquired by each of the first brightness change acquiring unit and the second brightness change acquiring unit to acquire normalized brightness change information, the similarity degree calculator calculates a difference between the brightness at each of the times acquired by the first brightness change acquiring unit and normalized by the brightness normalizer and each of the brightness change information pieces at each of the times acquired by the second brightness change acquiring unit and normalized by the brightness normalizer to calculate, as a similarity degree, a sum of absolute values of the differences for the predetermined time period, and the corresponding region determiner determines that the second image region having a minimum sum of the absolute values of the differences calculated by the similarity degree calculator as the similarity degree corresponds to the first image region.

4. The image region mapping device according to claim 3, further comprising:

a photographing unit information acquiring unit configured to acquire relative positional information between positional information on a first radiographing device configured to capture the blood vessel at the first photographing angle and positional information on a second radiographing device configured to capture the blood vessel at the second photographing angle;

a blood vessel region acquiring unit configured to acquire positional information on the first image region on the first projection image; and a candidate corresponding region acquiring unit configured to calculate an epipolar plane defined by the first radiographing device, the second radiographing device, and the first image region from the positional information acquired by the photographing unit information acquiring unit, calculate an epipolar line as an intersection line between the calculated epipolar plane and the second projection image on the second projection image, and acquire positional information positioned on the calculated epipolar line for each of the plurality of second image regions, and the second brightness change acquiring unit acquires a brightness change at a position of the positional information in each of the plurality of second image regions acquired by the candidate corresponding region acquiring unit.

5. A 3D model generating apparatus configured to generate a 3D model of the blood vessel having the bifurcation, the apparatus comprising:

the image region mapping device according to claim 3; and a 3D model generator configured to generate the 3D model of the blood vessel in accordance with the information determined by the image region mapping device.

6. The image region mapping device according to claim 2, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the first brightness change acquiring unit acquires a graph by chronologically plotting the brightness of the contrast medium in the first image region as the brightness change information, the second brightness change acquiring unit acquires a graph by chronologically plotting the brightness of the contrast medium in each of the plurality of second image regions as the brightness change information, the brightness normalizer normalizes the graphs acquired by the first brightness change acquiring unit and the second brightness change acquiring unit to acquire normalized graphs, the similarity degree calculator calculates a similarity degree in shape between the graph acquired by the first brightness change acquiring unit and normalized by the brightness normalizer and each of the plurality of graphs acquired by the second brightness change acquiring unit and normalized by the brightness normalizer, and the corresponding region determiner determines that the second image region having a highest similarity degree in shape calculated by the similarity degree calculator corresponds the first image region.

7. The image region mapping device according to claim 6, wherein the similarity degree calculator calculates as a similarity degree, a difference between an area of the graph acquired by the first brightness change acquiring unit and normalized by the brightness normalizer and an area of each of the plurality of graphs acquired by the second brightness change acquiring unit and normalized by the brightness normalizer, and the corresponding region determiner determines that the second image region of the graph having a minimum difference calculated by the similarity degree calculator as the similarity degree corresponds to the first image region.

8. The image region mapping device according to claim 2, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a predetermined ratio time acquiring unit configured to acquire a predetermined ratio time when brightness of a point in each of the first image region and the second image regions reaches a predetermined ratio to maximum brightness of the point, the predetermined ratio time acquiring unit acquires the predetermined ratio time when a brightness sequence as the brightness change information normalized by the brightness normalizer in each of the first image region and the second image regions has a value reaching the predetermined ratio, and the similarity degree calculator determines that, in the plurality of second image regions, the second image region having the predetermined ratio time having a higher similarity degree to the predetermined ratio time of the first image region corresponds to the first image region.

9. The image region mapping device according to claim 2, wherein the first brightness change acquiring unit acquires brightness of the contrast medium at each of the plurality of times in the first image region as the brightness change information on the contrast medium for the predetermined time period, the second brightness change acquiring unit acquires brightness of the contrast medium at each of the plurality of times in each of the plurality of second image regions as the brightness change information on the contrast medium for the predetermined time period, the image region mapping device further comprises a peak time acquiring unit configured to acquire a peak time of a differential brightness sequence obtained by differentiating a brightness sequence serving as the brightness change information normalized by the brightness normalizer in each of the first image region and the second image regions, the peak time acquiring unit acquires the peak time of the differential brightness sequence obtained by differentiating the brightness sequence in each of the first image region and the second image regions, and the similarity degree calculator determines that, in the plurality of second image regions, the second image region having the peak time having a higher similarity degree to the peak time of the first image region corresponds to the first image region.

10. The image region mapping device according to claim 2, further comprising:

a photographing unit information acquiring unit configured to acquire relative positional information between positional information on a first radiographing device configured to capture the blood vessel at the first photographing angle and positional information on a second radiographing device configured to capture the blood vessel at the second photographing angle;

a blood vessel region acquiring unit configured to acquire positional information on the first image region on the first projection image; and a candidate corresponding region acquiring unit configured to calculate an epipolar plane defined by the first radiographing device, the second radiographing device, and the first image region from the positional information acquired by the photographing unit information acquiring unit, calculate an epipolar line as an intersection line between the calculated epipolar plane and the second projection image on the second projection image, and acquire positional information positioned on the calculated epipolar line for each of the plurality of second image regions, and the second brightness change acquiring unit acquires a brightness change at a position of the positional information in each of the plurality of second image regions acquired by the candidate corresponding region acquiring unit.

11. A 3D model generating apparatus configured to generate a 3D model of the blood vessel having the bifurcation, the apparatus comprising:

the image region mapping device according to claim 2; and a 3D model generator configured to generate the 3D model of the blood vessel in accordance with the information determined by the image region mapping device.

12. The image region mapping device according to claim 1, further comprising:

a photographing unit information acquiring unit configured to acquire relative positional information between positional information on a first radiographing device configured to capture the blood vessel at the first photographing angle and positional information on a second radiographing device configured to capture the blood vessel at the second photographing angle;

a blood vessel region acquiring unit configured to acquire positional information on the first image region on the first projection image; and a candidate corresponding region acquiring unit configured to calculate an epipolar plane defined by the first radiographing device, the second radiographing device, and the first image region from the positional information acquired by the photographing unit information acquiring unit, calculate an epipolar line as an intersection line between the calculated epipolar plane and the second projection image on the second projection image, and acquire positional information positioned on the calculated epipolar line for each of the plurality of second image regions, and the second brightness change acquiring unit acquires a brightness change at a position of the positional information in each of the plurality of second image regions acquired by the candidate corresponding region acquiring unit.

13. A 3D model generating apparatus configured to generate a 3D model of the blood vessel having the bifurcation, the apparatus comprising:

the image region mapping device according to claim 1; and a 3D model generator configured to generate the 3D model of the blood vessel in accordance with the information determined by the image region mapping device.

14. An image region mapping method of mapping a plurality of image regions of a blood vessel having a bifurcation, the method comprising:

with a projection image acquiring unit, capturing the blood vessel through which a contrast medium is passing, serially at first and second photographing angles different from each other to acquire a plurality of image sets each including a first projection image captured at the first photographing angle and a second projection image captured at the second photographing angle;

with a first brightness change acquiring unit, acquiring brightness change information on the contrast medium for a predetermined time period in a first image region at a predetermined potion after the bifurcation on the first projection image in each of the image sets acquired by the projection image acquiring unit;

with a second brightness change acquiring unit, acquiring brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

with a similarity degree calculator, calculating a similarity degree between the brightness change information acquired by the first brightness change acquiring unit and each of the brightness change information pieces acquired by the second brightness change acquiring unit; and with a corresponding region determiner, determining one of the second image regions corresponding to the first image region in accordance with the similarity degrees calculated by the similarity degree calculator.

15. A non-transitory computer-readable recording medium including an image region mapping program configured to map a plurality of image regions of a blood vessel having a bifurcation, the program causing a computer to function as:

a projection image acquiring unit configured to capture the blood vessel through which a contrast medium is passing, serially at first and second photographing angles different from each other to acquire a plurality of image sets each including a first projection image captured at the first photographing angle and a second projection image captured at the second photographing angle;

a first brightness change acquiring unit configured to acquire brightness change information on the contrast medium for a predetermined time period in a first image region at a predetermined potion after the bifurcation on the first projection image in each of the image sets acquired by the projection image acquiring unit;

a second brightness change acquiring unit configured to acquire brightness change information on the contrast medium for the predetermined time period in each of a plurality of second image regions at the predetermined potion after the bifurcation on the second projection image in each of the image sets acquired by the projection image acquiring unit, the second image regions being candidates corresponding to the first image region;

a similarity degree calculator configured to calculate a similarity degree between the brightness change information acquired by the first brightness change acquiring unit and each of the brightness change information pieces acquired by the second brightness change acquiring unit; and a corresponding region determiner configured to determine one of the second image regions corresponding to the first image region in accordance with the similarity degrees calculated by the similarity degree calculator.

* * * * *